United States Patent [19]
Rodgers et al.

[11] Patent Number: 6,110,895
[45] Date of Patent: Aug. 29, 2000

[54] METHOD OF PROMOTING HEALING IN SKIN GRAFTS

[75] Inventors: Kathleen E. Rodgers, Long Beach; Gere S. DiZerega, Pasadena, both of Calif.

[73] Assignee: University of Southern California, Los Angeles, Calif.

[21] Appl. No.: 08/990,664

[22] Filed: Dec. 15, 1997

Related U.S. Application Data

[60] Provisional application No. 60/028,310, Dec. 16, 1996.

[51] Int. Cl.$^7$ .................................................. A61K 38/08
[52] U.S. Cl. ............................ 514/15; 514/16; 530/316; 530/327; 530/328; 530/329; 600/36
[58] Field of Search ........................ 514/15, 16; 530/316, 530/327, 328, 329; 600/36

[56] References Cited

U.S. PATENT DOCUMENTS

| | | | |
|---|---|---|---|
| 5,333,527 | 8/1994 | Brysk | 435/240.23 |
| 5,474,770 | 12/1995 | Broly et al. | 424/94.64 |
| 5,534,026 | 7/1996 | Manders et al. | 623/15 |

FOREIGN PATENT DOCUMENTS

| | | | |
|---|---|---|---|
| 4430601A1 | 2/1996 | Germany. | |
| WO 9508337 | 3/1995 | WIPO. | |
| WO95/08337 | 3/1995 | WIPO | A61K 37/00 |
| WO95/08565 | 3/1995 | WIPO | C07K 7/06 |
| WO 9614858 | 5/1996 | WIPO. | |
| WO 9639164 | 12/1996 | WIPO. | |

OTHER PUBLICATIONS

File Embase on STN. No. 84113177. Marvin et al. 'improved treatment of the Stevens–Johnson syndrome', Arch. Surg. 119/5, pp. 601–605, 1984.

File Embase on STN. No. 89227561. Taylor et al. 'Toxic epeidermal nercolysis, A comprehensive apporach. Mulidisciplinary managment in a burn center', Clin. Pediatr. 28/9, pp. 404–407, 1989.

File Embase on STN. No. 85022998. Ersek et al. 'Silver–impregnated procine xenograft for treatment of meshed autografts', Ann. Plast. Surg. 13/6, pp. 482–487, 1984.

Ross R., et al., The Biology of Platelet–Derived Growth Factor, Cell, vol. 46, 155–169 (1986).

Libby, P. et al., Production of Platelet–Derived Growth Factor–Like Mitogen By Smooth–Muscle Cells from Human Atheroma, New England Journal of Medicine vol. 318:23 1493–1498 (1988).

Scherping, S.C., et al. Effect of Growth Factors on the Proliferation of Ligament Fibroblasts from Skeletally Mature Rabbits, Connective Tissue Research vol. 36(1), 1–8 (1997).

Vilcek, J., et al., Fibroblast Growth Enhancing Activity of Tumor Necrosis Factor and its Relationship to Other Polypeptide Growth Factors, J. Exp. Med. vol. 163, 632–643 (1986).

Pedram, A., et al., Extracellular Signal–Regulated Protein/Jun Kinase Cross–talk Underlies Vascular Endothelial Cell Growth Factor–induced Endothelial Cell Proliferation, The Journal of Biological Chemistry, vol. 273, No. 41, 26722–26728 (1998).

Reape, T.J., et al., IGF–I increased bFGF–induced mitogenesis and upregulates FGFR–1 in rabbit vascular smooth muscle cells, The American Physiological Society H1141–H1148 (1996).

Suzuki, A., et al., Catecholamines Stimulate the Proliferation and the Alkaline Phosphatase Activity of MC3T3–E1 Osteoblast–like Cells, Bone vol. 23, No. 3, 197–203 (1998).

Blaes, N., et al., Growth–Stimulating Effect of Catecholamines on Rat Aorthic Smooth Muscle Cells in Culture. Journal of Cellular Physiology 116:167–172 (1983).

Brown, D.M., et al., Treatment of Avascular Ulcers with Cytokine–Induced Tissue Generation and Skin Grafting, The American Journal of Surgery, vol. 171:247–250 (1996).

Stepnick, D.W., et al., Effects of Tumor Necrosis Factor α and Vascular Permeability Factor on Neovascularization of the Rabbit Ear Flap, Arch Otolaryingol Head Neck Surg. vol. 121:667–672 (1995).

Hom, D.B., & Winters, M., Effect of angiogenic growth factors and a penetrance enhancer on composite grafts, Ann. Otol Rhinol Laryingol vol. 107:769–774 (1998).

Hom, DB, et al., Vascular Effects of Sustained–Release Fibroblast Growth Factors, Ann. Otol Rhinol Laryngol vol. 105:109–116 (1996).

Wolfort et al., The Effect of Epinephrine in Local Anesthesia on the Survival of Full–and Split Thickness Skin Grafts: An Experimental Study, Plastic and Reconstructive Surgery, vol. 86, No. 3,:535–540 (1990).

Yessenow, R.S., et al., The Effects of Pentoxifylline on Random Skin Flap Survival, Arch Otolaryngol Head Neck Surg. vol. 115:179–181 (1989).

Davies, B.W., et al., The Impact of Vasodilators on Random–Pattern Skin Flap Survival in the Rat Following Mainstream Smoke Exposure, Annals of Plastic Surgery, vol. 40, No. 6. 630–636 (1998).

Berman, B., et al., Pentoxifylline Inhibits Normal Human Dermal Fibroblast in Vitro Proliferation Collagen, Glycosamineoglycan, and Fibronectin Productions, and Increased Collagenase Activity, The Journal of Investigative Dermatology, vol. 92, No. 4, 605–610 (1989).

Nilson, J., et al., The Calcium Antagonist Nifedipine Inhibits Artoerial Smooth Muscle Cell Proliferation, Atherosclerosis, vol. 58:109–122 (1985).

Shoker, A.S., et al., Analysis of the in vitro effects of exogenous nitric oxide on human lymphocytes, Molecular and Cellular Biochemistry vol. 171:75–83 (1997).

Yang, W., et al., Exogenous Nitric Oxide Inhibits Proliferation of Culture Vascular Endothelial Cells, Biochemical and Biophysical Research Communication, vol. 203, No. 2: 1160–1167 (1994).

*Primary Examiner*—Christopher S. F. Low
*Assistant Examiner*—Anish Gupta
*Attorney, Agent, or Firm*—Knobbe, Martens, Olson & Bear, LLP

[57] ABSTRACT

Angiotensin II angiotensin II fragments, angiotensin II analogs, Angiotensin II Type 2 receptor agonists, angiotensin I or analogs thereof, and angiotensin or analogs thereof are useful in promoting the incorporation of skin grafts into the underlying tissue of the animal.

39 Claims, 31 Drawing Sheets

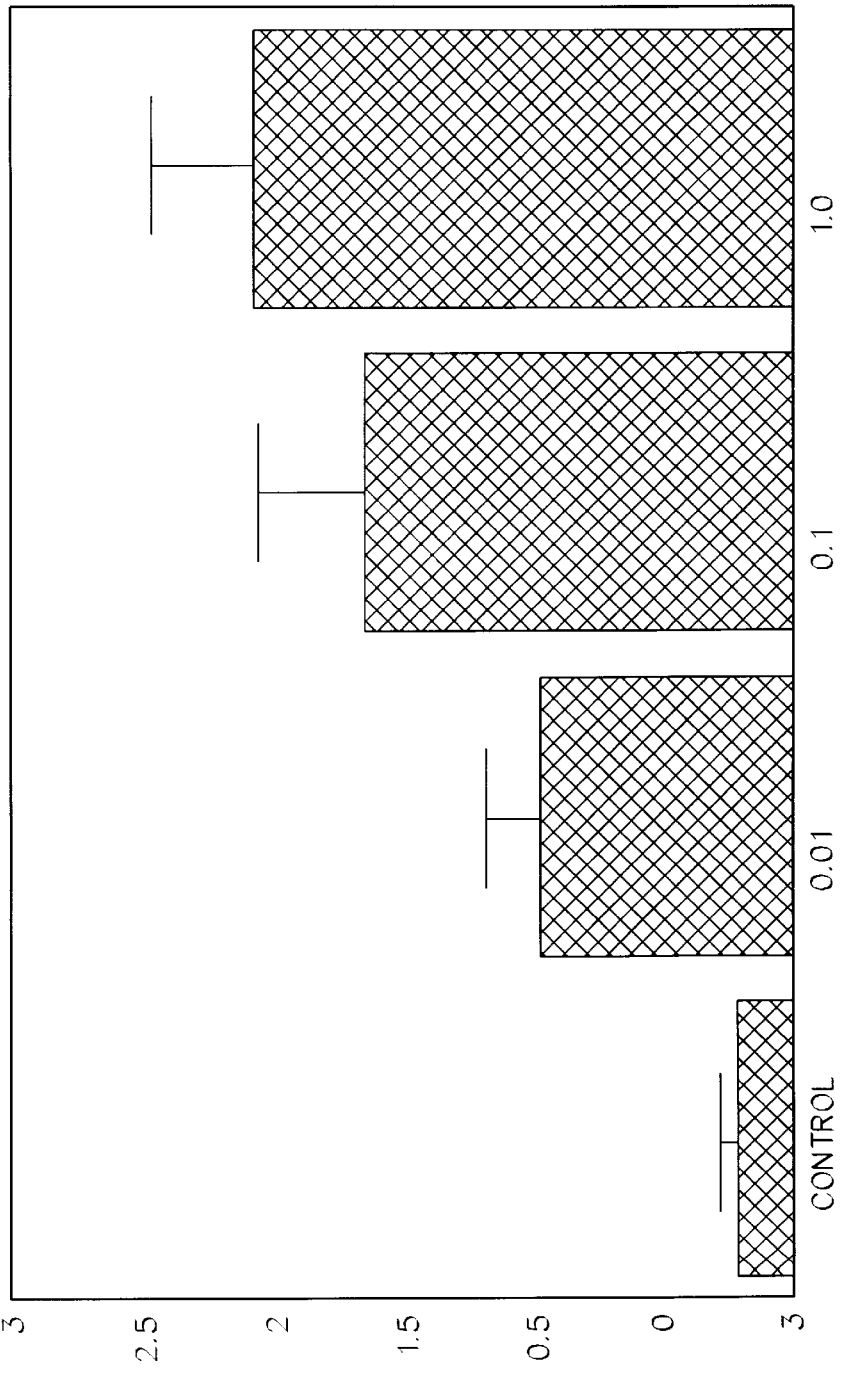

METHOD OF PROMOTING HEALING IN SKIN GRAFTS

RELATED APPLICATIONS

This application claims the benefit of priority under 35 U.S.C. § 119(e) of the provisional application number 60/028,310, filed Dec. 16, 1996. The complete disclosure of this related application is incorporated herein by this reference thereto.

FIELD OF THE INVENTION

This invention relates generally to the fields of biochemistry and medicine. More particularly, the present invention relates to compositions and methods for use in accelerating the growth or healing of skin grafts.

BACKGROUND OF THE INVENTION

Wounds (i.e., lacerations or openings) in mammalian tissue result in tissue disruption and coagulation of the microvasculature at the wound face. Repair of such tissue represents an orderly, controlled cellular response to injury. All soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in great detail and have in some instances been quantified (Hunt et al., "Coagulation and macrophage stimulation of angiogenesis and wound healing," in *The surgical wound*, pp. 1–18, ed. F. Dineen & G. Hildrick-Smith (Lea & Febiger, Philadelphia: 1981)).

The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). While this new blood vessel growth (angiogenesis) is necessary for the healing of wound tissue, angiogenic agents are in general unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of angiotensin II to wound issue significantly increases the rate of wound healing, leading to a more rapid re-epithelialization and tissue repair. The term angiotensin II refers to an octapeptide present in humans and other species having the sequence Asp-Arg-Val-Tyr-Ile-His-Pro-Phe (SEQ ID NO:1). Angiotensin II is a known pressor agent and is commercially available.

Despite the utility of angiotensin II in accelerating wound healing, there remains a need for additional agents which are useful in promoting wound healing. Moreover, it would be highly advantageous to employ an agent which is less potent than angiotensin II at inducing hypertension.

A peptide agonist selective for the AT2 receptor (the peptide has 100 times higher affinity for AT2 than AT1) has been identified. This peptide, which is called p-aminophenylalanine6-AII or "p-$NH_2$-Phe6-AII", has the sequence Asp-Arg-Val-Tyr-Ile-Xaa-Pro-Phe (SEQ ID NO:2) wherein Xaa is p-$NH_2$-Phe (Speth et al. *Biochem Biophys. Res. Commun.* 169:997 (1990)). Discrimination of two angiotensin II receptor subtypes with a selective agonist analogue of angiotensin II, p-aminophenylalanine6 angiotensin II. *Biochem Biophys Res Commun* 169:997). This peptide gave binding characteristics comparable to AT2 antagonist in the experimental models tested (Catalioto et al. *Eur J Pharmacol* 256:93 (1994); Bryson et al. *Eur J Pharmacol* 225:119 (1992)).

It is an object of the present invention to provide compositions and methods which do not suffer from all of the drawbacks of the compositions known heretofore.

SUMMARY OF THE INVENTION

One aspect of the invention relates to a method of promoting incorporation of a skin graft into underlying tissue of a mammal. This method includes the steps of: (1) applying to either the skin graft or the underlying tissue an effective graft incorporation promoting amount of a composition which includes angiotensin II and a pharmacologically acceptable carrier; (2) contacting the skin graft and the underlying tissue; and (3) securing the skin graft to the underlying tissue, whereby incorporation of said skin graft into said underlying tissue is promoted. According to one embodiment the skin graft is an autologous graft. According to a preferred embodiment of the invention, the pharmacologically acceptable carrier includes a buffered saline solution. When the carrier includes buffered saline, the composition that includes angiotensin II can be applied in the applying step by soaking the skin graft. Alternatively, the pharmacologically acceptable carrier can include carboxymethyl cellulose. When the composition includes carboxymethyl cellulose and angiotensin II, it can be applied to the underlying tissue. According to another preferred embodiment, the composition which includes the buffered saline solution and angiotensin II can be applied to the underlying tissue. According to yet other preferred embodiments, the securing step can be accomplished by any of suturing, bandaging or applying a biological glue.

Another aspect of the invention relates to a method of promoting incorporation of a skin graft into underlying tissue of a mammal. This method includes the steps of: (1) applying to either the skin graft or the underlying tissue an effective graft incorporation promoting amount of a composition which includes a pharmacologically acceptable carrier and a peptide consisting of at least three contiguous amino acids of groups $R^1$–$R^8$ in the general formula $$R^1\text{-}R^2\text{-}R^3\text{-}R^4\text{-}R^5\text{-}R^6\text{-}R^7\text{-}R^8$$

in which $R^1$ and $R^2$ together form a group of formula $$X\text{—}R^A\text{-}R^B\text{-},$$

wherein X is H or a one to three peptide group and a peptide bond between $R^A$ and $R^B$ is labile to aminopeptidase A cleavage;

$R^3$ is selected from the group consisting of Val, Ala, Leu, norLeu, Ile, Gly, Pro, Aib, Acpc and Tyr;

$R^4$ is selected from the group consisting of Tyr, Tyr($PO_3$)$_2$, Thr, Ser, homoSer and azaTyr;

$R^5$ is selected from the group consisting of Ile, Ala, Leu, norLeu, Val and Gly;

$R^6$ is His, Arg or 6-$NH_2$-Phe;

R⁷ is Pro or Ala; and
R⁸ is selected from the group consisting of Phe, Phe (Br), Ile and Tyr, excluding sequences including R⁴ as a terminal Tyr group;

(2) contacting the skin graft and the underlying tissue; and
(3) securing the skin graft to the underlying tissue, whereby incorporation of said skin graft into said underlying tissue is promoted. According to one embodiment the skin graft is an autologous graft. According to a preferred embodiment of the invention, the pharmacologically acceptable carrier includes a buffered saline solution. When the carrier includes buffered saline, the composition that includes the peptide can be applied in the applying step by soaking the skin graft. Alternatively, the pharmacologically acceptable carrier can include carboxymethyl cellulose. When the composition includes carboxymethyl cellulose and the peptide, it can be applied to the underlying tissue. According to another preferred embodiment, the composition which includes the buffered saline solution and the peptide can be applied to the underlying tissue. According to yet other preferred embodiments, the securing step can be accomplished by any of suturing, bandaging or applying a biological glue.

Still another aspect of the invention relates to a method of promoting incorporation of a skin graft into underlying tissue of a mammal. This method includes the steps of: (1) applying to either the skin graft or the underlying tissue an effective graft incorporation promoting amount of a composition which includes a pharmacologically acceptable carrier and a peptide having the general formula

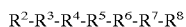

$$R^2\text{-}R^3\text{-}R^4\text{-}R^5\text{-}R^6\text{-}R^7\text{-}R^8$$

in which R² is selected from the group consisting of H, Arg, Lys, Ala, Orn, Ser(Ac), Sar, D-Arg and D-Lys;
R³ is selected from the group consisting of Val, Ala, Leu, norLeu, Ile, Gly, Pro, Aib, Acpc and Tyr;
R⁴ is selected from the group consisting of Tyr, Tyr (PO₃)₂, Thr, Ser, homoSer and azaTyr;
R⁵ is selected from the group consisting of Ile, Ala, Leu, norLeu, Val and Gly;
R⁶ is His, Arg or 6-NH₂-Phe;
R⁷ is Pro or Ala; and
R⁸ is selected from the group consisting of Ile, Phe, Phe(Br) and Tyr;

(2) contacting the skin graft and the underlying tissue; and
(3) securing the skin graft to the underlying tissue, whereby incorporation of said skin graft into said underlying tissue is promoted. According to one embodiment the skin graft is an autologous graft. According to a preferred embodiment of the invention, the pharmacologically acceptable carrier includes a buffered saline solution. When the carrier includes buffered saline, the composition that includes the peptide can be applied in the applying step by soaking the skin graft. Alternatively, the pharmacologically acceptable carrier can include carboxymethyl cellulose. When the composition includes carboxymethyl cellulose and the peptide, it can be applied to the underlying tissue. According to another preferred embodiment, the composition which includes the buffered saline solution and the peptide can be applied to the underlying tissue. According to yet other preferred embodiments, the securing step can be accomplished by any of suturing, bandaging or applying a biological glue.

BRIEF DESCRIPTION OF THE DRAWINGS

The invention may be better understood with reference to the accompanying drawings, in which:

FIG. 31 illustrates how the number of vascular channels at the graft interface depended on the concentration of AII in the soaking solution.

DETAILED DESCRIPTION OF THE PREFERRED EMBODIMENT

Figure 1:
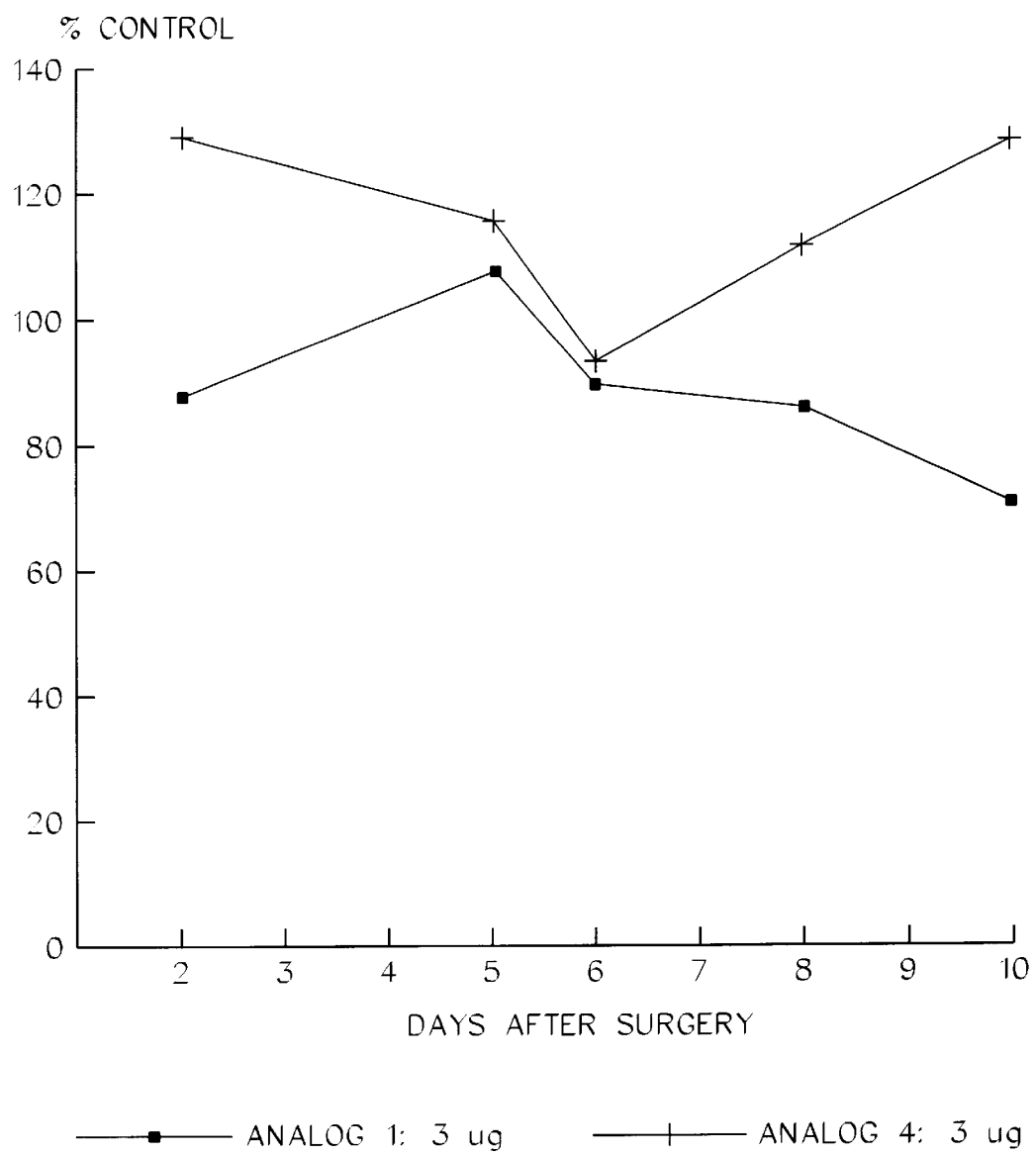
FIG. 1 illustrates the percent of control response in wound closure relative to a vehicle-treated control using analogs 1 and 4.

Pursuant to the present invention, healing of skin grafts in mammals is promoted through the use of a composition comprising an effective amount of at least one AT2 agonist, angiotensin I (AI) or analogs thereof, angiotensinogen or analogs thereof, AII, one active AII analog, fragment of AII or analog thereof. Additionally, precursors which are metabolized to these compounds also are contemplated for use in promoting healing of skin grafts according to the present invention, and so are intended to fall within the scope of the invention. Agonists of the AT2 receptor subtype are of benefit in wound repair but do not exhibit many of the side effects of AII, such as increases in blood pressure and thirst. The active agent is generally administered in a matrical or micellar solution or crystalloid composition and is effective in accelerating re-epithelialization and tissue repair even in very low concentrations.

As hereinafter defined, a preferred class of AT2 agonists for use in accordance with the present invention comprises AI or analogs thereof, angiotensinogen or analogs thereof, AII, AII analogs or active fragments thereof having p-NH$_2$-Phe in a position corresponding to position 6 of AII. In addition to peptide agents, various nonpeptidic agents (e.g., peptidomimetics) having the requisite AT2 agonist activity are further contemplated for use in accordance with the present invention.

The active AII analogs, fragments of AII and analogs thereof of particular interest in accordance with the present invention are characterized as comprising a sequence consisting of at least three contiguous amino acids of groups R$^1$–R$^8$ in the sequence of general formula I $$R^1\text{-}R^2\text{-}R^3\text{-}R^4\text{-}R^5\text{-}R^6\text{-}R^7\text{-}R^8 \tag{I}$$

in which R$^1$ and R$^2$ together form a group of formula

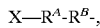

wherein X is H or a one to three peptide group and a peptide bond between R$^A$ and R$^B$ is labile to aminopeptidase A cleavage;
R$^3$ is selected from the group consisting of Val, Ala, Leu, norLeu, Ile, Gly, Pro, Aib, Acpc and Tyr;
R$^4$ is selected from the group consisting of Tyr, Tyr (PO$_3$)$_2$, Thr, Ser, homoSer and azaTyr;
R$^5$ is selected from the group consisting of Ile, Ala, Leu, norLeu, Val and Gly;

R$^6$ is His, Arg or 6-NH$_2$-Phe;
R$^7$ is Pro or Ala; and
R$^8$ is selected from the group consisting of Phe, Phe (Br), Ile and Tyr, excluding sequences including R$^4$ as a terminal Tyr group.

Compounds falling within the category of AT2 agonists useful in the practice of the invention include the AII analogs set forth above subject to the restriction that R$^6$ is p-NH$_2$-Phe.

In one class of preferred embodiments, R$^A$ is suitably selected from Asp, Glu, Asn, Acpc (1-aminocyclopentane carboxylic acid), Ala, Me$^2$Gly, Pro, Bet, Glu(NH$_2$), Gly, Asp(NH$_2$) and Suc. R$^B$ is suitably selected from Arg, Lys, Ala, Orn, Ser(Ac), Sar, D-Arg and D-Lys. Particularly preferred combinations for R$^A$ and R$^B$ are Asp-Arg, Asp-Lys, Glu-Arg and Glu-Lys.

Particularly preferred embodiments of this class include the following: AII, AIII or AII(2–8), Arg-Val-Tyr-Ile-His-Pro-Phe (SEQ ID NO:3); AII(3–8), also known as desl-AIII or AIV, Val-Tyr-Ile-His-Pro-Phe (SEQ ID NO:4); AII(1–7), Asp-Arg-Val-Tyr-Ile-His-Pro (SEQ ID NO:5); AII(2–7), Arg-Val-Tyr-Ile-His-Pro (SEQ ID NO:6); AII(3–7), Val-Tyr-Ile-His-Pro (SEQ ID NO:7); AII(5–8), Ile-His-Pro-Phe (SEQ ID NO:8); AII(1–6), Asp-Arg-Val-Tyr-Ile-His (SEQ ID NO:9); AII(1–5), Asp-Arg-Val-Tyr-Ile (SEQ ID NO:10); AII(1–4), Asp-Arg-Val-Tyr (SEQ ID NO:11); and AII(1–3); Asp-Arg-Val (SEQ ID NO:12). Other preferred embodiments include: Arg-norLeu-Tyr-Ile-His-Pro-Phe (SEQ ID NO:13) and Arg-Val-Tyr-norLeu-His-Pro-Phe (SEQ ID NO:14). Still another preferred embodiment encompassed within the scope of the invention is a peptide having the sequence Asp-Arg-Pro-Tyr-Ile-His-Pro-Phe (SEQ ID NO:32). AII(6–8), His-Pro-Phe (SEQ ID NO:15) and AII (4–8), Tyr-Ile-His-Pro-Phe (SEQ ID NO:16) were also tested and found not to be effective.

Another class of compounds of particular interest in accordance with the present invention are those of the general formula II $$R^2\text{-}R^3\text{-}R^4\text{-}R^5\text{-}R^6\text{-}R^7\text{-}R^8 \tag{II}$$

in which R$^2$ is selected from the group consisting of H, Arg, Lys, Ala, Orn, Ser(Ac), Sar, D-Arg and D-Lys;
R$^3$ is selected from the group consisting of Val, Ala, Leu, norLeu, Ile, Gly, Pro, Aib, Acpc and Tyr;
R$^4$ is selected from the group consisting of Tyr, Tyr(PO$_3$)$_2$, Thr, Ser, homoSer and azaTyr;
R$^5$ is selected from the group consisting of Ile, Ala, Leu, norLeu, Val and Gly;
R$^6$ is His, Arg or 6-NH$_2$-Phe;
R$^7$ is Pro or Ala; and
R$^8$ is selected from the group consisting of Ile, Phe, Phe(Br) and Tyr.

A particularly preferred subclass of the compounds of general formula II has the formula R$^2$-R$^3$-Tyr-R$^5$-His-Pro-Phe     (SEQ ID NO:17)

wherein R$^2$, R$^3$ and R$^5$ are as previously defined. Particularly preferred is angiotensin III (AIII) of the formula Arg-Val-Tyr-Ile-His-Pro-Phe (SEQ ID NO:3). Other preferred compounds include peptides having the structures Arg-Val-Tyr-Gly-His-Pro-Phe (SEQ ID NO:18) and Arg-Val-Tyr-Ala-His-Pro-Phe (SEQ ID NO:19). The fragment AII(4–8) was ineffective in repeated tests; this is believed to be due to the exposed tyrosine on the N terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviations for Amino Acids

| | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogs adopt either a gamma or a beta turn (Regoli et al. *Pharmacological Reviews* 26:69 (1974)). In general, it is believed that neutral side chains in positions $R^3$, $R^5$ and $R^7$ may be involved in maintaining the appropriate distance between the active groups in positions $R^4$, $R^6$ and $R^8$ primarily responsible for binding to receptors and/or intrinsic activity. Hydrophobic side chains in positions $R^3$, $R^5$ and $R^8$ may also play an important role on the whole conformation of the peptide and/or contribute to formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Ser and azaTyr. In this position, Tyr is particularly preferred as it may form a hydrogen bond with the receptor site capable of accepting a hydrogen from the phenolic hydroxyl (Regoli et al. (1974), supra).

In position $R^5$, an amino acid with a β aliphatic or alicyclic chain is particularly desirable. Therefore, while Gly is suitable in position $R^5$, it is preferred that the amino acid in this position be selected from Ile, Ala, Leu and Val.

In the AII analogs, fragments and analogs of fragments of particular interest in accordance with the present invention, $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogs of interest to receptors; therefore, Tyr and especially Phe are preferred for purposes of the present invention.

Analogs of particular interest include the following:

TABLE 2

Angiotensin II Analogs

| AII Analog Name | Amino Acid Sequence | Sequence Identifier |
|---|---|---|
| Analog 1 | Asp-Arg-Val-Tyr-Val-His-Pro-Phe | SEQ ID NO:20 |
| Analog 2 | Asn-Arg-Val-Tyr-Val-His-Pro-Phe | SEQ ID NO:21 |
| Analog 3 | Ala-Pro-Gly-Asp-Arg-Ile-Tyr-Val-His-Pro-Phe | SEQ ID NO:22 |
| Analog 5 | Glu-Arg-Val-Tyr-Ile-His-Pro-Phe | SEQ ID NO:23 |
| Analog 6 | Asp-Lys-Val-Tyr-Ile-His-Pro-Phe | SEQ ID NO:24 |
| Analog 7 | Asp-Arg-Ala-Tyr-Ile-His-Pro-Phe | SEQ ID NO:25 |
| Analog 8 | Asp-Arg-Val-Thr-Ile-His-Pro-Phe | SEQ ID NO:26 |
| Analog 9 | Asp-Arg-Val-Tyr-Leu-His-Pro-Phe | SEQ ID NO:27 |
| Analog 10 | Asp-Arg-Val-Tyr-Ile-Arg-Pro-Phe | SEQ ID NO:28 |
| Analog 11 | Asp-Arg-Val-Tyr-Ile-His-Ala-Phe | SEQ ID NO:29 |
| Analog 12 | Asp-Arg-Val-Tyr-Ile-His-Pro-Tyr | SEQ ID NO:30 |
| Analog 13 | Pro-Arg-Val-Tyr-Ile-His-Pro-Phe | SEQ ID NO:31 |
| Analog 14 | Asp-Arg-Pro-Tyr-Ile-His-Pro-Phe | SEQ ID NO:32 |
| Analog 15 | Asp-Arg-Val-Tyr($PO_3$)$_2$-Ile-His-Pro-Phe | SEQ ID NO:33 |

TABLE 2-continued

Angiotensin II Analogs

| AII Analog Name | Amino Acid Sequence | Sequence Identifier |
| --- | --- | --- |
| Analog 16 | Asp-Arg-norLeu-Tyr-Ile-His-Pro-Phe | SEQ ID NO:34 |
| Analog 17 | Asp-Arg-Val-Tyr-norLeu-His-Pro-Phe | SEQ ID NO:35 |
| Analog 18 | Asp-Arg-Val-homoSer-Tyr-Ile-His-Pro-Phe | SEQ ID NO:36 |

Angiotensin II is one of the most potent vasoconstrictors known, causing constriction of the small arteries that branch to form the capillaries, i.e., the arterioles. The biological formation of angiotensin is initiated by the action of renin on the plasma substrate angiotensinogen. The substance so formed is a decapeptide called angiotensin I which is converted to angiotensin II by the converting enzyme angiotensinase that removes the C-terminal His-Leu residues from angiotensin I.

Studies have shown that the vasoactive product of the renin-angiotensin system, AII increases the release of growth factors, mitogenesis, chemotaxis and the release of extracellular matrices of cultured cells that are involved in wound repair (Dzau et al. *J. Mol. Cell Cardiol.* 21 (Suppl. III):S7 (1989); Berk et al. *Hypertension* 13:305 (1989); Kawahara et al. *BBRC* 150:52 (1988); Naftilan et al. *J. Clin. Invest.* 83:1419 (1989); Taubman et al. *J. Biol. Chem.* 264:526 (1989); Nakahara et al. *BBRC* 184:811–8 (1992); Stouffer et al. *Circ. Res.* 70:820 (1992); Wolf et al. *Am. J. Pathol.* 140:95 (1992); Bell et al. *Am. J. Pathol.* 137:7 (1990)). In addition, AII was shown to be angiogenic in rabbit corneal eye and chick chorioallantoic membrane models (Fernandez et al. *J. Lab. Clin. Med.* 105:141 (1985); LeNoble et al. *Eur. J. Pharmacol.* 195:305 (1991)). Therefore, AII may accelerate wound repair through increased neovascularization, growth factor release, reepithelialization and production of extracellular matrix. Through an increase in the flow of blood and nutrients to an injured tissue, AII may increase the rate of wound repair. AII may also accelerate wound repair through the generation of growth factors at the site of injury. Exogenous addition of growth factors has been shown to accelerate wound repair through a variety of mechanisms (Grotendorst et al. *J. Clin. Invest.* 76:2323 (1985); Mustoe et al. *Science* 237:1333 (1987); Pierce et al. *J. Exp. Med.* 167:974 (1988); Lynch et al. *J. Clin. Invest.* 84:640 (1989); Greenhalgh et al. *Am. J. Pathol.* 136:1235 (1990)). Recent studies showed that AII increased neointima formation in the carotid artery and aorta after injury (Powell et al. *Science* 245:186 (1989); Powell et al. *J. Cardiovasc. Pharmacol.* 16 (suppl 4):S42–9 (1991); Capron et al. *J. Cardiovasc. Pharmacol.* 18:207 (1991); Osterriedes et al. *Hypertension* 18: Suppl 1160–64 (1991); Daemen et al. *Circ. Res.* 68:450 (1991)). As a result of these observations, studies were conducted to determine the mechanism by which endogenous AII may induce intimal hyperplasia. AII was shown to act as a mitogen for smooth muscle cells, fibroblasts and endothelial cells (Schelling et al. *J. Cell. Physiol.* 98:503 (1979); Campbell-Boswell *Exp. Mol. Pathol.* 35:265 (1981); Emmett et al. *J. Cell. Biol.* 103:171 (1986); Paquet et al. *J. Hypertens.* 8:565 (1990); Dzau et al., supra). AII also increased the protein content and size of vascular smooth muscle cells (Berk et al. (1989), supra; Geisterfer et al. *Cir. Res.* 62:749 (1988)). Studies showed that AII increases the release of growth factors of various types, including PDGF, heparin-binding EGF and transforming growth factorβ (TGFβ), and growth-related proto-oncogenes from smooth muscle cells, endothelial cells and cardiac fibroblasts (Kawahara et al. (1988), supra; Naftilan, A.J. *J. Cardiovas. Pharmacol.* 20: S37 (1992); Naftilan et al. (1989), supra; Taubman et al. (1989), supra; Nakahara et al. (1992), supra; Temizer et al. (1992), supra; Gibbons et al. *J. Clin. Invest.* 90:456 (1992); Bell et al. *J. Clin. Invest.* 89:315 (1992); Stouffer et al. (1992), supra). The hypertrophy of vascular smooth muscle cells by AII was mediated through PDGF (Berk et al. *J. Cell. Physiol.* 154:368 (1993)).

Therefore, it is conceivable that AII acts to accelerate wound repair through increasing the levels of these growth factors in the wound tissue. Additionally, AII was shown to stimulate collagen synthesis thereby suggesting a role for this factor in extracellular matrix formation (Wolf et al. *Cell. Reg.* 2:219 (1991); Wolf et al. (1992), supra; Zhou et al. *FASEB. J.* 6: A1914 (1992)). Wound repair also involves chemotaxis of the necessary cell types into the wound bed. AII was also shown to induce the migration of endothelial cells and smooth muscle cells in vitro (Bell et al. (1990), supra).

Recent studies also have indicated that expression of AII receptors is altered during the process of wound repair (Viswanathan et al. *Peptides* 13:783 (1992); Kimura et al. *BBRC* 187:1083 (1992)). These changes, along with evidence of an increase in the local production of AII at the site of repair suggests that AII may play a key role in the process of wound repair.

The actions of AII that may be involved in wound repair have recently been reviewed (Phillips et al. Angiotensin receptor stimulation of transforming growth factor-β in rat skin and wound healing. In *Angiotensin Receptors* (ed J M Saavedra and PBMWM Timmermans), Plenum Press, New York, N.Y., pp 377–396 (1994)). In the majority of studies reported, these effects have been shown to be mediated by the AT1 receptor.

The blood pressure effects (and most other effects, such as aldosterone secretion and increased thirst) of AII are mediated by the type 1 receptor (AT1 receptor) (Wong, PC Angiotensin antagonists in models of hypertension. In: *Angiotensin Receptors* (JM Saavedra and PBMWM Timmermans), Plenum Press New York, N.Y. pp 319–336 (1994); MacKenzie et al. *J. Hypertension* 12 (Suppl 9): S11–S16 (1994); Gupta et al. *Hypertension* 25:443 (1995); Llorens-Cortes et al. *Hypertension* 24:538 (1994); Wong et al. *Eur J. Pharmacol* 220:267 (1992)). This conclusion is based upon the blocking of the action of AII by receptor subtype specific antagonists.

The effects of AII and AII antagonists have been examined in two experimental models of vascular injury and repair. Studies have been mixed with regards to the contribution of AT2 to hyperplasia of vessels after balloon injury to the vasculature. In the rat carotid artery, the majority of receptors are AT2 (Pratt et al. *Hypertension* 20:432 (1992)). By contrast, neointimal cells of the injured rat thoracic aorta express predominately AT1 receptors. (Viswanathan et al. *J. Clin Invest* 90:1707 (1992)). Treatment of rats with PD 123319 (AT2 specific antagonist) reduced intimal hyperplasia by 73% while losartan (AT1 specific antagonist) decreased intimal area by 95% (Pratt et al. (1992), supra). In a similar model, CGP 42112 (an AT2 antagonist) infused perivascularly for 14 days prevented neointimal formation, but low doses of losartan were ineffective (Janiak et al. *Hypertension* 20:737 (1992)). In other studies, losartan at higher doses was found to be effective (Forney Prescott et al. *Am J Pathol* 139:1291 (1991); Kauffman et al. *Life Sci* 49:223 (1991)). Therefore, it is conceivable that both receptor subtypes may play a role in the formation of vascular lesions after balloon injury.

During experimental wound healing in young animals, the expression of AII receptors increase significantly in a localized band of tissue within the superficial dermis of the skin surrounding the wound. Most of this increase is due to AT2 receptors (Viswanathan et al. *Peptides* 13:783 (1992); Kimura et al. *Biochem Biophys Res Commun* 187:1083 (1992)). These results, and the results disclosed hereinbelow, were obtained using procedures that employed adult rats as experimental animals. AT1 receptors are altered after formation of incisional wounds in adult rats. The experimental designs in these latter studies do not distinguish between the dermis and other portions of the wound.

It has been observed that AII and AIII have quite different biological activities in several respects. For example, AII showed a biphasic effect on evoked neuronal norepinephrine release (an earlier decrease followed by a later increase), while increasing spontaneous norepinephrine release only after 12 minutes; AIII showed a biphasic effect on both evoked and spontaneous neuronal norepinephrine release (Vatta et al. *Can. J. Physiol. Pharmacol.* 70:821 (1992)). Moreover, AII and AIII show differential influences on the baroreceptor-heart-reflex: AII enhances the sensitivity of the reflex, whereas AIII impairs it (Brattstrom et al. *Progress in Brain Research* 91:75 (1992)). Surprisingly, notwithstanding these significant differences in biological activity between AII and AIII, AIII and particular analogs thereof are useful in accelerating wound healing.

Many studies have focused on AII(1–7) to evaluate its activity. Many of the effects of AII(1–7) are attributed to acting through the AT2 receptor. However, this is not consistent and depends upon the tissue examined.

AII(1–7) does not have many of the effects of AII. AII(1–7) lacks pressor activity or has very mild (effective at 10,000–100,000 times the dose of AII) effects on blood pressure depending upon the model tested and route of administration. In fact, AII(1–7) has a depressor effect on blood pressure that may be mediated through prostanoid synthesis. In addition, in contrast to the effects of AII, AII(1–7) does not cause catecholamine release and aldosterone release and is not dipsogenic (Webb et al. *Peptides* 13:499 (1992); Cheng et al. *Am. J. Physiol.* 266: H2247–H2255 (1994); Moriguchi et al. *Am. J. Physiol.* 267: $R^{786}$–$R^{791}$ (1994); Schiavone et al. *J. Cardiovascular Pharmacol.* 16(Suppl. 4):S19–S24 (1990); Ferrario et al. *Hypertension* 19(suppl. III):III-126–III-133 (1991)).

In one report, AII(1–7) is a weak pressor that requires about 10,000 times more AII(1–7) than AII to get a comparable response (Benter et al. *Peptides* 14:679 (1993)). In this system, AII(1–7) had a long depressor effect that was dose dependent. AII(3–7) had less of a pressor effect than AII(1–7), but had no depressor effect. It is also noted that AII(1–7), AII(2–7) and AII(3–7) may affect the dopamine system and memory (suggesting a psychoactive effect).

In several systems, the actions of AII(1–7) are quite distinct from AII. AII stimulates choline production in rat mesangial cells through the AT 1 receptor; AII(1–7) and AII(1–6) has very weak effects on this parameter (Pfeilschifter et al. *Eur. J. Pharmacol.* 225:57 (1992)).

In porcine aortic endothelial cells, AI and AII(1–7) stimulated the release of prostaglandin E2 and I2, but AII did not have this effect (Jaiswal et al. *Hypertension* 19 (Suppl II):11-49-II-55 (1992)). AII is able to stimulate the release of prostanoids in other cells types and in intact blood vessels but not human or porcine endothelial cells. The effect on endothelial cells was through a receptor distinct from AT1 and AT2.

In rat glomerulus preparations, AII inhibited the formation of cAMP in response to histamine, serotonin and parathyroid hormone through the AT1 receptor (Edwards et al. *J. Pharmacol. Exper. Ther.* 266:506 (1993)). AII(1–7) did not have this effect.

In porcine vascular smooth muscle cells and human astrocytes, AII and AI(1–7) increases prostaglandin release; only angiotensin II increases the release of intracellular $Ca^{2+}$ (Jaiswal et al. *J. Pharmacol. and Exp. Therapeutic* 265:664 (1993); Jaiswal et al. *Hypertension* 17:1115 (1991)).

AII(1–7) dilates porcine coronary artery rings, perhaps through nitric oxide (Porsti et al. *Br. J. Pharmacol.* 111:652 (1994)). This was not observed with AII, AIII or AII(3–8). This effect was not attenuated by antagonists of AT1 or AT2 receptors.

AII causes depolarization of rat isolated nodose ganglion; AII(1–7) does not (Widdop et al. *Clin. and Exper. Hyper-Theory and Practice* A14:597 (1992)). Indeed, AII(1–7) may have novel actions on brain function (Schiavone et al. *J. Cardiovascular Pharmacol.* 16(Suppl 4):S19–S24 (1990)).

There are activities that AII(1–7) shares with AII, such as release of vasopressin and modulation of phospholipase A2 activity in proximal tubule cells (Andreatta-Van Leyen et al. *Kidney International* 44:932 (1993); Moriguchi et al. *Am. J. Physiol.* 267: R786–R791 (1994); Ferrario et al. *Hypertension* 19(suppl III):III-126-III-133 (1991)). These activities, however, are likely not involved in wound repair.

The effects of other fragments of AII have been studied in very few instances. Most neurons in the paraventricular nucleus are excited by AII(1–7), AII and AIII, but AII(1–7) is weaker in this effect; in many neurons, AII(2–7) was inactive (Ambuhl et al. *Regulatory Peptides* 38:111 (1992)). AII injected in the lateral cerebral ventricle increased the motility, stereotypy and learning of conditioned avoidance responses; AII(1–6) and AII(2–6) were not active in these psychotropic activities (Holy et al. *Polish J. Pharmacol.* 45:31 (1993)).

AII(4–8), AII(5–8) and AII(1–4) showed only a slight effect on water intake when injected into the anterior diencephalon in the rat, and AII(1–7) was completely inactive (Fitzsimmons *J. Physiol.* 214:295 (1971)). Intracerebroventricular infusion of AII fragments (AII(4–8) and AII(5–8)) in the rat produced a minimal effect on blood pressure even when given at concentrations 1,000 times higher than that of AII that increased blood pressure (Wright et al. *Am. J. Physiol.* 257: R1551 (1989)). In both of these studies, the fragments were injected directly into the brain; this is highly artificial and does not allow for systemic metabolism.

According to the method of the invention, AII, an active AII analog, AII fragment or analog thereof in accordance with the present invention is applied to wound tissue comprising a skin graft in amounts sufficient to increase the healing rate of tissue. These compounds can significantly accelerate the rate of healing at nanomolar levels in vivo. For any given active agent, the optimum concentration for a given formulation may readily be determined empirically. In general, an amount of active agent suitable for use in accordance with the present invention ranges from about 0.001 μg to about 10 mg per kilogram body weight, or about 1 ng to 100 μg/cm² of wound area.

The compounds of the invention may be applied in a variety of solutions. Suitable solutions for use in accordance with the present invention are sterile, dissolve sufficient amounts of the peptide, and are not harmful to wound tissue. In this regard, the compounds of the present invention are very stable but are hydrolyzed by strong acids and bases. The compounds of the present invention are soluble in organic solvents and in aqueous solutions at pH 5–8.

Any type of application means may be employed which permits the influx of the active agents into the tissue over a period of time. For example, an aqueous solution could be applied to the wound tissue through a gauze bandage or strip, or such a solution could be formulated so that a timed perfusion may be obtained (using, e.g., liposomes, ointments, micelles, etc.). Methods for the production of these formulations with the compounds of the present invention are apparent to those of ordinary skill in the art. The particular concentration of active agent employed is not critical, as the tissue-repairing effect is present even when the compounds are present in nanomolar quantities.

Preferably, a matrical, micellar or crystalloid solution is employed with the active agent present in a concentration of at least 0.01 μg/ml. A particular matrical solution which has been used to advantage in the described Examples is a semi-solid polyethylene glycol polymer sold under the trademark HYDRON by Hydro Med Sciences (New Brunswick, N.J.). Another preferred solution is a micellar solution sold under the trade name PLURONICS F108 by BASF (Ludwigshafen, Germany). Under room temperature conditions, this solution is a liquid, but when applied to warm tissue the solution forms a gel which permits the infusion of active agent into the wound tissue for a period of several days. Other preferred formulations include carboxymethyl cellulose preparations (as used in the Example herein), crystalloid preparations (e.g., saline, Ringer's lactate solution, Ringer's lactate solution with 5% dextrose, phosphate-buffered saline, etc.), viscoelastics, polyethylene glycols, polypropylene glycols, glues or tissue adhesives (such as fibrin glues, albumin glues, thrombogen or collagen sealants) and wound dressings (e.g., bandages, etc.).

The healing effects of the compounds of the present invention may be provided in a variety of instances. The solution may be applied topically to surface wound tissue in the treatment of ulcers, lesions, injuries, diabetic ulcers, bums, trauma, stasis ulcers, periodontal conditions, lacerations and other conditions. In addition, intraperitoneal wound tissue such as that resulting from invasive surgery may be treated with a composition in accordance with the present invention to accelerate healing. For example, following the surgical removal of a colon section or other tissue, the surgical plane may be coated with a solution of active agent prior to closing the surgical site in order to accelerate internal capillary perfusion and healing. In addition, the rate of localized healing may be increased by the subdermal administration of active agent by injection or otherwise.

The invention may be better understood with reference to the accompanying Examples, which are intended for purposes of illustration only and should not be construed as limiting the scope of the invention, as defined in the claims appended hereto. Several Examples presented below establish the general utility of the compositions disclosed herein for accelerating wound healing. Subsequent Examples disclose how the compositions disclosed herein can be used to promote healing of skin grafts.

Example 1 describes the methods used to confirm that healing of full thickness wounds was accelerated by administration of a medicament comprising AII analogs.

EXAMPLE 1

Angiotensin II Analogs Accelerate Healing of Full Thickness Wounds

Twelve week old male Sprague Dawley rats were obtained from Simonsen Laboratories (Gilroy, Calif.). On the day of surgery rats received intramuscular ketamine/rompum anesthesia prior to preparation for surgery. The rats were shaved and scrubbed with betadine. Four 2×2 cm full thickness dermal wounds were created on the dorsal surface of each rat. Following excision of the skin, the size of the wound was outlined on a glass slide to establish the baseline wound size. The medicament was administered in 100 μl of a solution comprising 10% HYDRON, 1% polyethylene glycol (MW 400) and 60% ethanol. Test materials were administered in a randomized fashion. AII materials were tested at 3 μg/wound, with analogs 2 and 3 also being evaluated at 10 μg/wound. Control wounds were treated with vehicle only. After administration of the test materials, the rats were bandaged and allowed to recover from anesthesia. At days 2, 5, 6, 8 and 10 the area of each skin wound was measured under methoxyflurane anesthesia (commercially available as METOFANE from Pittman-Moore, Mundelein, Ill.) The area of the wound was determined by: (1) tracing the wound shape onto graph paper (1×1 mm squares); (2) cutting out the shape; (3) weighing the paper and comparing the weight with a 2×2 cm paper cutout; and (4) counting the number of squares on the graph paper.

Figure 2:
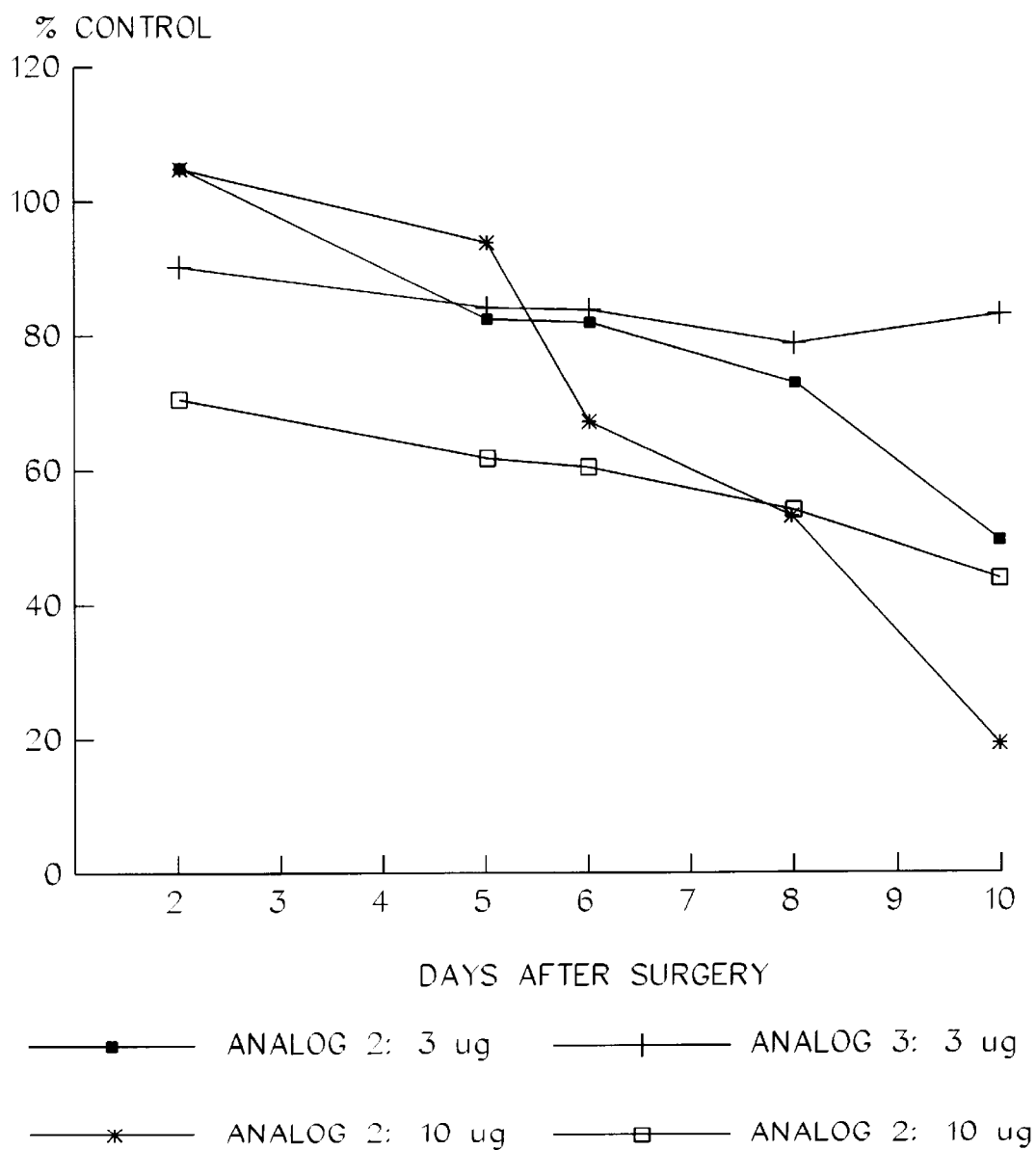
FIG. 2 illustrates the percent of control response in wound closure relative to a vehicle-treated control using analogs 2 and 3 at two different dosages.
Figure 3:
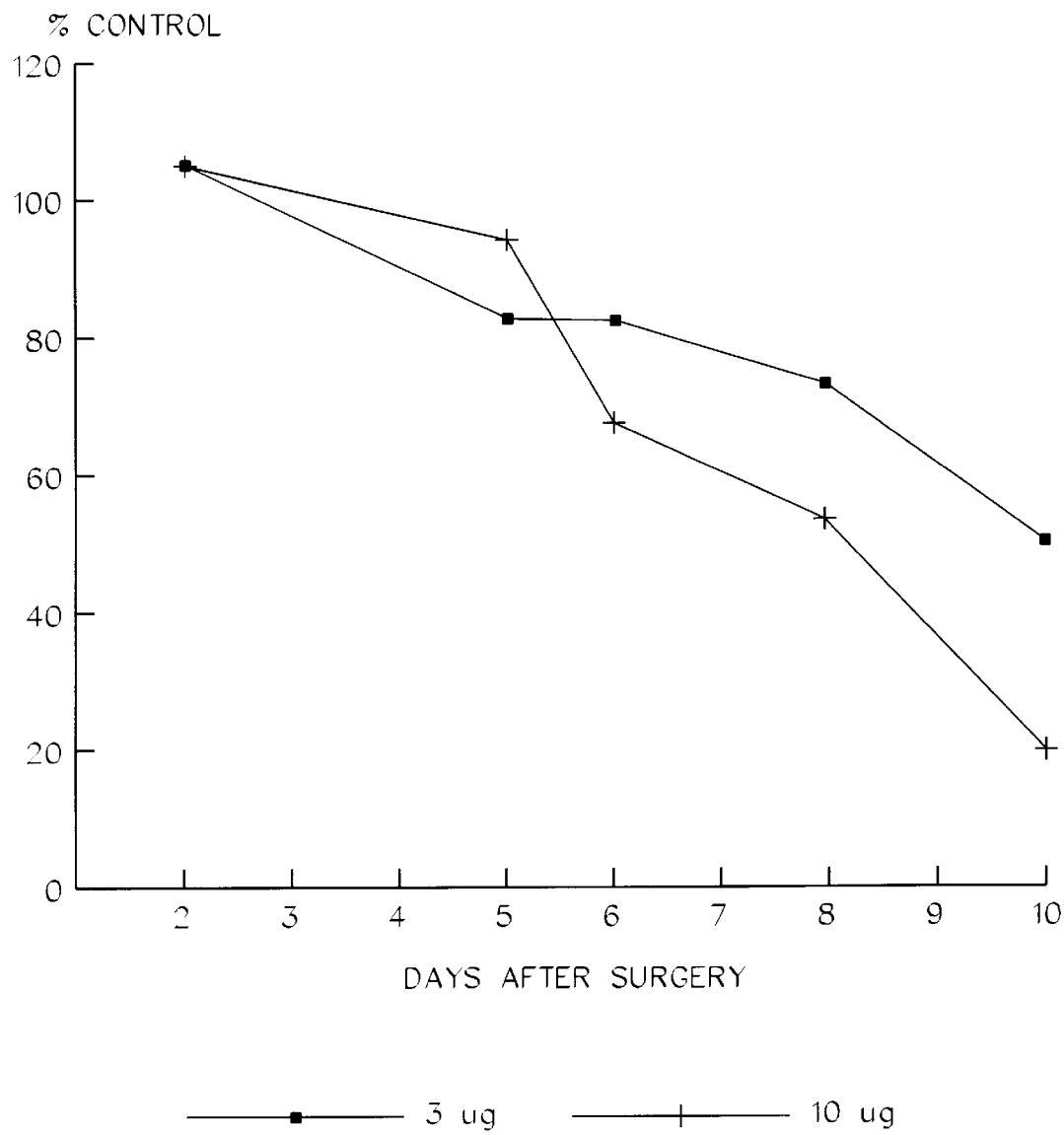
FIG. 3 illustrates the percent of control response in wound closure relative to a vehicle-treated control using analog 2.

As illustrated in the drawings, full thickness wound closure was substantially accelerated relative to the controls when test wounds were treated with analogs I (FIG. 1), 2 and 3 (FIG. 2) in accordance with general formula I. Results presented in the figures illustrate the percent increase in wound closure relative to a vehicle-treated control. Surprisingly, administration of analog 4 (Sar-Arg-Val-Tyr-Ile-His-Pro-Phe (SEQ ID NO:37)) which is outside the scope of general formula I because $R^A$ is Sar, did not accelerate wound repair (FIG. 1). This analog has been reported to have full affinity and activity for angiotensin II receptor, but is resistant to cleavage by aminopeptidase (Mendelsohn et al. *Proc. Nat. Acad. Sci. USA* 81:1575 (1984); Israel et al. *Brain Res.* 322:341 (1984); Harding et al. *Brain Res.* 424:299 (1987)). FIG. 3 illustrates that the 10 μg dosage accelerated wound healing more effectively than the 3 μg dosage.

Example 2 provides a systematic illustration for how each of the eight amino acid positions of the AII molecule can be substituted by a different amino acid to result in a compound having therapeutic utility in accordance with the methods described above.

EXAMPLE 2

Angiotensin Analogs Substituted at Each of Eight Positions Retain Wound Healing Activity Twelve week old female Sprague Dawley rats were obtained from Simonsen Laboratories (Gilroy, Calif.). On the day of surgery rats received intramuscular ketamine/rompum anesthesia prior to preparation for surgery. The rats were shaved and scrubbed with betadine. Two 1.5×1.5 cm full thickness dermal wounds were created on the dorsal surface of each rat. Following excision of the skin, the size of the wound was outlined on a glass slide to establish the baseline wound size. The medicament was administered in 100 μl of a solution comprising 10% HYDRON, 1% polyethylene glycol (MW 400) and 60% ethanol. Test materials were administered in a randomized fashion with all materials being tested at 10 μg/wound. Control wounds were treated with vehicle only. After administration of the test materials, the rats were bandaged and allowed to recover from anesthesia. At days 2, 5, 7 and 9 the area of the skin wounds was measured under methoxyflurane anesthesia. The area of the wound was determined by (1) tracing the wound shape onto graph paper (1×1 mm squares); (2) cutting out the shape; (3) weighing the paper and comparing the weight with a 1.5×1.5 cm paper cutout; and (4) counting the number of squares on the graph paper. In addition, on days 2, 5 and 7 the area of granulation tissue was determined for the animals administered with analogs 5–10.

Figure 4:
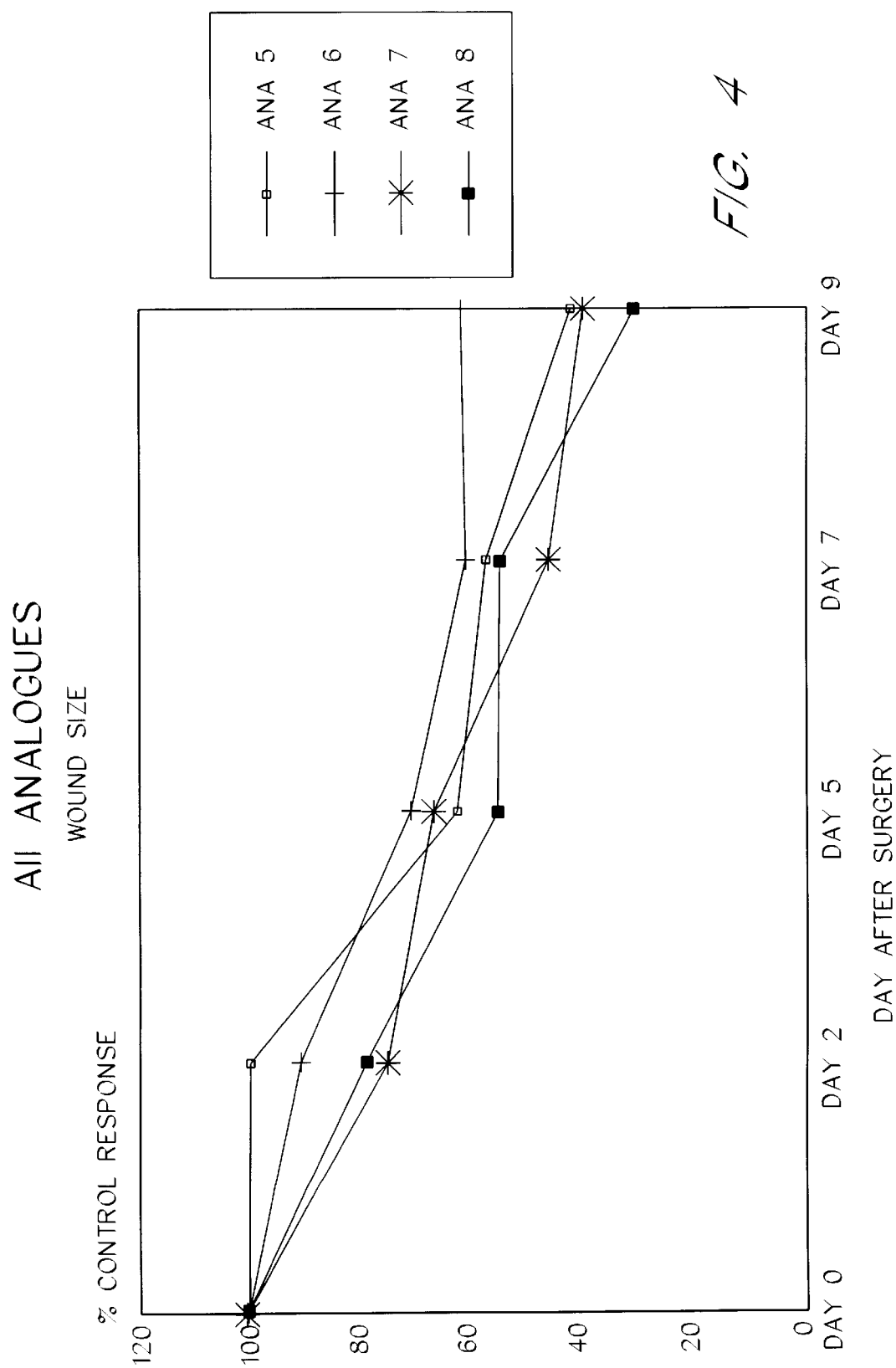
FIG. 4 illustrates the percent of control response in wound closure relative to a vehicle-treated control using analogs 5–8.
Figure 5:
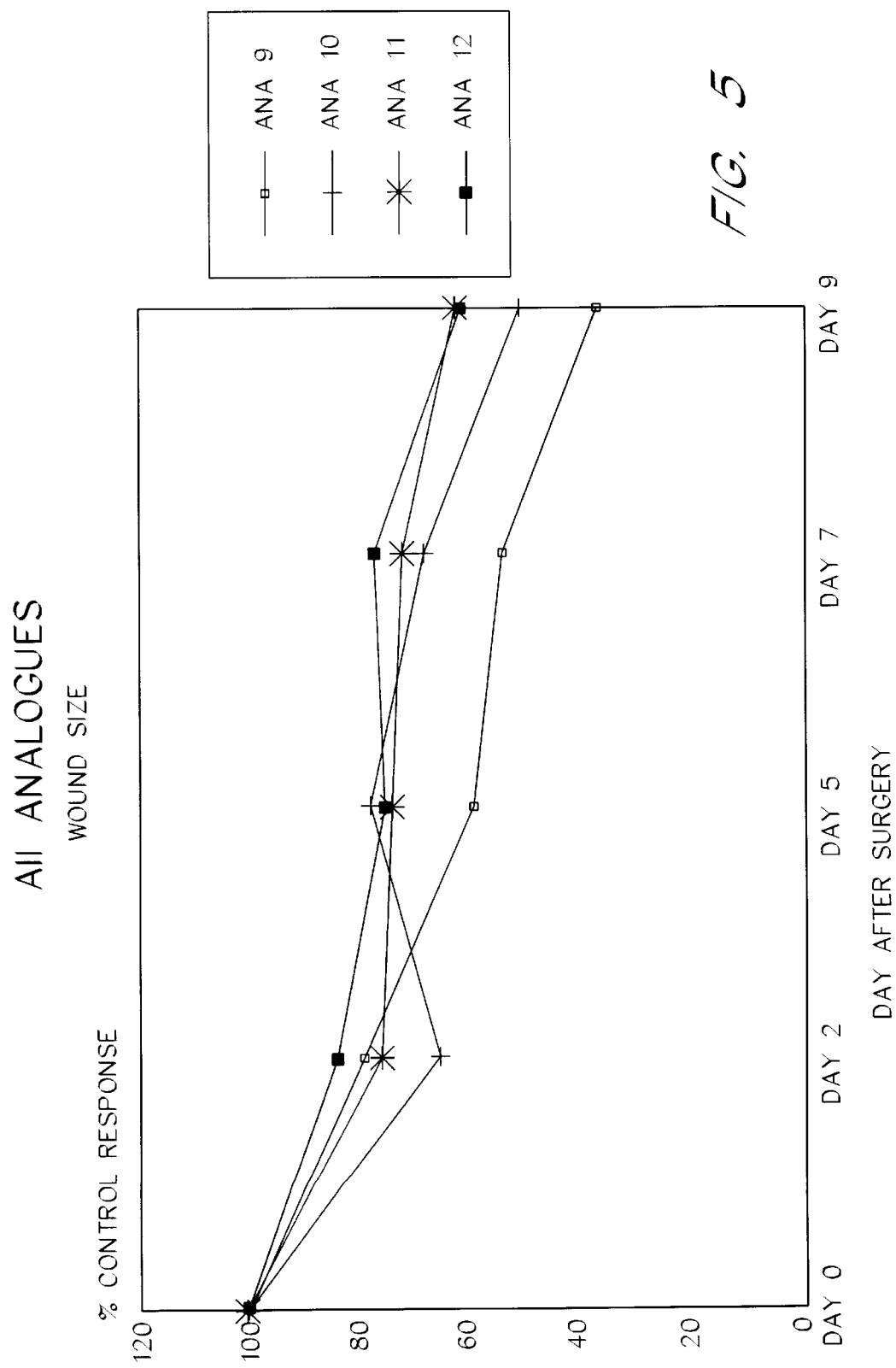
FIG. 5 illustrates the percent of control response in wound closure relative to a vehicle-treated control using analogs 9–12.
Figure 6:
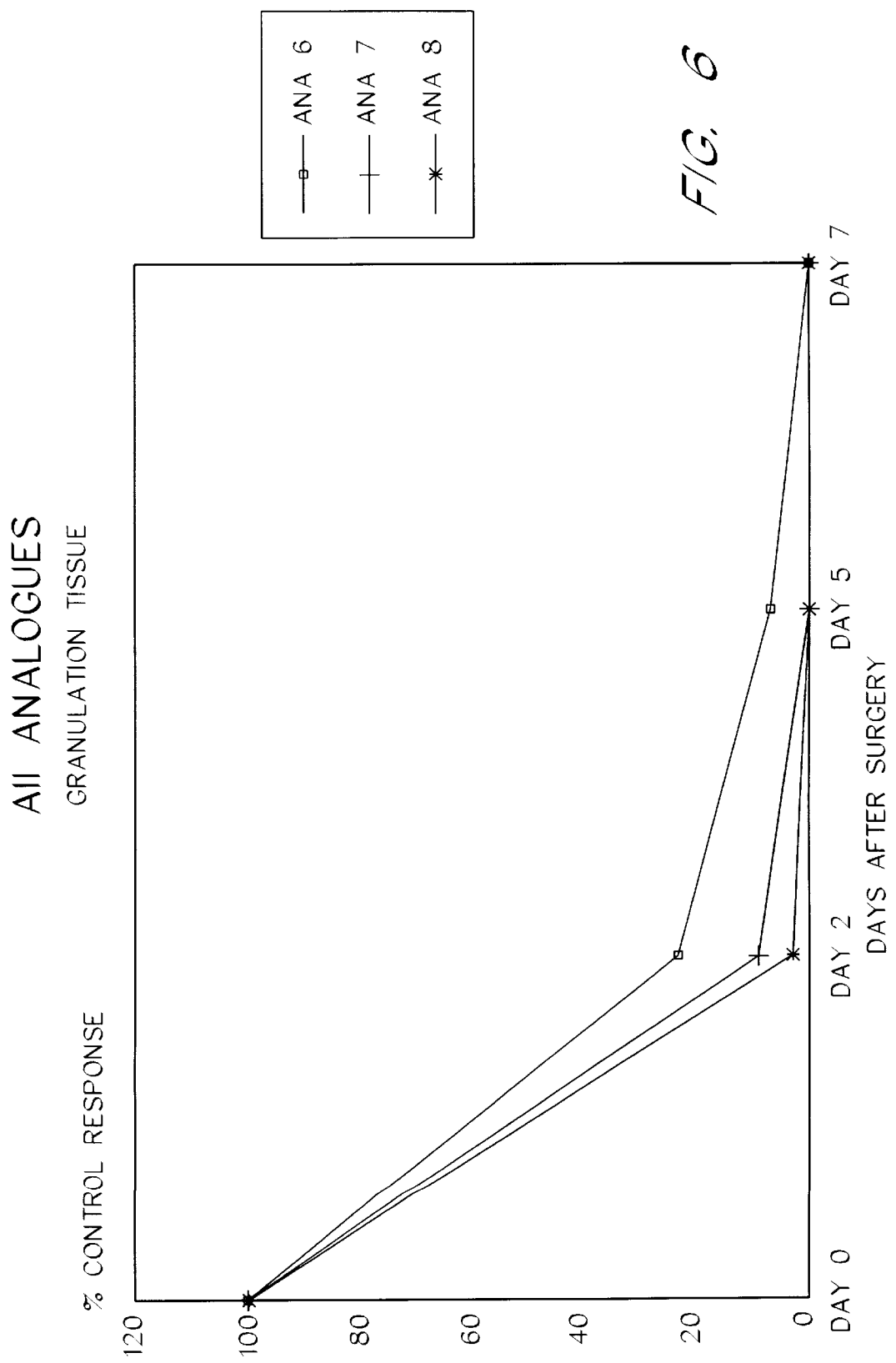
FIG. 6 illustrates the percent of control response in formation of granulation tissue using analogs 6–8.
Figure 7:
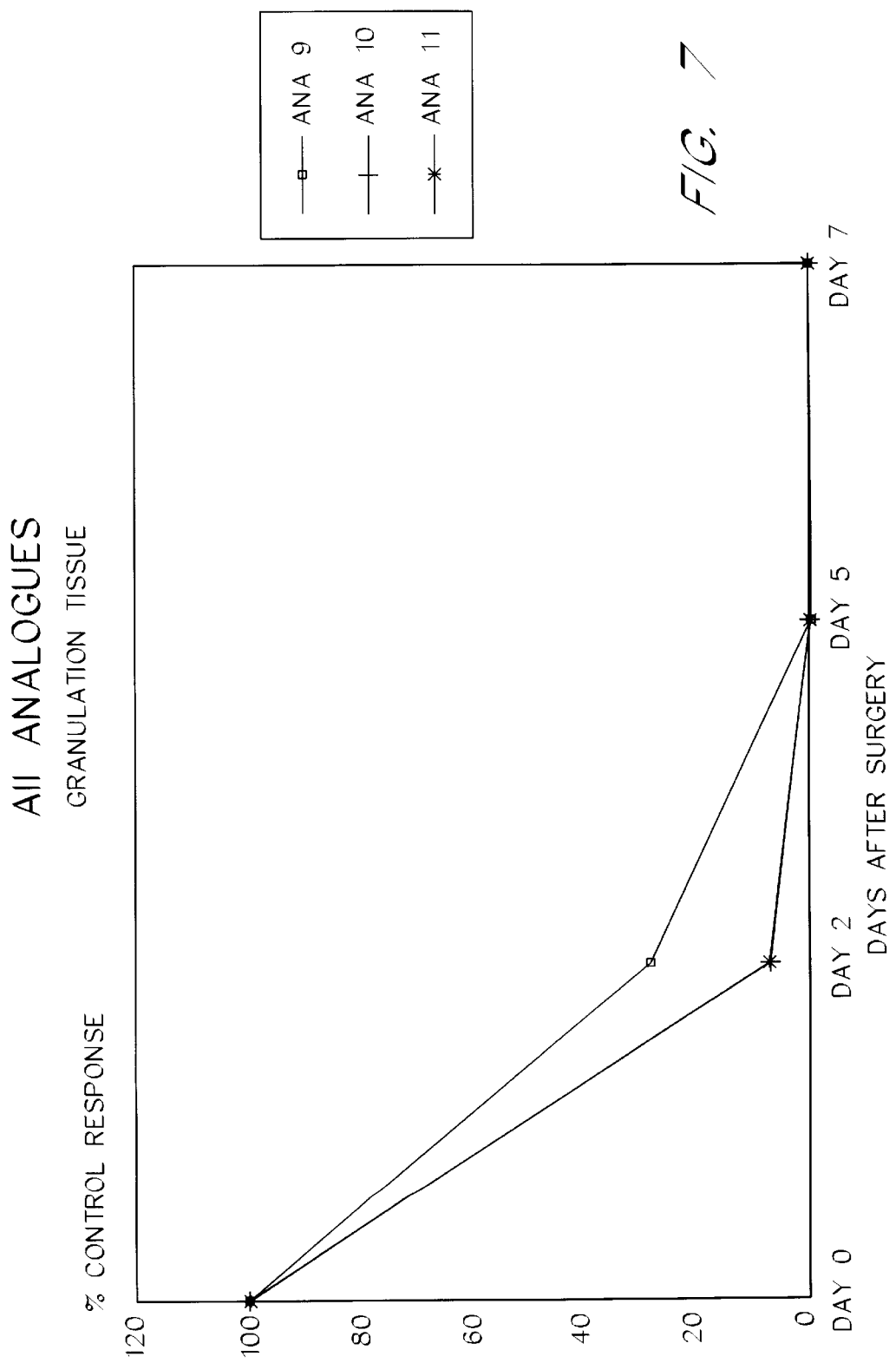
FIG. 7 illustrates the percent of control response in formation of granulation tissue using analogs 9–11.

As illustrated in FIGS. 4–7, wound closure was substantially accelerated relative to the control wounds when the test wounds were treated with analogs 4–11 in accordance with general Formula I. FIGS. 4 and 5 illustrate the percent of control response in wound closure relative to a vehicle-treated control. In every case, administration of one of the analogs accelerated the closure of the wound after surgery. FIGS. 6 and 7 illustrate the percent of control response in formation of granulation tissue. Again, in every case administration of one of the analogs accelerated the formation of granulation tissue compared to administration of vehicle alone. These results show how AII analogs having amino acid sequences in accordance with the invention can be used to accelerate wound healing.

Example 3 describes the methods that were used to demonstrate that AIII accelerated the healing of full thickness dermal wounds.

EXAMPLE 3

Angiotensin III Accelerates Healing of Full Thickness Dermal Wounds

Twelve week old male Sprague Dawley rats were obtained from Simonsen Laboratories (Gilroy, Calif.). On the date of surgery, rats received intramuscular ketamine/rompum anesthesia prior to preparation for surgery. The rats were shaved and scrubbed with betadine. Four 2×2 cm full thickness dermal wounds were created on the dorsal surface of the rat. Following excision of the skin, the size of the wound was outlined on a glass slide to establish the baseline wound size. The medicament was administered in 100 μl of a solution comprising 10% HYDRON, 1% polyethylene glycol (MW 400) and 60% ethanol. Test materials were administered in a randomized fashion. AIII was evaluated at 3 and 10 μg/wound. Controls were treated with vehicle only. After administration of the materials, the rats were bandaged and allowed to recover from anesthesia. At days 2, 5, 6, 8 and 10 the area of the skin wounds were measured under methoxyflurane anesthesia. The area of the wound was determined by: (1) tracing the wound shape onto graph paper (1×1 mm squares); (2) cutting out the shape; (3) weighing the paper and comparing the weight with a 2×2 cm paper cutout; and (4) counting the number of squares.

Figure 8:
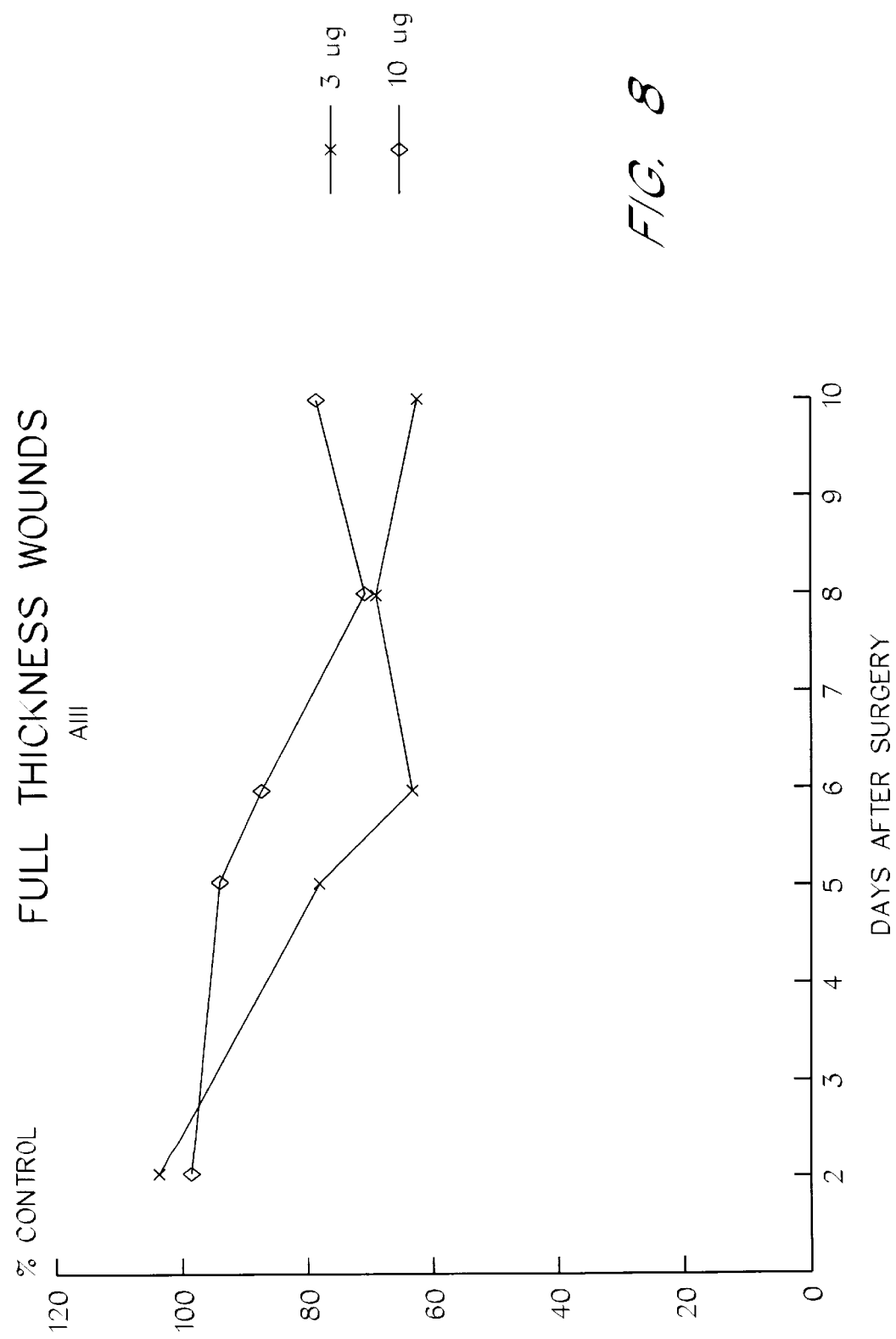
FIG. 8 illustrates the percent increase in wound closure relative to a vehicle-treated control using AIII.

As illustrated in FIG. 8, wound closure was substantially accelerated relative to the control animals when the test animals were treated with AIII, at both the 3 μg and the 10 μg dosages. The results presented in FIG. 8 illustrate the percent increase in wound closure relative to a vehicle-treated control.

Example 4 describes the methods used to demonstrate that AIII analogs also accelerated the healing of full thickness dermal wounds.

EXAMPLE 4

Angiotensin III Analogs Accelerate Healing of Full Thickness Dermal Wounds

Twelve week old female Sprague Dawley rats were obtained from Simonsen Laboratories (Gilroy, Calif.), and prepared for surgery as described in Example 3. Two 1.5×1.5 cm full thickness dermal wounds were created on the dorsal surface of each rat. Following excision of the skin, the size of the wound was outlined on a glass slide to establish the baseline wound size. The medicament was administered in 100 μl of a solution comprising 10% HYDRON, 1% polyethylene glycol (MW 400) and 60% ethanol. Test materials were administered in a randomized fashion with all materials being tested at 10 μg/wound. Control wounds were treated with vehicle only. After administration of the materials, the rats were bandaged and allowed to recover from anesthesia. At days 2–3, 5, 7–8 and 9–10 the area of the skin wounds were measured (for analogs 1A and 2–8 as shown in Table 3) under methoxyflurane anesthesia. The area of the wound was determined by: (1) tracing the wound shape onto graph paper (1×1 mm squares); (2) cutting out the shape; (3) weighing the paper and comparing the weight with a 1.5×1.5 cm paper cutout; and (4) counting the number of squares. In addition, on days 2–3, 5 and 8, the area of granulation tissue was similarly determined (for analogs 1A, 1B and 2–7). The analogs employed in these procedures had the structures presented in Table 3.

TABLE 3

Angiotensin III Analogs

| AII Analog Name | Amino Acid Sequence | Sequence Identifier |
| --- | --- | --- |
| Analog 1A | Arg-Val-Tyr-Ile-His-Pro-Ile | SEQ ID NO:38 |
| Analog 1B | Arg-Val-Tyr-Val-His-Pro-Phe | SEQ ID NO:39 |
| Analog 2 | Lys-Val-Tyr-Ile-His-Pro-Phe | SEQ ID NO:40 |
| Analog 3 | Arg-Ala-Tyr-Ile-His-Pro-Phe | SEQ ID NO:41 |

TABLE 3-continued

Angiotensin III Analogs

| AII Analog Name | Amino Acid Sequence | Sequence Identifier |
|---|---|---|
| Analog 4 | Arg-Val-Thr-Ile-His-Pro-Phe | SEQ ID NO:42 |
| Analog 5 | Arg-Val-Tyr-Leu-His-Pro-Phe | SEQ ID NO:43 |
| Analog 6 | Arg-Val-Tyr-Ile-Arg-Pro-Phe | SEQ ID NO:44 |
| Analog 7 | Arg-Val-Tyr-Ile-His-Ala-Phe | SEQ ID NO:45 |
| Analog 8 | Arg-Val-Tyr-Ile-His-Pro-Tyr | SEQ ID NO:46 |

Figure 9:
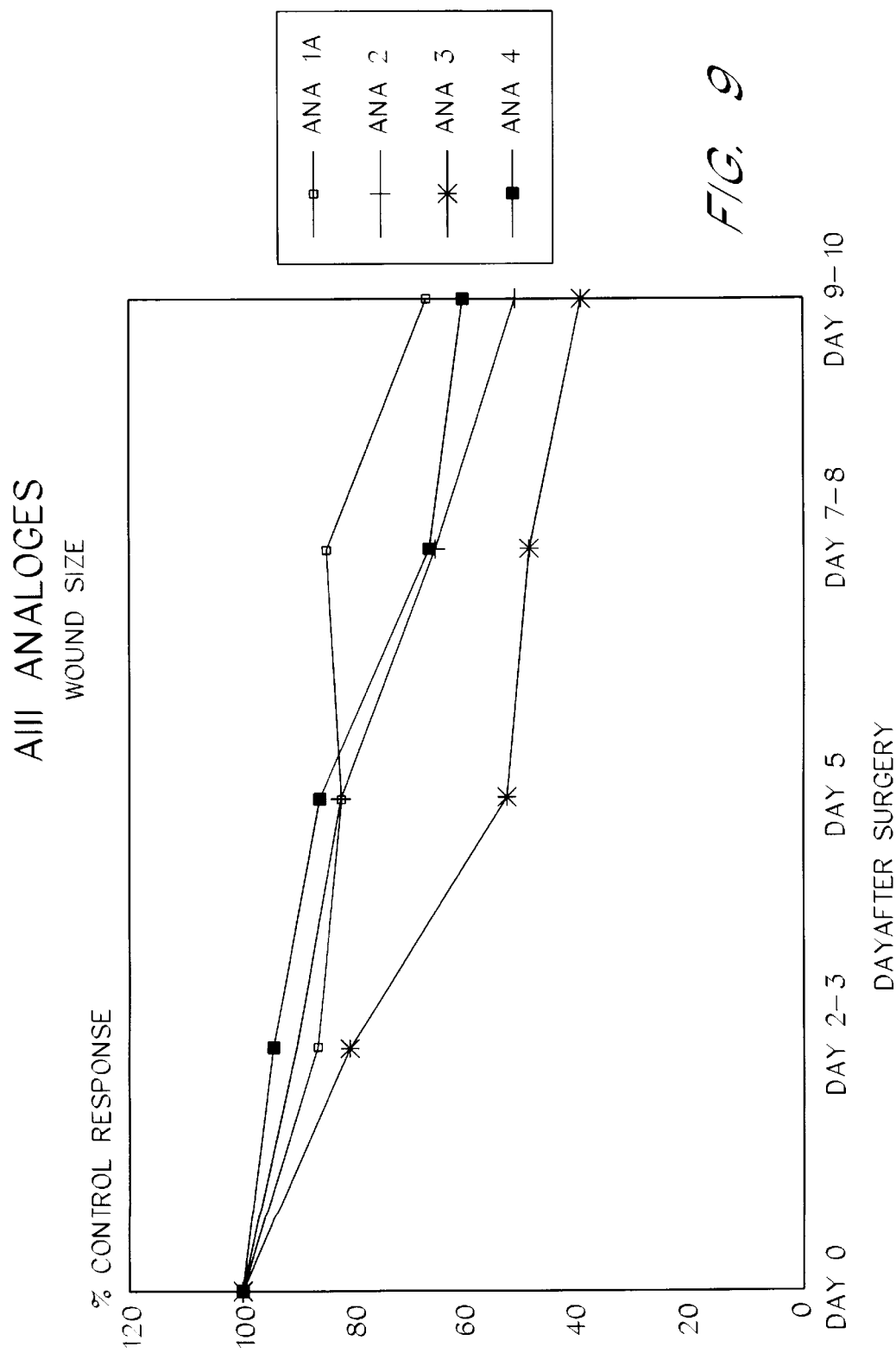
FIG. 9 illustrates the percent of control response in wound closure relative to a vehicle-treated control using various AIII analogs.
Figure 10:
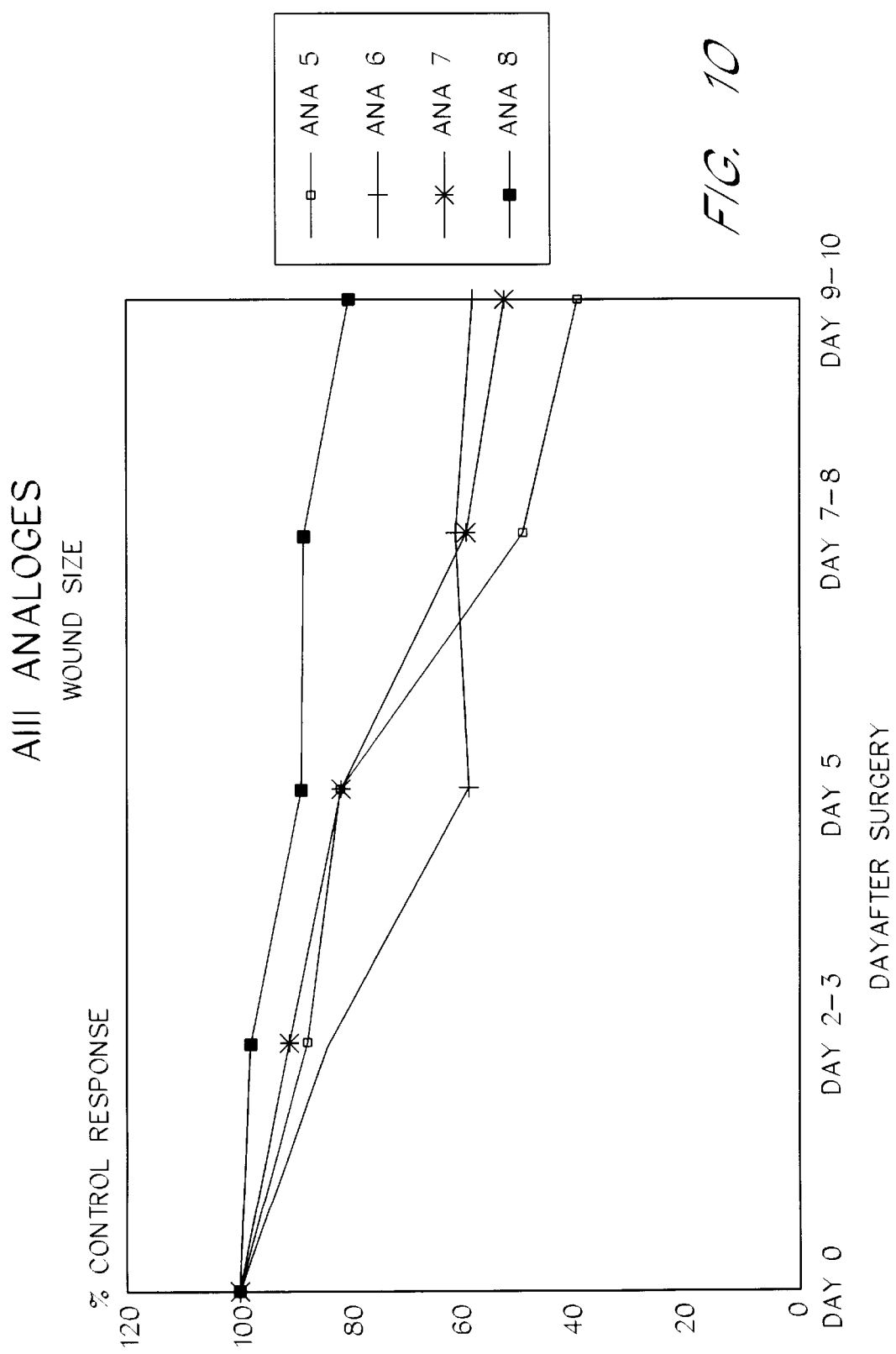
FIG. 10 illustrates the percent of control response in wound closure relative to a vehicle-treated control using various AIII analogs.
Figure 11:
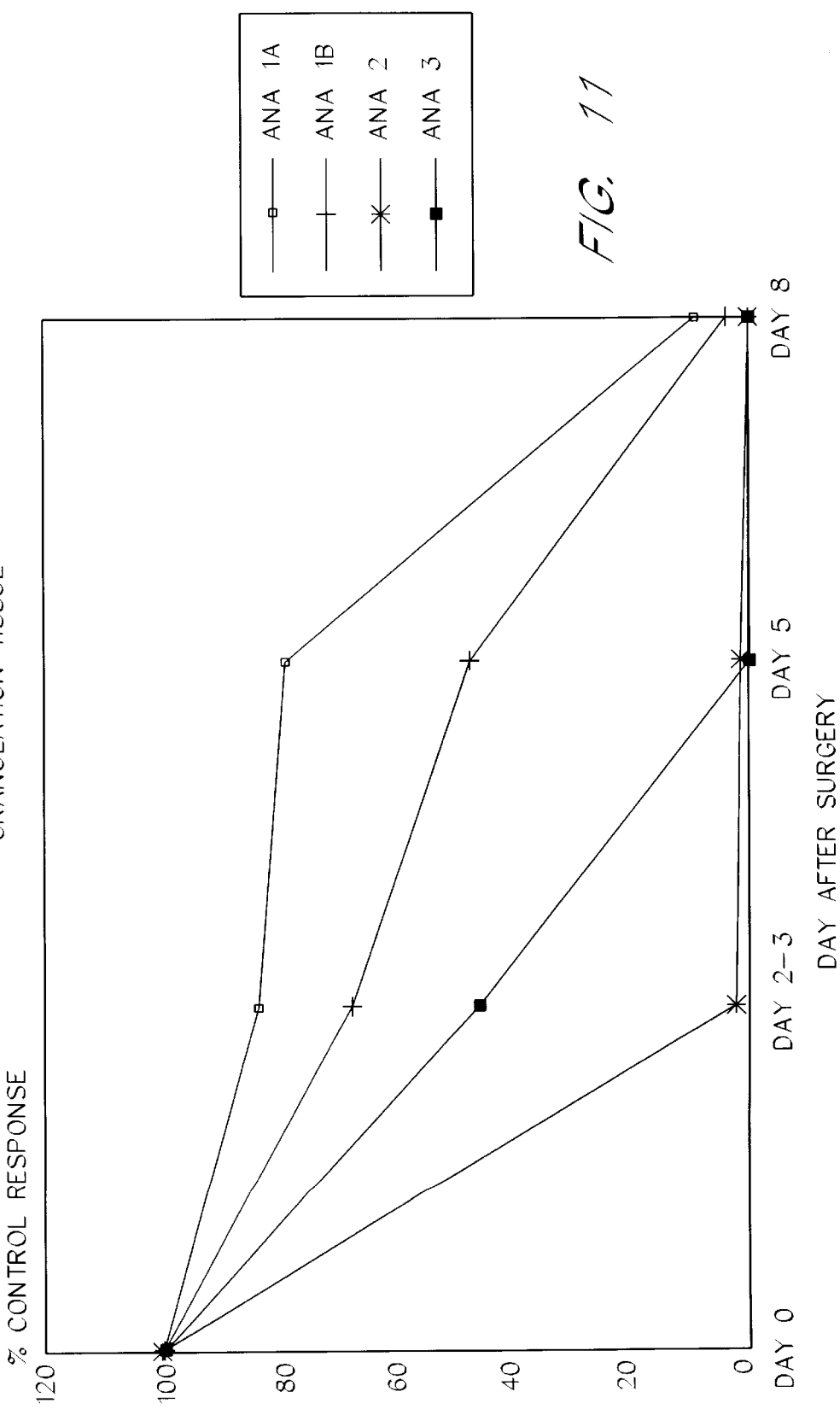
FIG. 11 illustrates the percent of control response in formation of granulation tissue using various AIII analogs.
Figure 12:
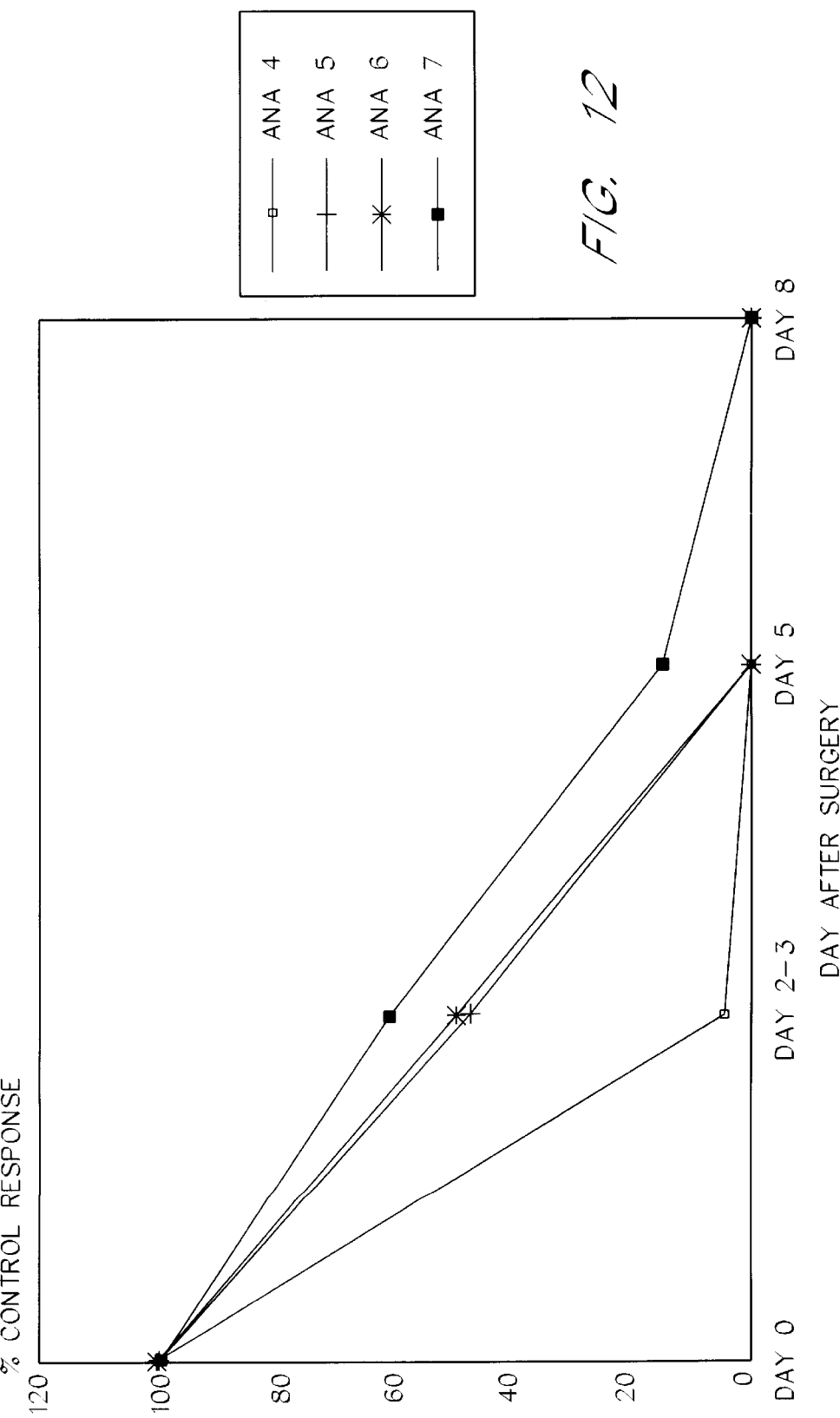
FIG. 12 illustrates the percent of control response in formation of granulation tissue using various AIII analogs.

As illustrated in FIGS. 9–12, wound closure was substantially accelerated relative to the control wounds when the test wounds were treated with AIII analogs 1–8 in accordance with general formula I. FIGS. 9 and 10 illustrate the percent of control response in wound closure relative to a vehicle-treated control; in every case, administration of one of the analogs accelerated the closure of the wound after surgery. FIGS. 11 and 12 illustrate the percent of control response in formation of granulation tissue. Again, in every case administration of one of the analogs accelerated the formation of granulation tissue compared to administration of vehicle alone. Therefore, these analogs clearly were effective in promoting the healing of full thickness dermal wounds.

Example 5 describes the methods used to demonstrate that AII fragments were useful for accelerating healing of full thickness dermal wounds.

EXAMPLE 5

Angiotensin II Fragments Accelerate Healing of Full Thickness Dermal Wounds

Female Sprague Dawley rats weighing 175–200 grams were obtained from Simonsen Laboratories (Gilroy, Calif.). On the date of surgery, rats received intramuscular ketamine/rompum anesthesia prior to preparation for surgery. The rats were shaved and scrubbed with betadine. Two 1.5×1.5 cm full thickness dermal wounds were created on the dorsal surface of the rat. Following excision of the skin, the size of the wound was outlined on a glass slide and the medicament was administered in 100 $\mu$l of 10% low viscosity carboxymethyl cellulose (Sigma). Test materials were administered in a randomized fashion. AII materials were tested at 100 $\mu$g/wound. Control wounds were treated with vehicle only. After administration of the materials, the rats were bandaged and allowed to recover from anesthesia. On days 1–4 after surgery, the rats were treated with an additional 100 $\mu$g of appropriate peptide formulations. At days 2, 4, 7 and 9 the areas of the skin wounds were measured under methoxyflurane anesthesia. The area of the wound was determined by: (1) tracing the wound shape onto graph paper (1×1 mm squares); (2) cutting out the shape; (3) weighing the paper and comparing the weight with a 1.5×1.5 cm paper cutout; and (4) counting the number of squares on the graph paper. In addition, on days 2, 4 and 7 the area of granulation tissue was also determined.

Figure 13:
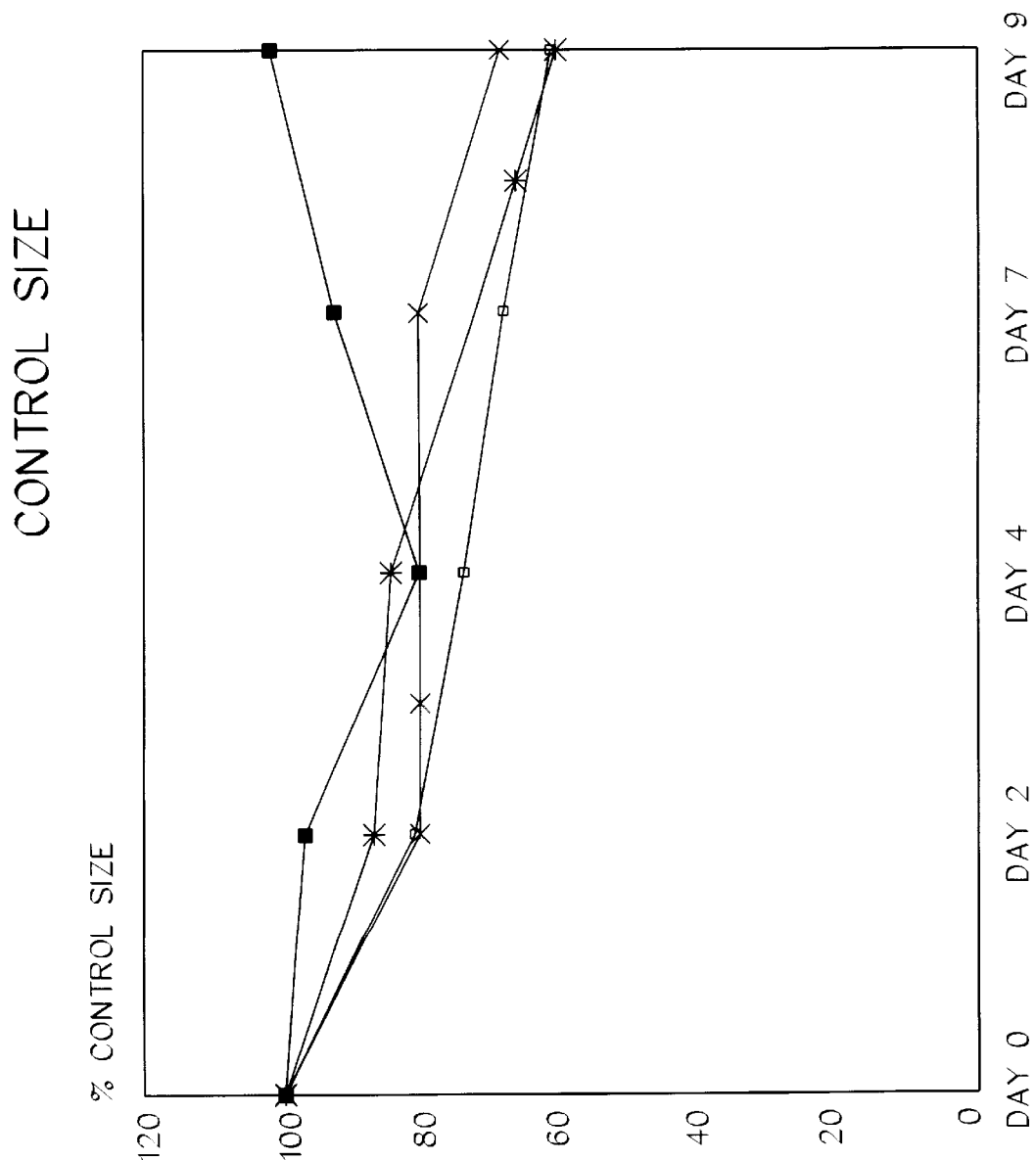
FIG. 13 illustrates the percent of control response in wound closure relative to a vehicle-treated control using various fragments of AII.
Figure 14:
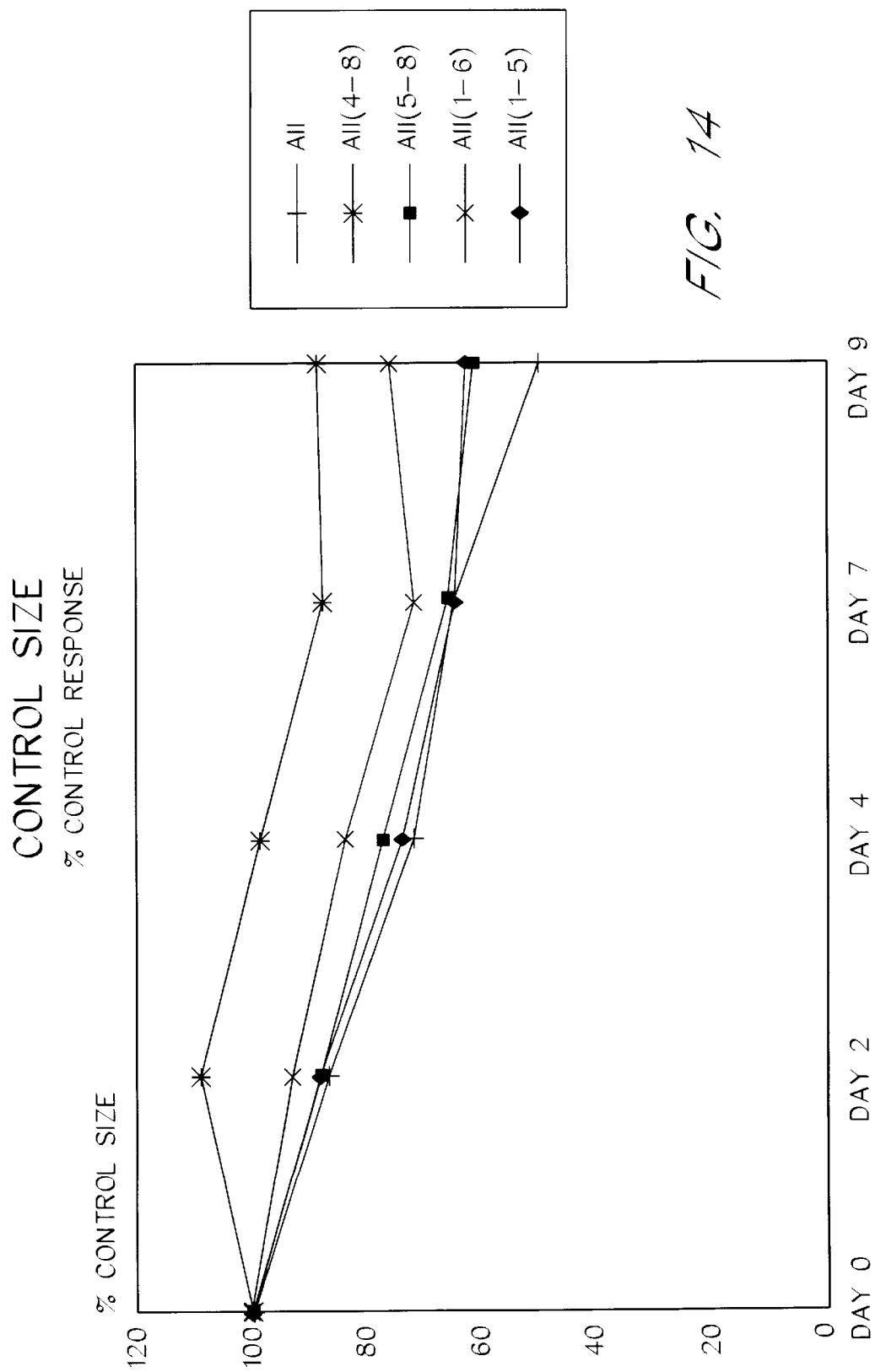
FIG. 14 illustrates the percent of control response in wound closure relative to a vehicle-treated control using various fragments of AII.
Figure 15:
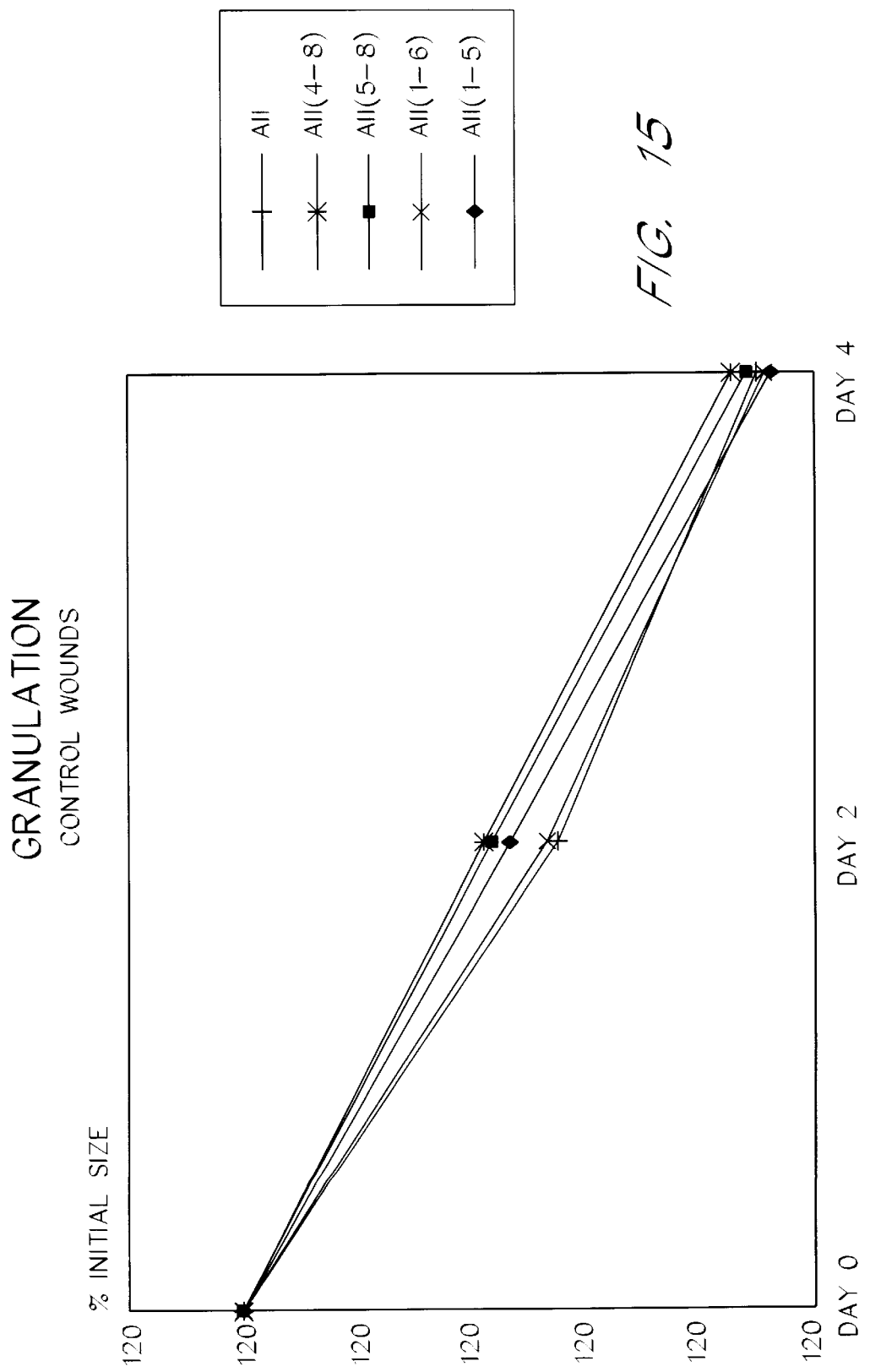
FIG. 15 illustrates the formation of granulation tissue in control wounds of animals treated with various fragments of AII.
Figure 16:
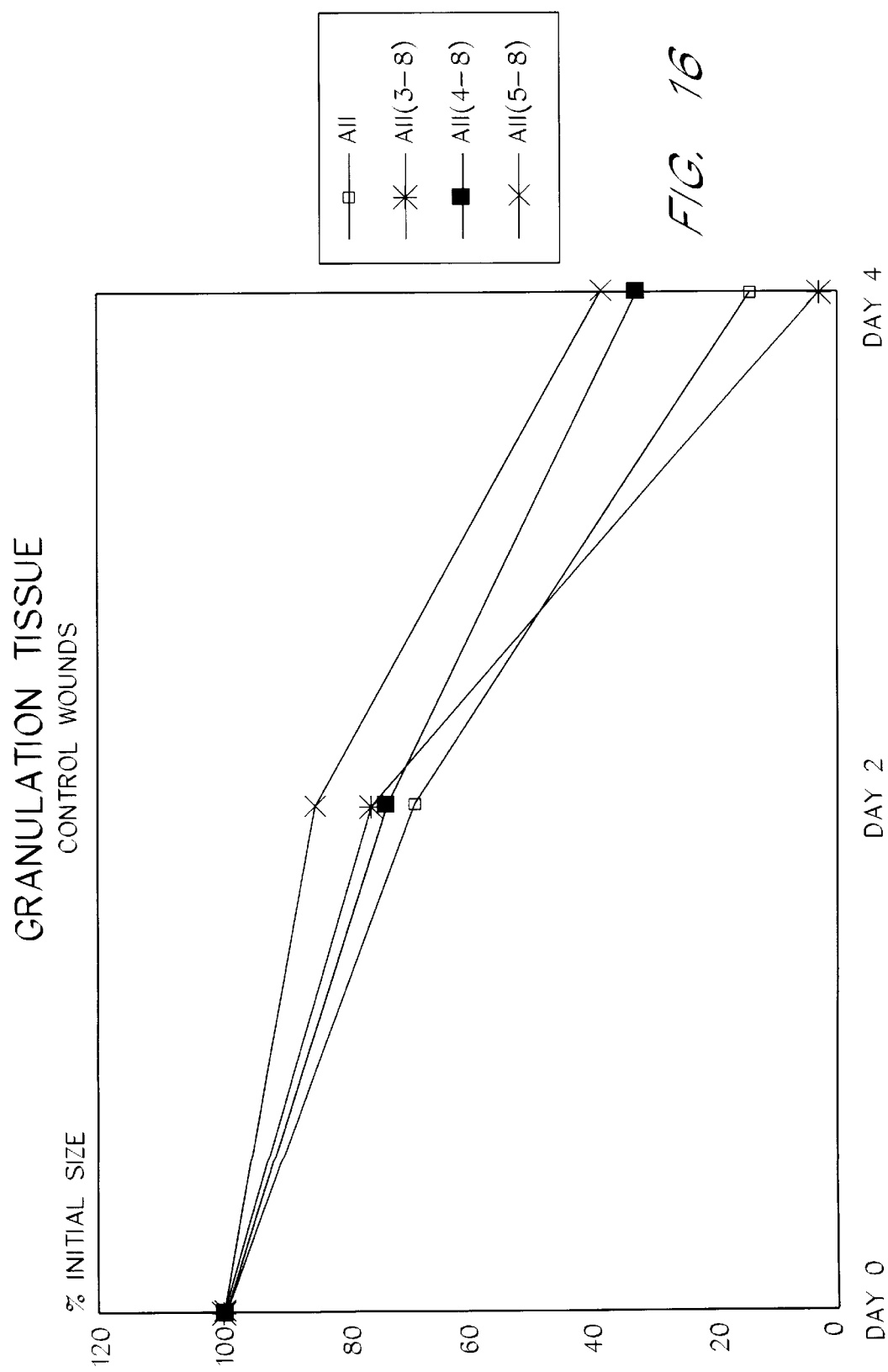
FIG. 16 illustrates the formation of granulation tissue in control wounds of animals treated with various fragments of AII.
Figure 17:
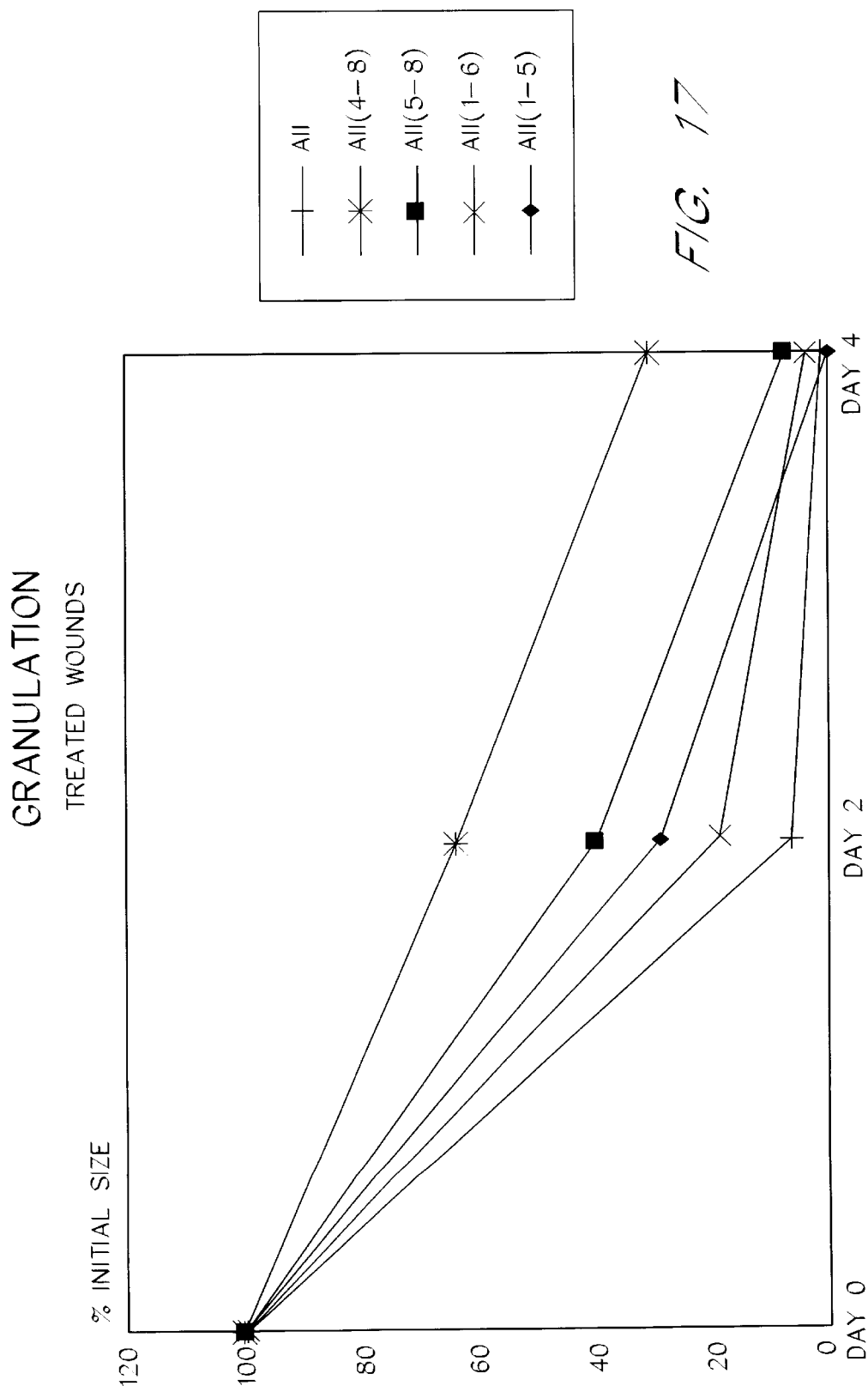
FIG. 17 illustrates the formation of granulation tissue in animals treated with various fragments of AII.
Figure 18:
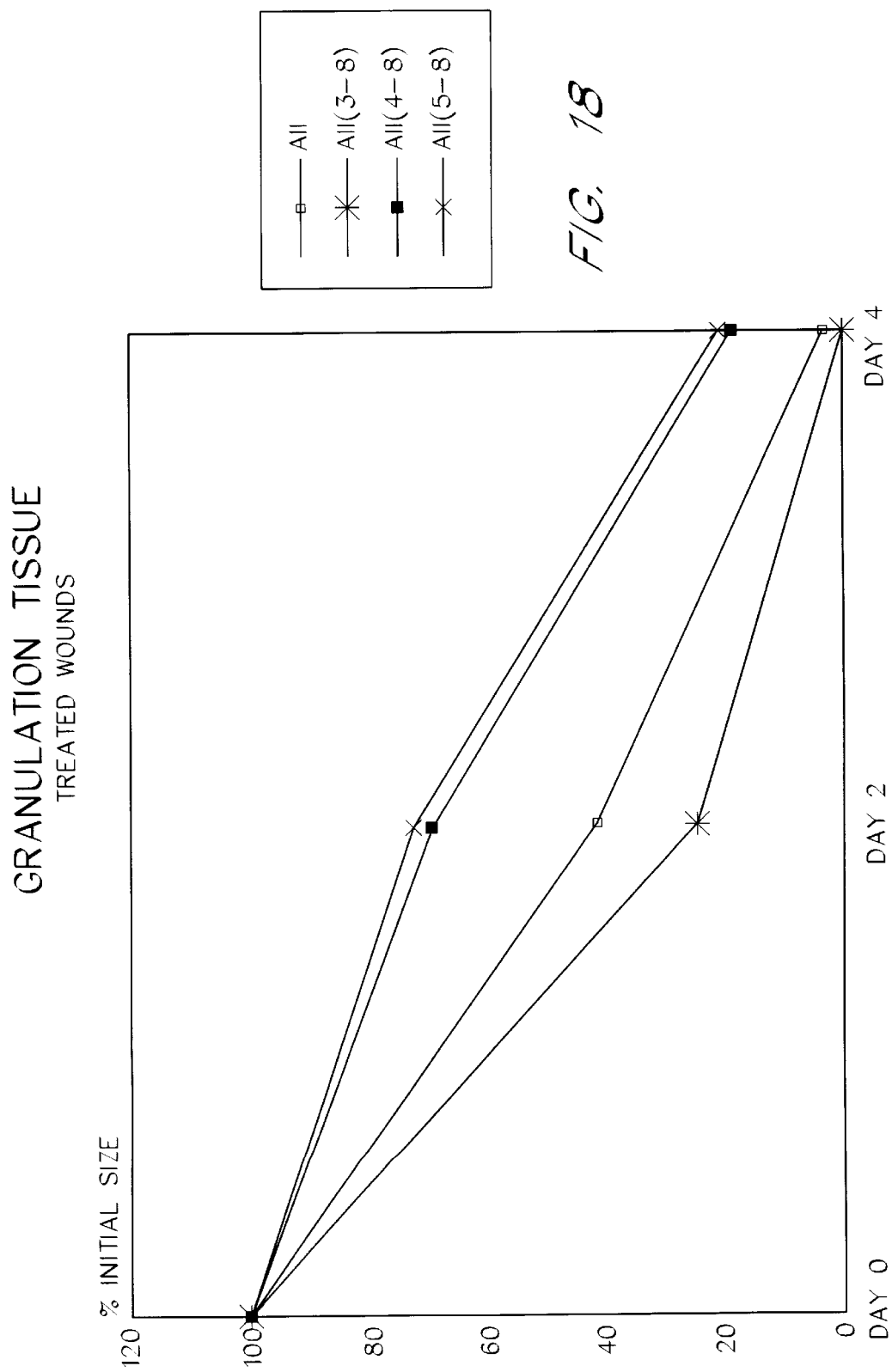
FIG. 18 illustrates the formation of granulation tissue in animals treated with various fragments of AII.
Figure 19:
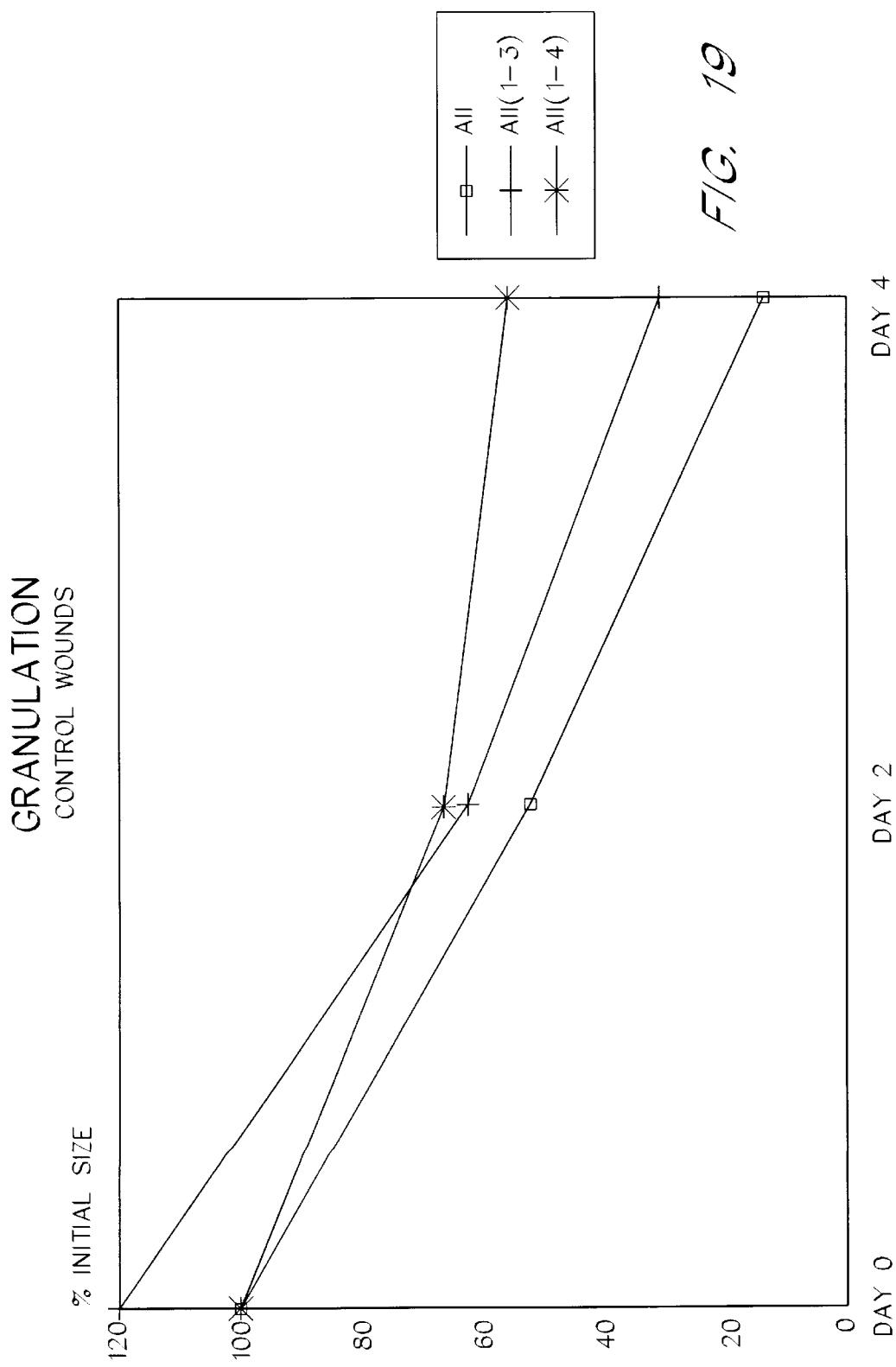
FIG. 19 illustrates the formation of granulation tissue in control wounds of animals treated with various AII fragments.
Figure 20:
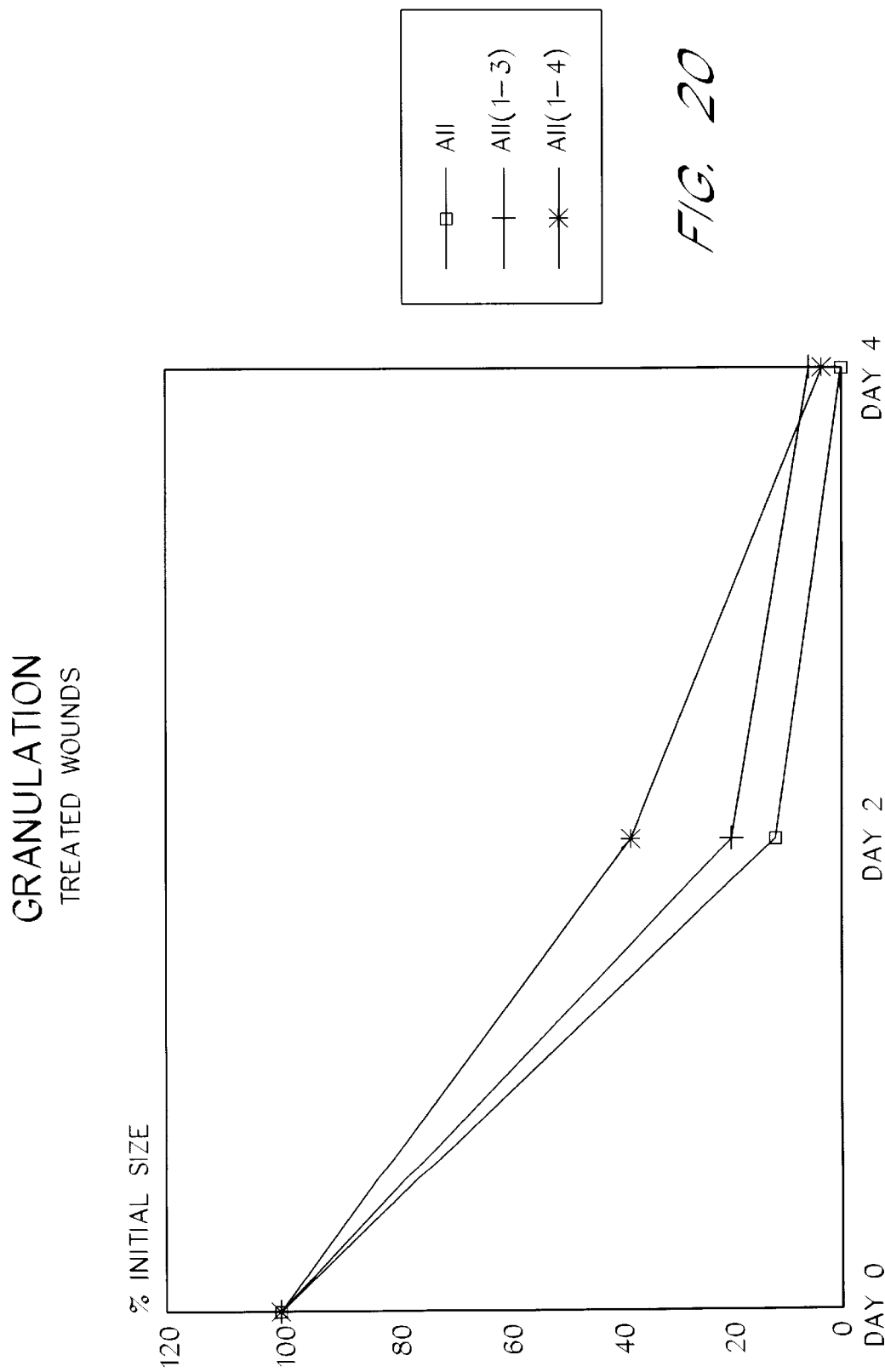
FIG. 20 illustrates the formation of granulation tissue in animals treated with various AII fragments.
Figure 21:
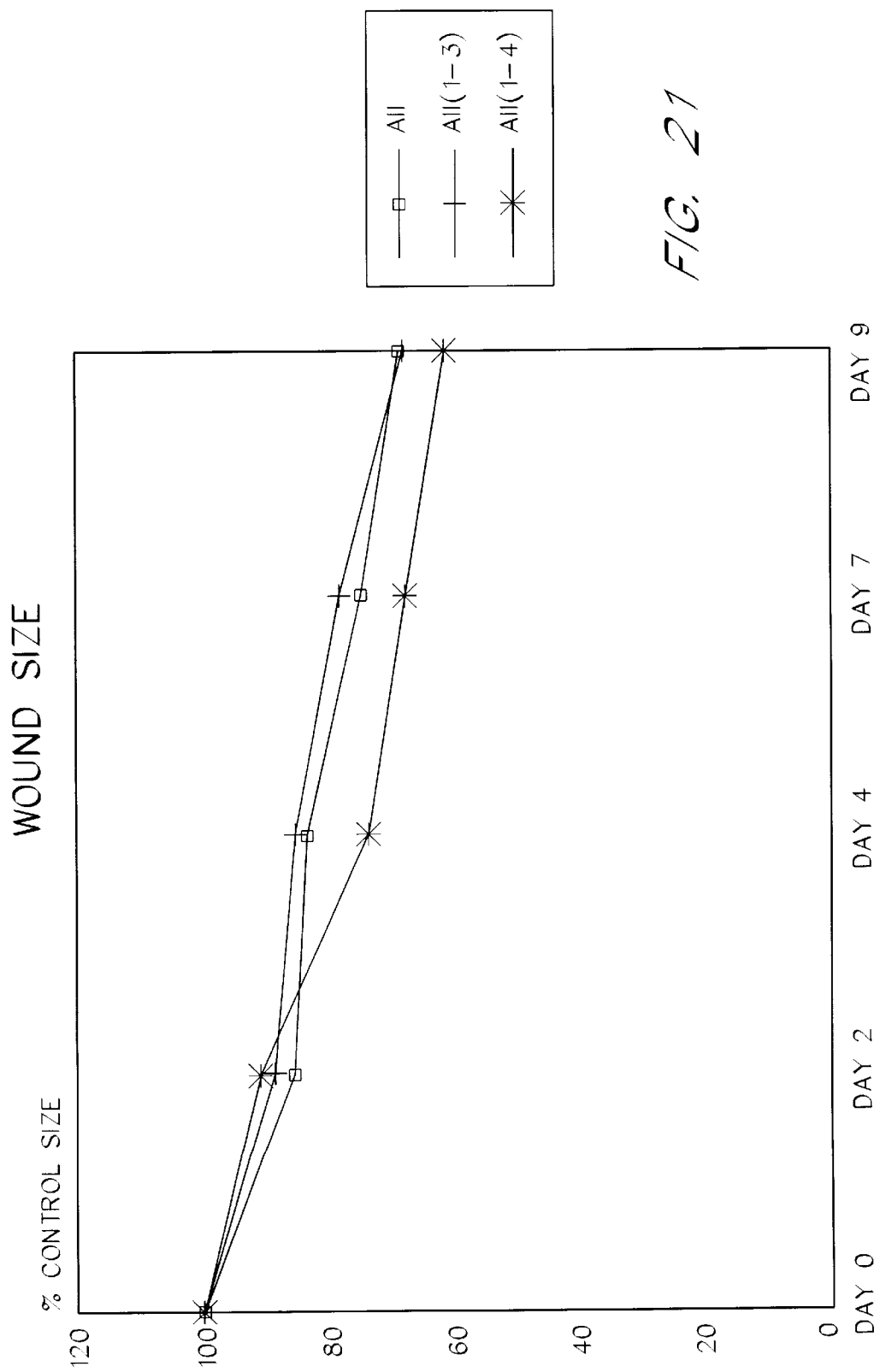
FIG. 21 illustrates the percent of control response in wound closure relative to a vehicle-treated control using various fragments of AII.

As illustrated in FIGS. 13–21, wound closure was substantially accelerated relative to the control animals when the test animals were treated with all fragments except AII(6–8) and AII(4–8). FIGS. 13, 14 and 21 illustrate the percent of control response in wound closure relative to a vehicle-treated control using fragments of AII as herein defined. FIGS. 15–18 and 20–21 compares the percent of vehicle control wounds filled with granulation tissue with that of peptide treated wounds. FIGS. 15, 16 and 19 reflect data from control wounds to which FIGS. 17, 18 and 20, respectively, should be compared.

In the compounds of particular interest in accordance with the present invention, $R^6$ is $pNH_2$-Phe; the literature suggests this amino acid confers agonist activity. It is presently considered that $R^7$ should be Pro in order to provide the most desirable orientation of $R^8$. In the position $R^8$, both a hydrophobic ring and an anionic carboxyl terminal appear to be particularly useful in binding of the analogs of interest to receptors; therefore, Tyr and especially Phe are preferred for purposes of the present invention.

The AT2 agonist p-$NH_2$-Phe6-AII was tested in a rat model for dermal repair and found give results comparable to AII at a dose of 100 $\mu$g/days for 5 days. Both granulation tissue formation and wound closure were examined and found to be accelerated by p-$NH_2$-Phe6-AII.

According to the method of the invention, at least one AT2 agonist is applied to wound tissue in amounts sufficient to increase the healing rate of tissue. These compounds can significantly accelerate the rate of healing at nanomolar levels in vivo. For any given agonist (peptidic or nonpeptidic), optimum levels for use in a given formulation may readily be determined empirically. In general, an amount of active agent suitable for use in accordance with the present invention ranges from about 0.0001 $\mu$g to about 10 mg per kilogram body weight or about 1 ng to 100 mg/cm$^2$ of wound area.

Example 6 describes the methods used to demonstrate that AT2 receptor agonists were useful for accelerating healing of full thickness dermal wounds.

EXAMPLE 6

AT2 Receptor Agonists Accelerate Healing of Full Thickness Dermal Wounds

Female Sprague Dawley rats weighing 175–200 grams were obtained from Simonsen Laboratories (Gilroy, Calif.). On the day of surgery, rats received intramuscular ketamine/rompum anesthesia prior to preparation for surgery. The rats were shaved and scrubbed with betadine. Two 1.5×1.5 cm full thickness dermal wounds were created on the dorsal surface of each rat. Following excision of the skin, the size of the wound was outlined on a glass slide to establish the baseline wound size. The medicament was administered in 100 $\mu$l of 10% low viscosity carboxymethyl cellulose (Sigma). The p-NH$_2$-Phe6-AII test material was administered in a randomized fashion with all materials being tested at 100 μg/wound. Control wounds were treated with vehicle only. After administration of the materials, the rats were bandaged and allowed to recovery from anesthesia. The rats were treated with an additional 100 μg of peptide formulation on days 1–4 after surgery. On days 2, 4, 7 and 9 the area of the skin wounds were measured under methoxyflurane anesthesia. The area of the wound was determined by: (1) tracing the wound shape onto graph paper (1×1 mm squares); (2) cutting out the shape; (3) weighing the paper and comparing the weight with a 1.5×1.5 cm paper cutout; and (4) counting the number of squares on the graph paper. In addition, on days 2, 4 and 7 the area of granulation tissue was similarly determined.

Figure 22:
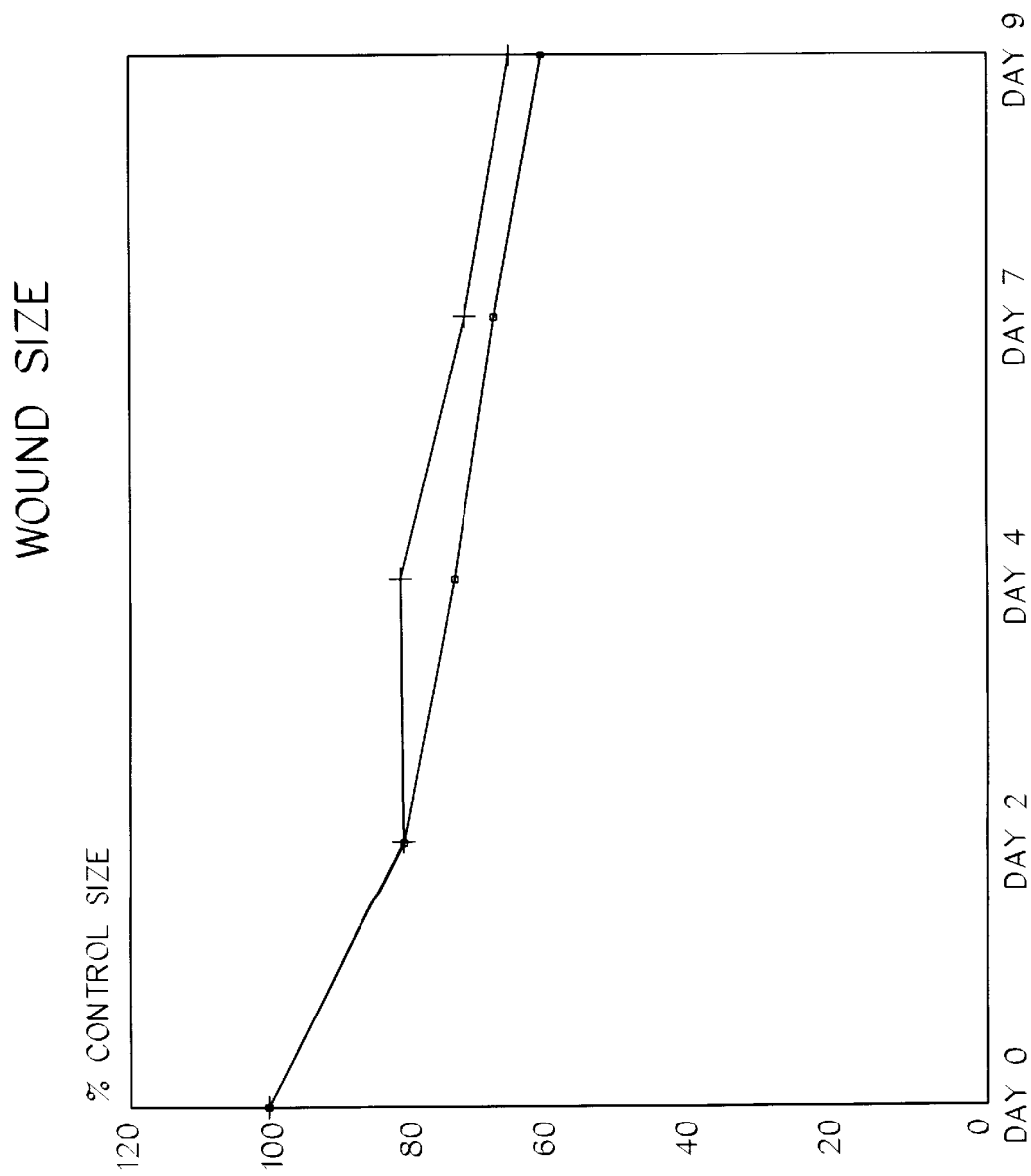
FIG. 22 illustrates the percent of control response in wound closure relative to a vehicle-treated control using (p-NH₂-Phe)6-AII.
Figure 23:
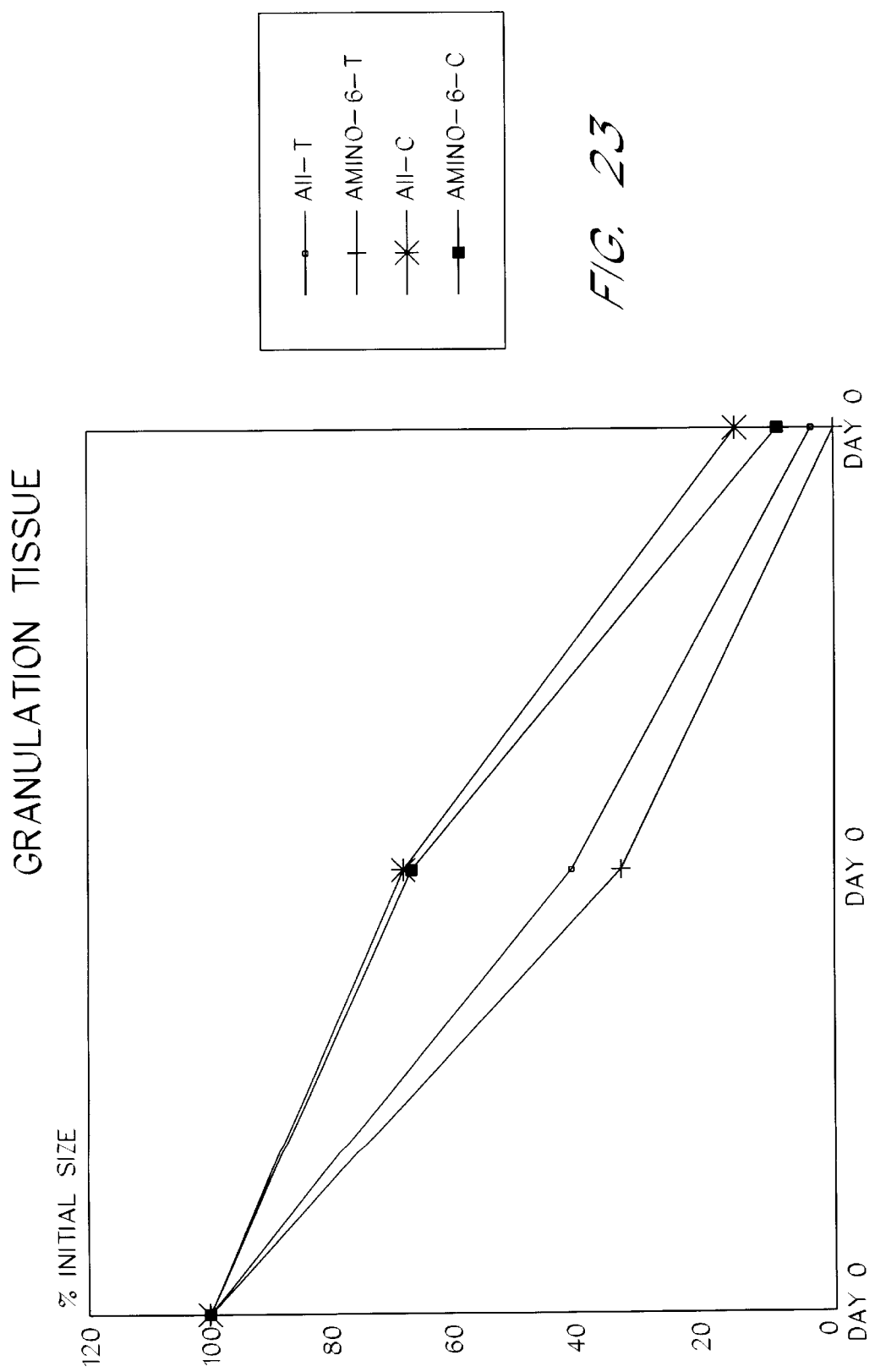
FIG. 23 illustrates the formation of granulation tissue in vehicle-treated or AII, or p-NH₂-Phe6-AII treated wounds.

As illustrated in FIGS. 22–23, wound closure and the formation of granulation tissue was substantially accelerated relative to the control animals when the test animals were treated with an AT2 agonist. FIG. 22 illustrates the percent of control response in wound closure relative to a vehicle-treated control; FIG. 23 illustrates how granulation tissue decreases with time as the result of treatment with peptide analogs of AII and AIII relative to a vehicle control.

Example 7 describes the methods used to demonstrate that additional analogs of AII and AIII were useful for accelerating wound repair in the in vivo model described above.

EXAMPLE 7

Analogs of AII and AIII Accelerate Healing of Full Thickness Dermal Wounds

Analogs of AII and AIII having the structures disclosed in Table 4 were prepared using an automated peptide synthesizer and methods familiar to those having ordinary skill in the art. Each of the analogs was tested for its ability to accelerate wound healing essentially according to the method of Example 6. Results of procedures used to determine the extent of wound closure at days 4 and 9 measured as a percentage of a vehicle-treated control wound are also presented in Table 4. Since all of the analogs were not tested during the same experimental procedure, AII was included as a positive control for each group of peptides tested. As designated below, peptide analogs are identified as analogs of AII or AIII having amino acid substitutions at positions indicated by superscripts. Thus, for example, Gly$^4$-AIII is the designation for an AIII analog having a Gly residue substituted at position 4 of AIII. Results from procedures using analogs that were tested as a group are grouped together in the following Table.

TABLE 4

Compilation of Peptide Efficacies

| Peptide Name | Designation | % Control (Day 4) | % Control (Day 9) |
|---|---|---|---|
| AII | | 86.1 | 57.6 |
| GSD21A | Gly$^4$-AIII | 73.3 | 41.6 |
| GSD22A | Ala$^4$-AIII | 93.0 | 36.0 |
| GSD24A | Pro$^2$-AIII | 79.4 | 47.6 |
| AII | | 84.0 | 64.5 |
| GSD21B | Gly$^5$-AII | 91.1 | 60.3 |
| GSD22B | Ala$^5$-AII | 88.1 | 55.4 |
| GSD24B | Pro$^3$-AII | 82.6 | 43.4 |
| AII | | 76.6 | 62.5 |
| GSD25B | Gly$^3$-AII | 86.4 | 59.4 |
| GSD26B | Leu$^3$-AII | 90.5 | 58.6 |

TABLE 4-continued

Compilation of Peptide Efficacies

| Peptide Name | Designation | % Control (Day 4) | % Control (Day 9) |
|---|---|---|---|
| GSD27B | Aib$^3$-AII | 83.4 | 64.4 |
| AII | | 71.6 | 62.4 |
| GSD28 | Ile$^8$-AII | 78.9 | 54.5 |
| GSD29B | Tyr$^3$-AII | 83.6 | 62.7 |
| GSD30B | Ala$^2$-AII | 93.4 | 43.8 |
| AII | | 81.6 | 63.8 |
| [Tyr(PO$_3$)$_2$]$^4$-AII | | 81.3 | 61.9 |
| β-Asp$^1$-AII | | 101.3 | 100 |
| GSD32B | Pro$^1$-AII | 76.7 | 56.4 |
| AII | | 75.0 | 39.1 |
| G5D36 | Gly$^1$-AII | 80.2 | 65.9 |
| GSD37B | Orn$^2$-AII | 80.6 | 55.4 |
| G5D39B | norLeu$^3$-AII | 81.1 | 62.5 |
| AII | | 79.0 | 59.3 |
| GSD39A | norLeu$^2$-AIII | 73.1 | 43.8 |
| GSD40A | norLeu$^4$-AIII | 95.1 | 78.9 |
| GSD40B | norLeu$^5$-AII | 75.0 | 48.9 |
| AII | | 81.9 | 65.5 |
| GSD41B | homoSer$^4$-AII | 77.6 | 55.8 |

The numerical results presented in Table 4 show that nearly all of the analogs tested in the procedure effectively accelerated the closure of full thickness wounds.

The following Example describes generally how compositions comprising AII, an AT2 agonist, AII analog, AII fragment or analog thereof, angiotensinogen and analogs thereof, angiotensinogen fragments and analogs thereof, angiotensin I and analogs thereof, and angiotensin I fragments and analogs thereof can be used to promote healing of skin grafts. Those having ordinary skill in the art will appreciate that skin grafts represent structures that differ from the open wounds described in the preceding Examples.

More specifically, previous studies have shown that both angiotensin II and platelet-derived growth factor (PDGF) can accelerate the repair of wound tissue and can increase formation of granulation tissue in animal models (diZerega, U.S. Pat. No. 5,015,629; Grotendorst et al. *J. Clin. Invest.* 76:2323 (1985); Pierce et al. *J. Exp. Med.* 167:974 (1988)). Recent studies have shown that PDGF, while increasing the formation of granulation tissue in rabbit ear ulcers, did not effectively increase skin graft survival (Brown et al. *Am. J. Surg.* 171:247 (1996)). These data, together with that disclosed by Eberhard et al. (*Annals of Plastic Surgery* 32:361 (1994)), Hom et al. (*Ann Otol Rhinol Laryngol* 105:109 (1996)), Stepnick et al. (*Arch Otolaryngol Head Neck Surg* 121:667 (1995)) and Nail et al. (*Arch Otolaryngol Head Neck Surg* 122:171 (1996)), indicate that agents useful for accelerating wound repair cannot reasonably be predicted to be useful for increasing graft survival or "take."

As used herein, a skin graft is a piece of graft material that can be transplanted to replace a lost portion of the body skin surface; it may be a full thickness, thick-split, or split-skin graft. Graft material useful in connection with the invention can be graft material taken from the same organism receiving the graft, but may also be allograft material taken or prepared from a nonidentical member of the same species. Also contemplated for use with the invention are graft materials that are xenografts taken from an organism that is a member of a different species with respect to the organism receiving the graft. In all cases, the graft material may be further processed after being isolated from a donor organism. In some cases, the graft material may be artificial skin of the type described by Hansbrough et al. in *J. Burn Care & Rehab.* 15:346 (1994). Additionally, the graft materials contemplated for use in connection with the present invention may be living, dead or inanimate. Contemplated inanimate material will be composed of acellular material. Particular examples of graft materials useful in connection with the invention include: INTEGRA, an acellular dermal xenograft of bovine collagen and chondrotin sulfate (Integra Life Sciences); DERMAGRAFT, an allogenic dermal graft of human fibroblasts on a Vicryl mesh backbone (Advanced Tissue Sciences; San Diego, Calif.); DERMAGRAFT TC, a temporary allograft of human fibroblasts on a nylon mesh with a silicone sheet; and ALLODERM, an allograft from cadaver dermis that has been processed to remove cells (Life Cell, Inc.).

Example 8 illustrates how therapeutic peptides of the type disclosed above can advantageously promote the incorporation of a skin graft into underlying tissue. More particularly, this Example describes how therapeutic peptides can be used in combination with a living cultured skin replacement to aid in the closure of full thickness wound defects in a mammal.

EXAMPLE 8

Methods of Enhancing Incorporation of a Skin Graft into Underlying Tissue

Eighteen female nude mice are first obtained from a commercial vendor. On the date of surgery, the mice receive intramuscular ketamine/rompum anesthesia prior to preparation for surgery. After scrubbing the mice with betadine, a 1×1 cm full thickness dermal wound is created on the dorsal surface of each mouse. Nine of the mice receive grafts consisting of 1×1 cm sections of a living skin replacement graft sutured in place at the corners of the grafts. Prior to contacting the graft and the wound bed, a 100 $\mu$l sample of a pharmaceutically acceptable vehicle comprising 10% carboxymethyl cellulose is applied to the wound bed. After suturing is complete an additional 100 $\mu$l sample of the vehicle is applied to the external surface of the graft. This first group of six mice, which did not receive any therapeutic peptide, represent a negative control group. The second group of nine mice represent a test group of mice. The mice in the test group similarly receive 1×1 cm grafts of artificial skin, but additionally receive application of a 100 $\mu$l sample of a medicament to the wound bed before the graft is sutured in place. The medicament comprises the AII peptide dispersed in 10% low viscosity carboxymethyl cellulose. After suturing is complete, an additional 100 $\mu$l sample of the medicament is applied to the external surface of the graft material. The mice in both the negative control group and the test group are bandaged and allowed to recover from anesthesia. The two groups of mice receive daily applications of either vehicle or medicament, as appropriate.

Results of the grafting procedure are assessed macroscopically and microscopically. Three mice in each of the groups are sacrificed at 6 days and 15 days post-surgery, and tissue sections of the graft area are prepared for histological analysis. Results of microscopic analysis indicate that the dermis of the grafts administered with the medicament containing the therapeutic peptide are more highly vascularized than the negative control grafts at both 6 and 15 days post-surgery. The number and size of the vessels increases during the time interval between 6 and 15 days post-surgery. Macroscopic examination at 21 days post-surgery of the remaining pairs of mice indicates that both of the grafts receiving the therapeutic peptide are firmly adherent to the underlying tissue. In contrast, one of the grafts treated with vehicle alone is non-adherent. The increased vascularity and adherence of the graft treated with the medicament indicates that application of a therapeutic peptide advantageously promotes healing of skin grafts in mammals.

Example 9 describes the methods used to demonstrate that a medicament that included AII was useful for promoting the "take" or incorporation of an autologous skin graft into underlying tissue. In these procedures the AII-containing medicament was applied to the wound bed underlying a skin flap. Flaps were created on the dorsum of experimental animals by making full thickness incisions down to the panniculus carnosus, lifting and then replacing the flap. Although phosphate buffered saline and 10% carboxymethyl cellulose were used as carriers in the following procedures, numerous other carriers useful for administering AII, active AII analogs, AII fragments or analogs thereof, angiotensinogen and analogs thereof, angiotensinogen fragments and analogs thereof, angiotensin I and analogs thereof, and angiotensin I fragments and analogs thereof will be familiar to those having ordinary skill in the art.

EXAMPLE 9

Angiotensin II Enhances Engraftment in a Random Flap Model

Female Sprague Dawley rats were anesthetized with intramuscular anesthesia of ketamine/xylazine. The animals were shaved using animal clippers and then scrubbed with povidone-iodine and isopropyl alcohol. Artificial tears were placed in the eyes of the anesthetized animals. From caudal to encephalad, incisions two 7 cm long were made 1.2 cm apart on the dorsum beginning immediately below the scapula. At the caudal end of the incisions, the 1.2 cm length was cut crosswise so that the three incisions could be connected to define three edges of a skin flap. The flap was raised from the fascia and any connecting tissue was dissected away. A 0.3 ml volume of the medicament was then placed in the wound bed. The skin flap was replaced and held in contact with apposing skin using 8 stitches of 5–0 ETHILON suture obtained from Ethicon (Rantan, N.J.). Medicament formulations tested in this procedure were: (1) a phosphate buffered saline (PBS) negative control, (2) 1 mg/ml AII in PBS, (3) 10 mg/ml AII in PBS, (4) 10% low viscosity carboxymethyl cellulose as a second negative control, and (5) 1 mg/ml AII in 10% low viscosity carboxymethyl cellulose. Sutured flaps were bandaged with TEGADERM that was obtained from 3M Corp. (Minneapolis, Minn.), and sealed on the edges with benzoin. The animals were allowed to recover postoperatively and then observed periodically to assess the level of graft incorporation. Graft incorporation was assessed by: (1) the number or percentage of grafts that were viable, as determined by a healthy intact appearance (Table 5), and (2) % graft scabbing as indicated by discoloration, dryness and necrotic, nonviable tissue (FIGS. 24 and 25).

Figure 24:
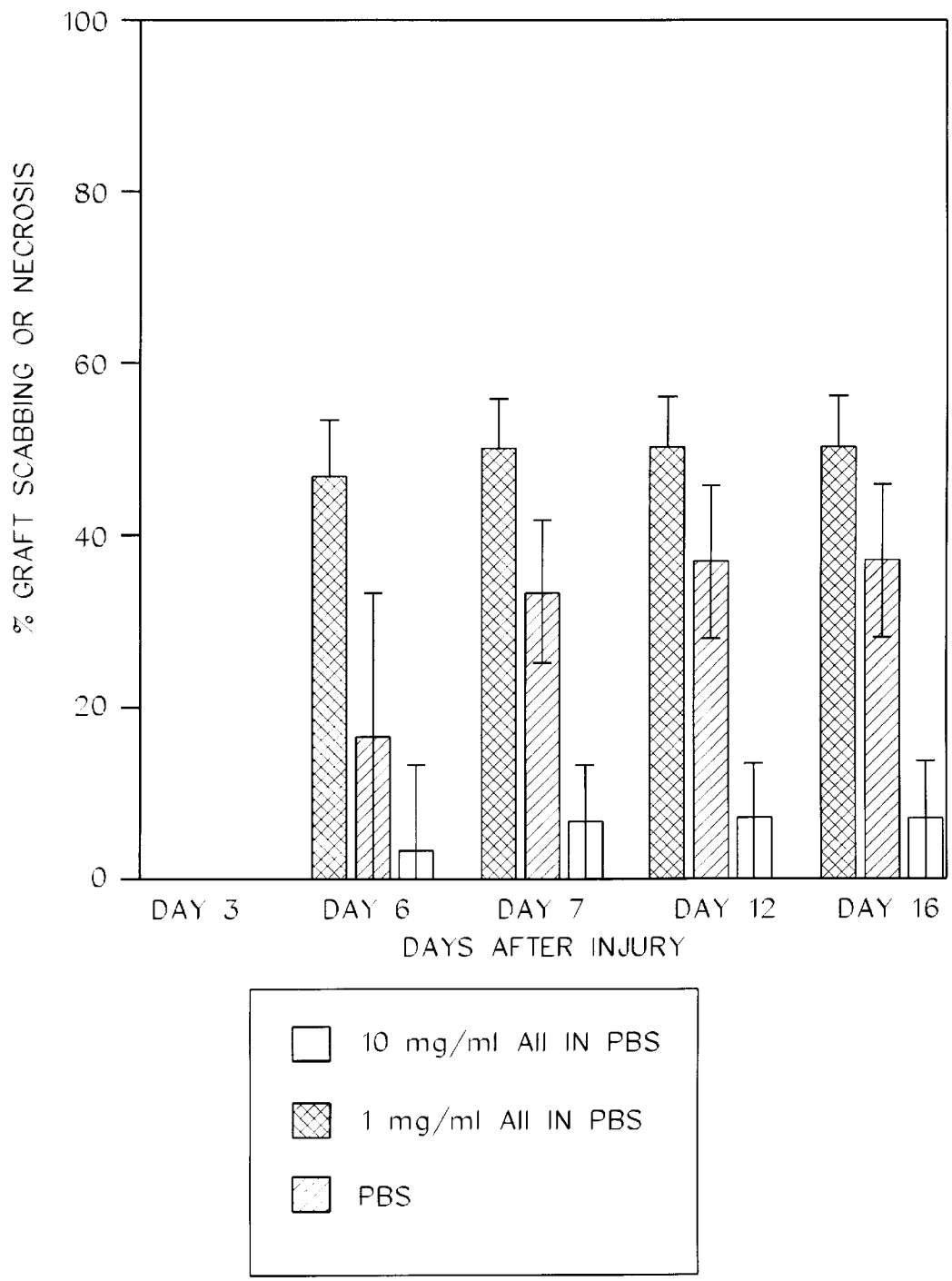
FIG. 24 illustrates the effect of an AII-containing medicament on graft take as measured by % graft scabbing or necrosis at various times following injury in a random flap model.
Figure 25:
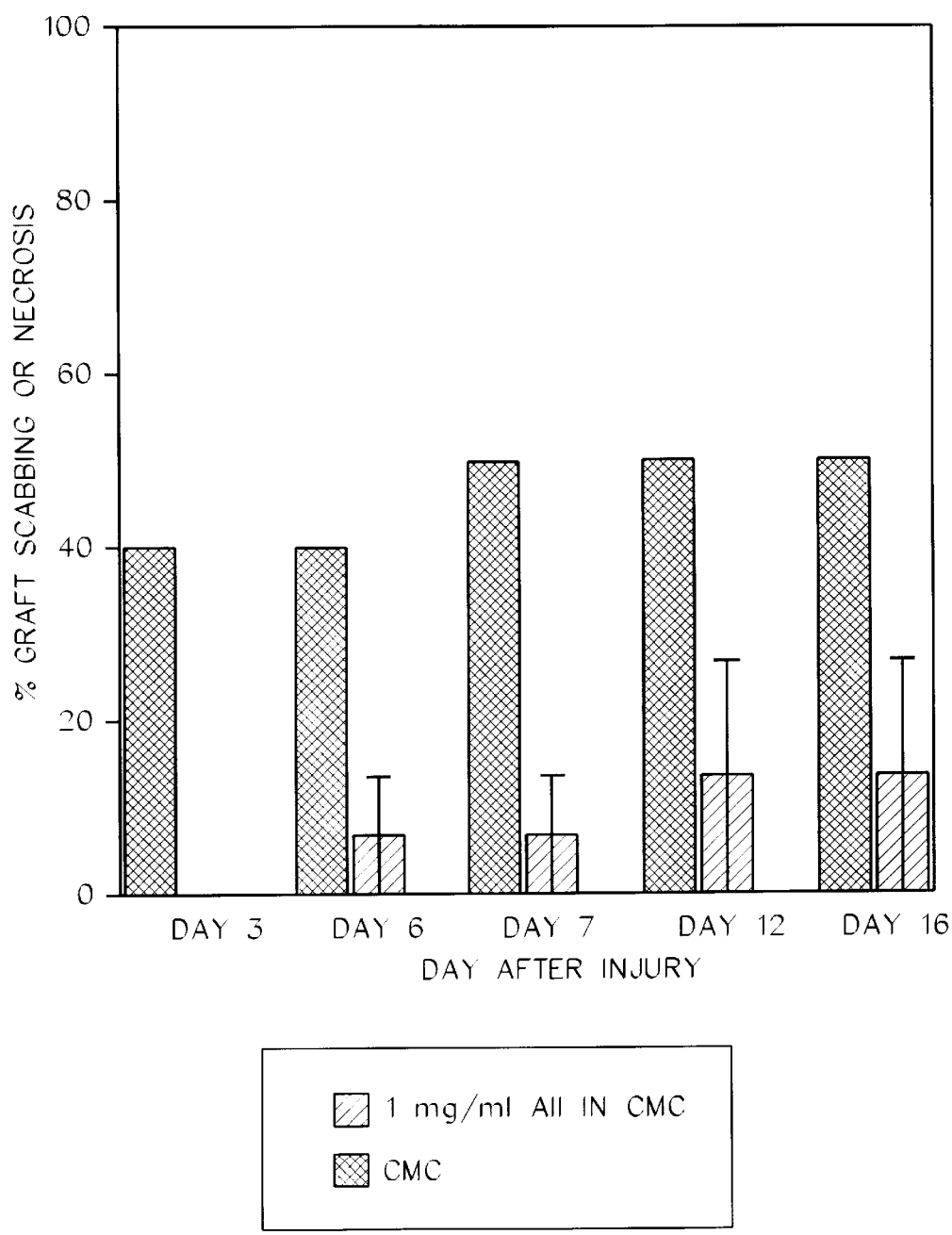
FIG. 25 illustrates the effect of an AII-containing medicament on graft take as measured by % graft scabbing or necrosis at various times following injury in a random flap model.

The results presented in FIGS. 24 and 25 and in Table 5 indicated that medicaments which included AII substantially improved the efficiency of graft incorporation and reduced the proportion of necrotic tissue that was present in viable grafts. More particularly, the results in Table 5 indicated that administration of a single dose of either 10 mg/ml AII in PBS or 1 mg/ml AII in 10% carboxymethyl cellulose at the time of flap formation substantially enhanced the efficiency of graft take within 12 days. Indeed, only grafts which received one of the AII-containing medicaments successfully incorporated into the underlying wound bed. AII of the control grafts treated only with one of the two carriers had graft necrosis on day 12 and 16. In the groups of rats administered with 10 mg/ml AII in PBS or 1 mg/ml AII in 10% carboxymethyl cellulose, 67% of the grafts were viable and the incisions were healed. Some graft necrosis was observed in the remaining animals. The graphic results presented in FIGS. 24 and 25 show that about 50% of the area of grafts showed scabbing or necrosis in the negative control groups that had been treated with one of the two carriers. The percentage of graft scabbing was reduced for grafts that were treated with one of the medicaments that included AII. Grafts treated with either 10 mg/ml AII in PBS or 1 mg/ml AII in 10% carboxymethyl cellulose showed particularly good results, although trials conducted using 1 mg/ml AII in PBS also yielded decreased formation of necrotic tissue.

TABLE 5

AII Enhances Incorporation of Autologous Skin Grafts

| Treatment | Viable Grafts/Total Grafts |
| --- | --- |
| PBS | 0/6 |
| 1 mg/ml AII in PBS | 0/3 |
| 10 mg/ml AII in PBS | 2/3 |
| 10% Carboxymethyl Cellulose | 0/1 |
| 1 mg/ml AII in 10% Carboxymethyl Cellulose | 2/3 |

The results presented in the preceding Example proved that the dramatic differences between success and failure of autologous graft incorporation into an underlying wound bed were attributable to the presence or absence of AII in the medicament that was applied between the wound bed and the overlying graft. The time course results presented in FIGS. 24 and 25 showed that the extent of graft necrosis in experimental system was essentially stabile between 8 and 12 days post-surgery. Accordingly, this time frame was employed in subsequent procedures that were used to establish the dose response relationship between AII administration and the extent of autologous graft incorporation.

Example 10 describes methods that were used to determine optimal dosages for promoting the incorporation of a skin graft into underlying tissue. In these procedures AII was applied to the wound bed underlying an autologous skin graft. Although AII was employed in the following procedure, those having ordinary skill in the art will appreciate that similar procedures can be used to establish optimal dosages of active AII analogs, AII fragments or analogs thereof, angiotensinogen and analogs thereof, angiotensinogen fragments and analogs thereof, angiotensin I and analogs thereof, and angiotensin I fragments and analogs thereof in accordance with the present invention.

EXAMPLE 10

Angiotensin II Enhances Engraftment in a Random Flap Model

Skin flaps were created according to the method of the preceding Example and treated with one of six experimental formulations. After suturing the treated flaps into position, animals were bandaged, allowed to recover and assessed for graft incorporation at 8 and 12 days following surgery. Medicament formulations tested in this procedure were: (1) a negative control consisting of 10% low viscosity carboxymethyl cellulose, and (2) 0.01–1 mg/ml AII in 10% low viscosity carboxymethyl cellulose. Concentrations of AII tested in this procedure were 1.0, 0.3, 0.1, 0.03 and 0.01 mg/ml.

Figure 26:
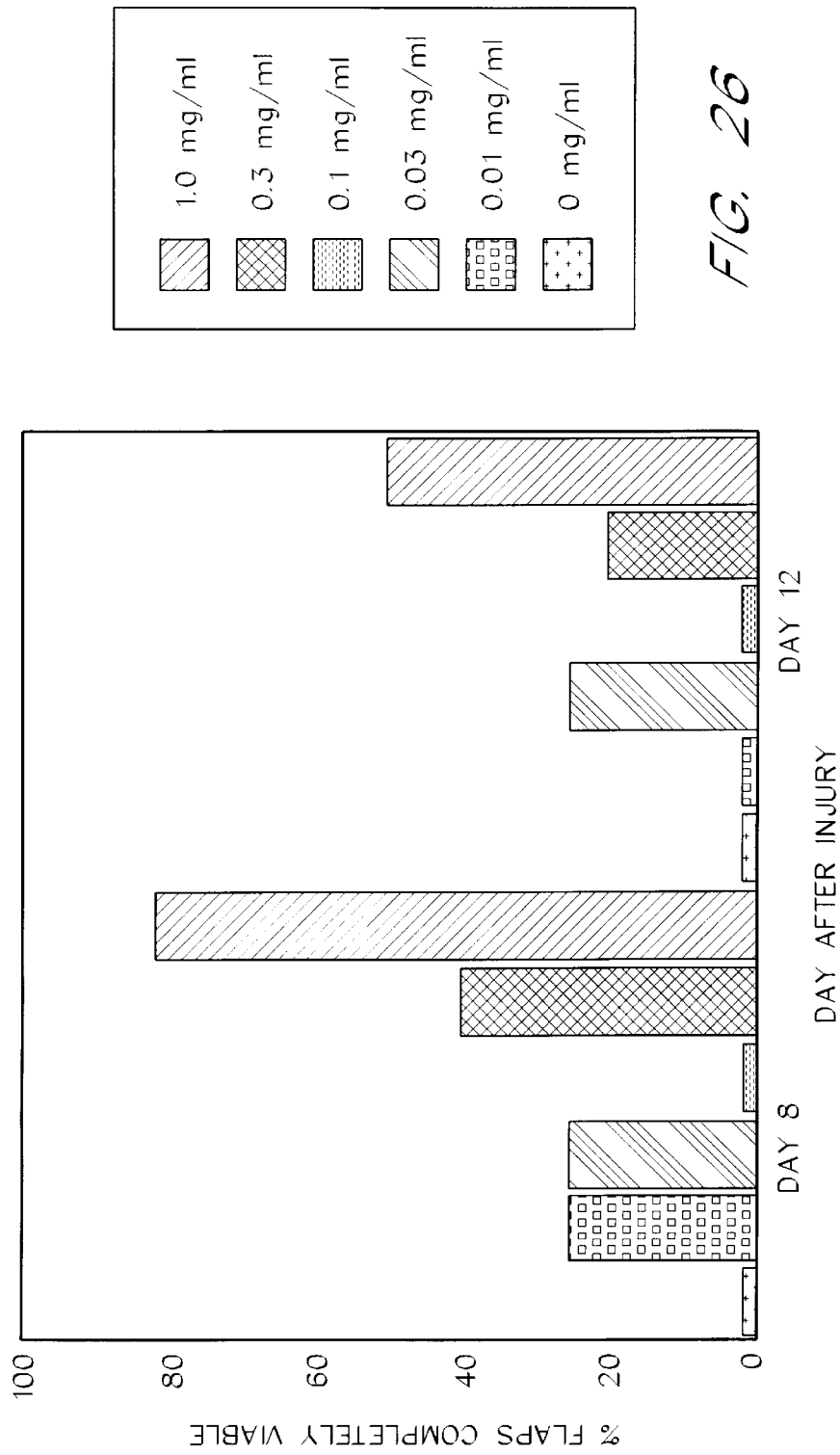
FIG. 26 illustrates the effect of various concentrations of AII on the percentage of flaps completely viable at 8 and 12 days following injury.
Figure 27:
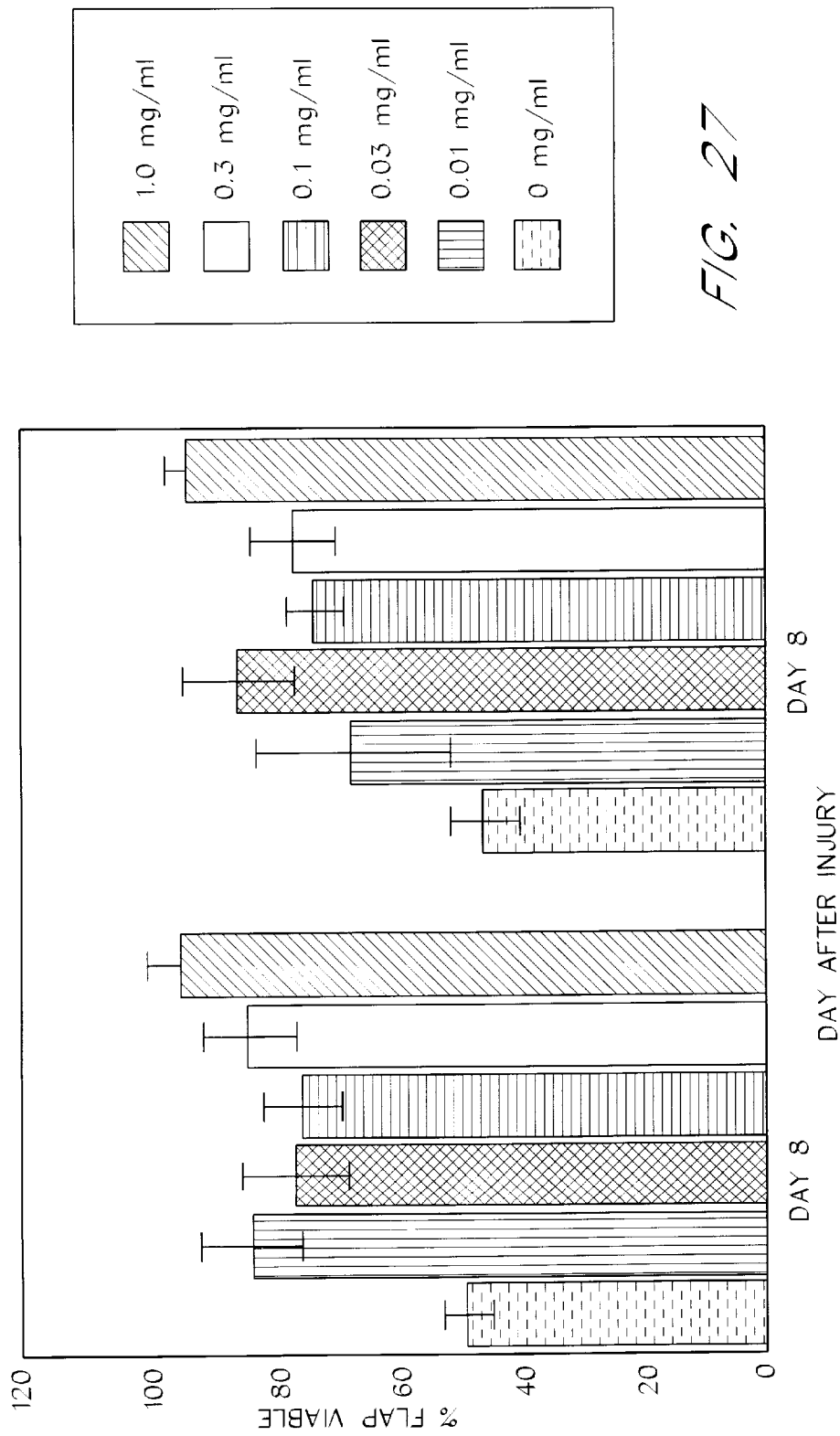
FIG. 27 illustrates the effect of various concentrations of AII on the percentage of flap viability at 8 and 12 days following injury.

The results presented in FIGS. 26 and 27 confirmed that AII enhanced engraftment in a dose responsive manner. More particularly, FIG. 26 shows that administration of a single dose of 0.01–1 mg/ml AII in 10% carboxymethyl cellulose at the time of flap formation increased the efficiency of graft incorporation into underlying tissue, as judged by the percentage of flaps determined to be completely viable at 8 and 12 days post-surgery. Additionally, FIG. 27 shows that the percentage of the flap that was viable was increased in the trials administered with the AII-containing medicament. All of the experimental animals administered with 10% carboxymethyl cellulose as a negative control exhibited graft necrosis 8 and 12 days post-surgery. In contrast, even the lowest dosage of AII tested in the procedure substantially increased the fractional flap viability when compared with the vehicle-treated control. These results proved that the observed positive effects on graft incorporation were attributable to the activity of AII. Moreover, these results demonstrate methods of optimizing dosages of therapeutic compounds that promote incorporation of skin grafts. An optimal dosage will be the amount of medicament that provides substantially the highest level of % of flaps completely viable at the correspondingly lowest dosage of medicament. For example, if maximal flap survival is obtained when the medicament contains 0.03 mg/ml of a particular AII-related compound, so that higher concentrations provide no added benefit, then the optimal dosage would be 0.03 mg/ml.

The foregoing procedures employed an autologous graft model to demonstrate how the compositions disclosed herein could be used to promote graft incorporation. Given this demonstration, it was of interest to determine whether the disclosed compositions also were useful for promoting the incorporation of non-autologous grafts. In the Example which follows, an artificial skin or "living skin equivalent" formed a viable graft over a wound bed that had been created by full thickness excision only after treatment with AII. A subsequent Example describes a similar result in a debrided burn model. Living skin equivalents of the type used in the procedures described herein can be obtained from commercial sources such as Organogenesis, Inc. (Canton, Mass.) and Ortec Inc. (New York, N.Y.). The skin replacements used in the methods disclosed herein were composed of human fibroblasts that condense a bovine collagen lattice which is then seeded with cultured human keratinocytes. The collagen lattice with fibroblasts serves as a dermal template, and the overlying human keratinocytes form the epidermal component of the composite skin replacement. A description of the composition of this skin replacement has been presented by Hansbrough et al. in *J. Burn Care & Rehabil.* 15:346 (1994), the entire disclosure of this article being incorporated herein by reference.

Example 11 describes the methods that were used to demonstrate how AII could be used to enhance engraftment using a living skin equivalent in a full thickness excision model. Similar procedures can be used to enhance engraftment of different living skin equivalents using active AII analogs, AII fragments or analogs thereof, angiotensinogen and analogs thereof, angiotensinogen fragments and analogs thereof, angiotensin I and analogs thereof, and angiotensin I fragments and analogs thereof.

EXAMPLE 11

Engraftment of Artificial Skin to the Site of a Full Thickness Excision Site

Six male Swiss nude mice (22–24 grams) were purchased from Taconic Laboratories (Germantown, N.Y.) and quarantined for at least 2 days prior to surgery. Following anesthesia by intramuscular injection of KETASET/ROMPUM that had been obtained from Western Medical Supply (Arcadia, Calif.), 1 cm×1 cm full thickness skin excisions were made on the dorsum of each mouse. Living skin equivalents produced essentially as described by Hansbrough et al. (supra.) were obtained from a commercial source. This material was placed in the wound defect and trimmed with a microscissor so that no gap was observed between the edges of the mouse skin and the graft material. The mice were divided into 3 groups of 2 mice per group based upon the treatment administered to the graft material prior to placement in the wound bed. In group 1, the living skin equivalent was removed from its culture dish and placed directly on the wound bed. The mice in group 2 were grafted with the living skin equivalent that had been soaked in lactated Ringer's solution with 5% dextrose for 10 minutes prior to placement in the wound bed. In group 3, the living skin equivalent was soaked for 10 minutes in a lactated Ringer's solution with 5% dextrose containing 1 mg/ml AII before placement in the wound bed. After the graft material had been placed, the dorsal surface of the mouse was covered by petrolatum embedded gauze followed by two adhesive bandages. After recovery from anesthesia, the mice were returned to individual cages and observed daily until euthanasia. All mice received intramuscular analgesia for the first three days after surgery. No mouse lost the bandage prior to necropsy on day 7 (1 mouse from each group) or day 9 (1 mouse from each group). At necropsy, the degree of graft incorporation and the appearance of the graft was noted before placing the biopsy in 10% buffered formalin in preparation for paraffin embedding, sectioning and staining with hematoxylin and eosin.

Figure 28:
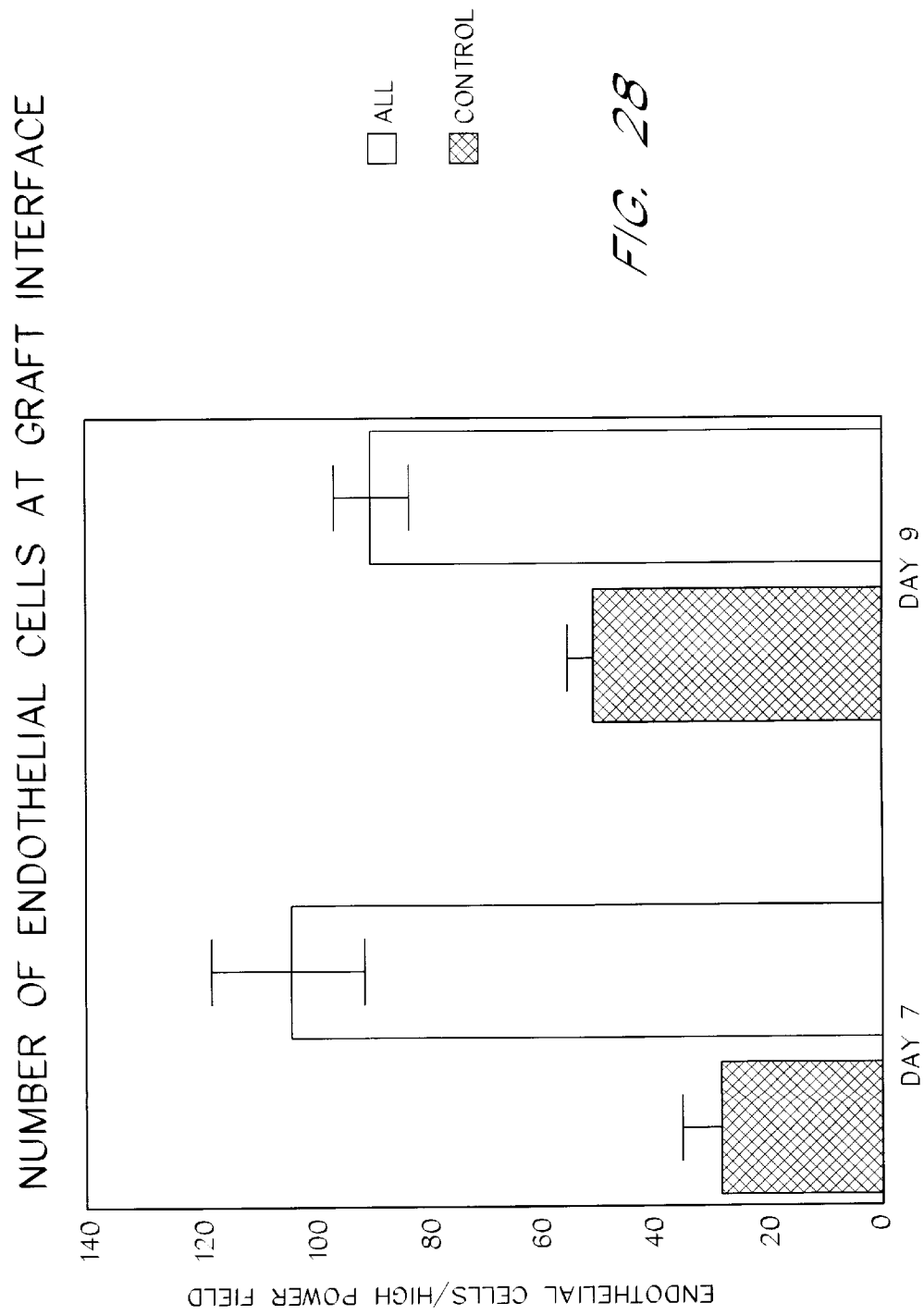
FIG. 28 illustrates the effect of AII on the number of endothelial cells at the graft interface per high power field at 7 and 9 days post-surgery.
Figure 29:
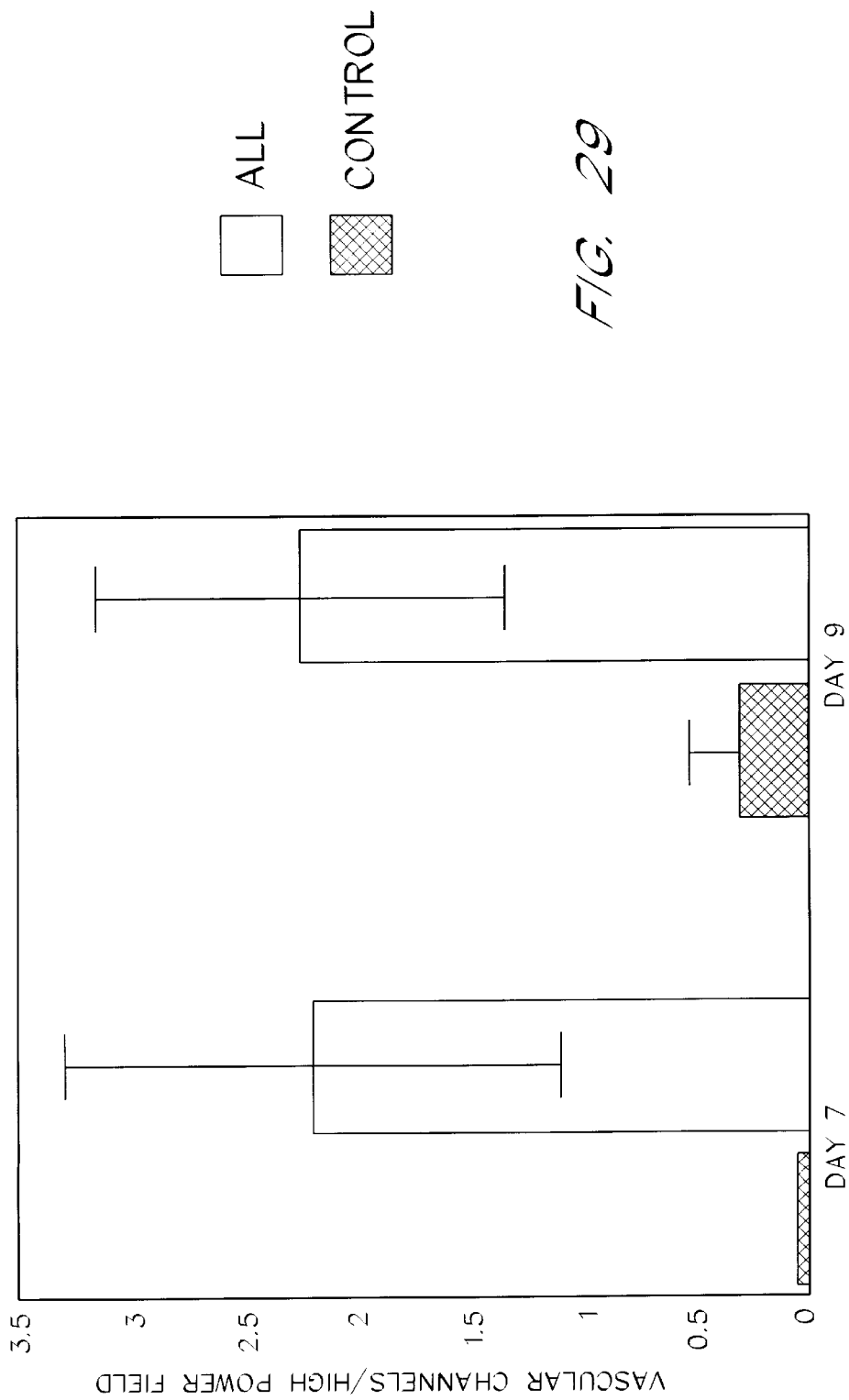
FIG. 29 illustrates the effect of AII on the number of vascular channels containing red blood cells at the graft interface per high power field at 7 and 9 days post-surgery.

Results of these procedures indicated that AII had a positive effect on the incorporation of a living skin equivalent into full thickness wounds. AII grafts appeared healthy and inosculation was noted for 80–100% of the graft edges on days 7 and 9. Thus, soaking the living skin equivalent in lactated Ringer's solution did not adversely affect the graft material. Microscopic analysis indicated that one of the AII-treated grafts had numerous vessels attached to the underside against the fascia by 7 days post-surgery. This was not noted for either of the two grafts that were untreated, nor for the two grafts that had been soaked in Ringer's solution, nor in one of the grafts that had been treated with the AII-containing solution. Histological analysis also was used to assess the number of endothelial cells and the number of red blood cell-containing vascular channels as a measure of tissue integration in 20x microscope fields at the interface between the living skin equivalent and adjacent mouse tissue. Between 9 and 20 fields were counted for each graft to make this analysis. Control data were obtained using grafts that had been soaked in lactated Ringer's solution with 5% dextrose for approximately 10 minutes prior to placement in the wound bed. The results presented in FIGS. 28 and 29 show that soaking the living skin equivalent in an AII solution for 10 minutes prior to placement increased the number of endothelial cells and vascular channels containing red blood cells at both 7 and 9 days post-surgery, suggesting that integration with the murine tissue occurs more rapidly. At both time points the results obtained for the grafts that had been treated with AII were similar. However, from day 7 to 9 there was an increase in the number of endothelial cells and vascular channels at the interface between the living skin equivalent and mouse tissue for the vehicle-treated grafts.

Since AII-containing preparations enhanced the incorporation of autologous grafts and living skin equivalents into underlying tissue, it was of interest to further explore the range of graft applications that would be improved by administration of AII, active AII analogs, AII fragments or analogs thereof, angiotensinogen and analogs thereof, angiotensinogen fragments and analogs thereof, angiotensin I and analogs thereof, and angiotensin I fragments and analogs thereof. The following Example illustrates how AII can be used to promote the incorporation of a living skin equivalent into a debrided burn injury. Similar results are to be expected when active AII analogs, AII fragments or analogs thereof are substituted for AII, angiotensinogen and analogs thereof, angiotensinogen fragments and analogs thereof, angiotensin I and analogs thereof, and angiotensin I fragments and analogs thereof.

Example 12 describes the methods used to demonstrate that compositions of the type disclosed herein were useful for promoting the incorporation of living skin equivalents into the site of a debrided burn injury.

EXAMPLE 12

Engraftment of Artificial Skin to a Debrided Site 48 Hours After Full Thickness Burn Injury In Nude Mice Male Swiss nude/nude mice (26 grams) were purchased from Taconic Laboratories (Germantown, N.Y.) and quarantined for a period of 5 days prior to induction of a full thickness burn injury. The burn injury was produced by contacting the skin on the dorsum for a period of 10 seconds with a brass rod that had been heated to 100° C. Two days after induction of the burn, the site was excised and the area grafted with a living skin equivalent that had been pre-treated either by soaking for 10 minutes in: (1) saline solution, or (2) saline solution made 1 mg/ml AII.

Results of these procedures indicated that AII enhanced the incorporation of a living skin equivalent at the site of a burn injury. Only one of the mice grafted with a living skin equivalent that had been soaked in saline remained alive on day 21. The graft on this surviving mouse was contracted and nonviable. A second mouse that received a similarly treated graft died with a necrotic graft at 6 days post-surgery. Conversely, at 21 days post-surgery one mouse that had been grafted with the living skin equivalent soaked in the AII solution before placement had a fully viable graft. Two other mice had grafts that were partially contracted and nonviable. Thus, the only graft that successfully incorporated into the tissue underlying a debrided burn injury was the graft that had been treated with AII prior to placement. This confirmed that the compounds disclosed herein were useful for enhancing graft take at the site of debrided burn injuries.

The following procedures were carried out to study, by quantitative histology, the effect on neovascularization of presoaking a living skin equivalent in a lactated Ringer's solution with dextrose and containing AII prior to grafting.

Example 13 describes the methods used to demonstrate that soaking a living skin equivalent in a solution which included AII prior to graft placement advantageously showed increased numbers of endothelial cells and numbers of vascular channels at the graft interface.

EXAMPLE 13

Soaking a Living Skin Equivalent in a Solution Comprising AII Improves Incorporation into Underlying Tissue Twelve male Swiss nude mice (22–24 g) were purchased from Taconic Laboratories and quarantined at least 2 days prior to surgery. The mice were anesthetized with an intramuscular injection of Ketaset/Rompun and single 1 cm×1 cm full thickness skin excisions were made on the dorsal surface of each mouse. A living skin equivalent essentially of the type described by Hansbrough et al. (Supra) was placed in the defect and trimmed with microscissor so that no gap was observed between the edges of the mouse skin and the living skin equivalent. The mice were divided into 4 groups (3 per group) based upon the AII concentration in the solution that was used for soaking the living skin equivalent prior to placement. The AII concentrations used in these procedures were: 0, 0.01, 0.1, and 1.0 mg/ml. After the graft was placed, the dorsal surface of the mouse was covered by petrolatum embedded gauze followed by two adhesive bandages (Baxter). After recovery from anesthesia, the mice were returned to their individual cages and observed daily until euthanasia. The mice received intramuscular analgesia for the first three days after surgery. No mouse lost its bandages prior to necropsy on day 7. At necropsy, the degree of graft take and the appearance of the grafted tissue was noted prior to placement of the biopsy in 10% buffered formalin in preparation for paraffin embedding and section for hematoxylin and eosin staining.

Figure 30:
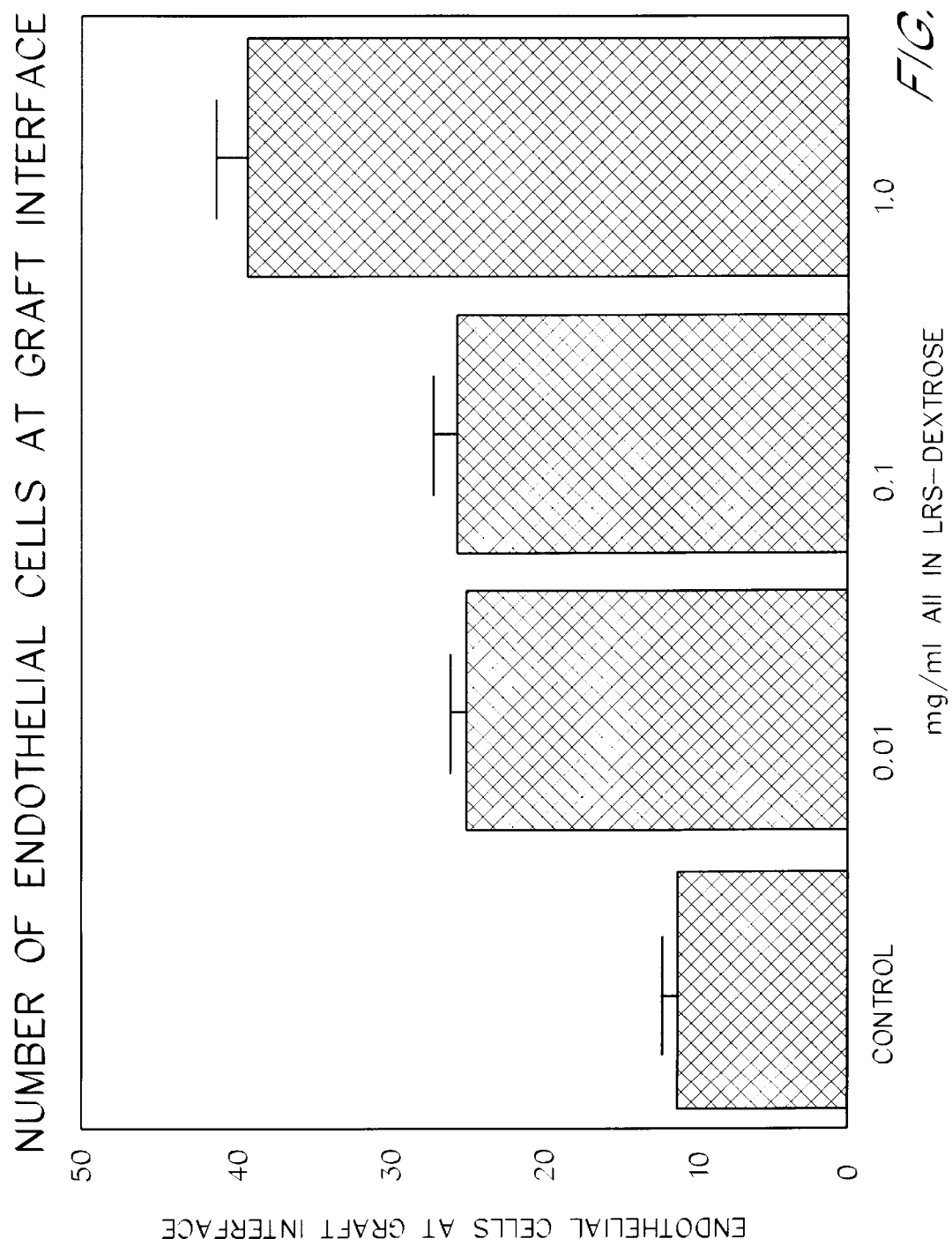
FIG. 30 illustrates how the number of endothelial cells at the graft interface depended on the concentration of AII in the soaking solution.

Results of these procedures indicated that all grafts appeared healthy (except 1 control animal which had lost its graft) and inosculation was noted for 80–100% of the graft edges. One of the AII-treated graft had numerous vessels attached to the underside of the graft against the fascia of the nude mice after full thickness excision. This was not noted on any of the other mice. The number of endothelial cells and vascular channels containing red blood cells per 20× microscope field (between 9 and 20 fields were counted per mouse) present at the interface between the living skin equivalent and the nude mouse tissue was then determined. The control data were obtained from the grafts that had been soaked in lactated Ringer's saline with dextrose for 10 minutes as a vehicle control. These data are represented in FIGS. 30 and 31. Soaking the living skin equivalent in a solution of 0.01–1 mg/ml AII for 10 minutes prior to placement was shown to increase the number of both endothelia cells and vascular channels containing red blood cells. Thus, this dose-response experiment showed that: (1) the living skin equivalent could be soaked in a lactated Ringer's saline solution for 10 minutes prior to graft placement without deleterious effect; and (2) a living skin equivalent pre-treated with AII showed accelerated neovascularization, as determined by endothelial cell number and vascular channels, at the graft site. Additionally, these data show that the effect was concentration-dependent.

In general, the aggregated results presented above indicated that compounds shown above to be useful for accelerating wound healing also are useful for promoting incorporation of skin grafts into underlying tissue.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A method of promoting incorporation of a skin graft into underlying tissue of a mammal, comprising the steps of:
applying to said skin graft or said underlying tissue an effective graft incorporation promoting amount of a composition comprising angiotensin II and a pharmacologically acceptable carrier;
contacting said skin graft and said underlying tissue; and
securing said skin graft to said underlying tissue, whereby incorporation of said skin graft into said underlying tissue is promoted.

2. The method of claim 1, wherein said pharmacologically acceptable carrier comprises a buffered saline solution.

3. The method of claim 2, wherein the applying step comprises soaking said skin graft.

4. The method of claim 1, wherein the pharmacologically acceptable carrier comprises carboxymethyl cellulose.

5. The method of claim 4, wherein the composition applied in the applying step is applied to said underlying tissue.

6. The method of claim 2, wherein the composition applied in the applying step is applied to said underlying tissue.

7. The method of claim 1, wherein the securing step comprises suturing.

8. The method of claim 1, wherein the securing step comprises bandaging.

9. The method of claim 1, wherein the securing step comprises applying a biological glue.

10. A method of promoting incorporation of a skin graft into underlying tissue of a mammal, comprising the steps of:
applying to said skin graft or said underlying tissue an effective graft incorporation promoting amount of a composition which includes a pharmacologically acceptable carrier and a peptide consisting of at least three contiguous amino acids of groups $R^1$–$R^8$ in the general formula $$R^1-R^2-R^3-R^4-R^5-R^6-R^7-R^8$$

wherein $R^1$ is selected from the group consisting of Asp, Glu, Asn, Acpc, Ala, $Me^2$Gly, Pro, Bet, Glu($NH_2$), Gly, Asp($NH_2$) and Suc;
$R^2$ is selected from the group consisting of Arg, Lys, Ala, Orn, Ser(Ac), Sar, D-Arg and D-Lys;
$R^3$ is selected from the group consisting of Val, Ala, Leu, norLeu, Ile, Gly, Pro, Aib, Acpc and Tyr;
$R^4$ is selected from the group consisting of Tyr, Tyr ($PO_3$)$_2$, Thr, Ser, homoSer and azaTyr;
$R^5$ is selected from the group consisting of Ile, Ala, Leu, norLeu, Val and Gly;
$R^6$ is His, Arg or 6-$NH_2$-Phe;
$R^7$ is Pro or Ala; and
$R^8$ is selected from the group consisting of Phe, Phe (Br), Ile and Tyr, excluding sequences including $R^4$ as a terminal Tyr group;
contacting said skin graft and said underlying tissue; and
securing said skin graft to said underlying tissue, whereby incorporation of said skin graft into said underlying tissue is promoted.

11. The method of claim 10, wherein said pharmacologically acceptable carrier comprises a buffered saline solution.

12. The method of claim 11, wherein the applying step comprises soaking said skin graft.

13. The method of claim 10, wherein the pharmacologically acceptable carrier comprises carboxymethyl cellulose.

14. The method of claim 13, wherein the composition applied in the applying step is applied to said underlying tissue.

15. The method of claim 11, wherein the composition applied in the applying step is applied to said underlying tissue.

16. The method of claim 10, wherein the securing step comprises suturing.

17. The method of claim 10, wherein the securing step comprises bandaging.

18. The method of claim 10, wherein the securing step comprises applying a biological glue.

19. A method of promoting incorporation of a skin graft into underlying tissue of a mammal, comprising the steps of:

applying to said skin graft or said underlying tissue an effective graft incorporation promoting amount of a composition which includes a pharmacologically acceptable carrier and a peptide having the general formula

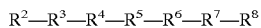

in which $R^2$ is selected from the group consisting of H, Arg, Lys, Ala, Orn, Ser(Ac), Sar, D-Arg and D-Lys;
$R^3$ is selected from the group consisting of Val, Ala, Leu, norLeu, Ile, Gly, Pro, Aib, Acpc and Tyr;
$R^4$ is selected from the group consisting of Tyr, Tyr($PO_3$)$_2$, Thr, Ser, homoSer and azaTyr;
$R^5$ is selected from the group consisting of Ile, Ala, Leu, norLeu, Val and Gly;
$R^6$ is His, Arg or 6-$NH_2$-Phe;
$R^7$ is Pro or Ala; and
$R^8$ is selected from the group consisting of Ile, Phe, Phe(Br) and Tyr;
contacting said skin graft and said underlying tissue; and
securing said skin graft to said underlying tissue, whereby incorporation of the skin graft into the underlying tissue is promoted.

20. The method of claim 19, wherein said pharmacologically acceptable carrier comprises a buffered saline solution.

21. The method of claim 20, wherein the applying step comprises soaking said skin graft.

22. The method of claim 19, wherein the pharmacologically acceptable carrier comprises carboxymethyl cellulose.

23. The method, of claim 19, wherein the composition applied in the applying step is applied to said underlying tissue.

24. The method of claim 20, wherein the composition applied in the applying step is applied to said underlying tissue.

25. The method of claim 19, wherein the securing step comprises suturing.

26. The method of claim 19, wherein the securing step comprises bandaging glue.

27. The method of claim 19, wherein the securing step comprises applying a biologic glue.

28. A method of promoting incorporation of a skin autograft into underlying tissue of a mammal, comprising the steps of:
applying to said skin autograft or said underlying tissue an effective graft incorporation promoting amount of a composition comprising a pharmacologically acceptable carrier and a compound selected from the group consisting of angiotensin II, an analog of angiotensin II, a fragment of angiotensin II and an analog of a fragment of angiotensin II;
contacting said skin autograft and said underlying tissue; and
securing said skin autograft to said underlying tissue, whereby incorporation of said skin autograft into said underlying tissue is promoted.

29. The method of claim 28, wherein said compound is a peptide consisting of at least three contiguous amino acids of groups $R^1$–$R^8$ in the general formula

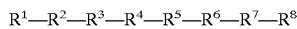

wherein $R^1$ is selected from the group consisting of Asp, Glu, Asn, Acpc, Ala, $Me^2$Gly, Pro, Bet, Glu($NH_2$), Gly, Asp($NH_2$) and Suc;

$R^2$ is selected from the group consisting of Arg, Lys, Ala, Orn, Ser(Ac), Sar, D-Arg and D-Lys;
$R^3$ is selected from the group consisting of Val, Ala, Leu, norLeu, Ile, Gly, Pro, Aib, Acpc and Tyr;
$R^4$ is selected from the group consisting of Tyr, Tyr($PO_3$)$_2$, Thr, Ser, homoSer and azaTyr;
$R^5$ is selected from the group consisting of Ile, Ala, Leu, norLeu, Val and Gly;
$R^6$ is His, Arg or 6-$NH_2$-Phe;
$R^7$ is Pro or Ala; and
$R^8$ is selected from the group consisting of Phe, Phe(Br), Ile and Tyr, excluding sequences including $R^4$ as a terminal Tyr group.

30. The method of claim 28, wherein said compound is a peptide having the general formula

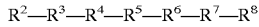

in which $R^2$ is selected from the group consisting of H, Arg, Lys, Ala, Orn, Ser(Ac), Sar, D-Arg and D-Lys;
$R^3$ is selected from the group consisting of Val, Ala, Leu, norLeu, Ile, Gly, Pro, Aib, Acpc and Tyr;
$R^4$ is selected from the group consisting of Tyr, Tyr($PO_3$)$_2$, Thr, Ser, homoSer and azaTyr;
$R^5$ is selected from the group consisting of Ile, Ala, Leu, norLeu, Val and Gly;
$R^6$ is His, Arg or 6-$NH_2$-Phe;
$R^7$ is Pro, Ala; and
$R^8$ selected from the group consisting of Ile, Phe, Phe(Br) and Tyr.

31. The method of claim 28, wherein said skin autograft is a living skin equivalent.

32. A method of promoting incorporation of a skin allograft into underlying tissue of a mammal, comprising the steps of:
applying to said skin allograft or said underlying tissue an effective graft incorporation promoting amount of a composition comprising a pharmacologically acceptable carrier and a compound selected from the group consisting of angiotensin II, an analog of angiotensin II, a fragment of angiotensin II and an analog of a fragment of angiotensin II;
contacting said skin allograft and said underlying tissue; and
securing said skin allograft to said underlying tissue, whereby incorporation of said skin allograft into said underlying tissue is promoted.

33. The method of claim 32, wherein said compound is a peptide consisting of at least three contiguous amino acids of groups $R^1$–$R^8$ in the general formula

wherein $R^1$ is selected from the group consisting of Asp, Glu, Asn, Acpc, Ala, $Me^2$Gly, Pro, Bet, Glu($NH_2$), Gly, Asp($NH_2$) and Suc;
$R^2$ is selected from the group consisting of Arg, Lys, Ala, Orn, Ser(Ac), Sar, D-Arg and D-Lys;
$R^3$ is selected from the group consisting of Val, Ala, Leu, norLeu, Ile, Gly, Pro, Aib, Acpc and Tyr;
$R^4$ is selected from the group consisting of Tyr, Tyr($PO_3$)$_2$, Thr, Ser, homoSer and azaTyr;
$R^5$ is selected from the group consisting of Ile, Ala, Leu, norLeu, Val and Gly;
$R^6$ is His, Arg or 6-$NH_2$-Phe;
$R^7$ is Pro or Ala; and R[8] is seleted from the group consisting of Phe, Phe(Br), Ile and Tyr, excluding sequences including R[4] as a terminal Tyr group.

34. The method of claim 32, wherein said compound is a peptide having the general formula $$R^2-R^3-R^4-R^5-R^6-R^7-R^8$$

in which R[2] is selected from the group consisting of H, Arg, Lys, Ala, Orn, Ser(Ac), Sar, D-Arg and D-Lys;

R[3] is selected from the group consisting of Val, Ala, Leu, norLeu, Ile, Gly, Pro, Aib, Acpc and Tyr;

R[4] is selected from the group consisting of Tyr, Tyr(PO$_3$)$_2$, Thr, Ser, homoSer and azaTyr;

R[5] is selected from the group consisting of Ile, Ala, Leu, norLeu, Val and Gly;

R[6] is His, Arg or 6-NH$_2$-Phe;

R[7] is Pro or Ala; and

R[8] is selected from the group consisting of Ile, Phe, Phe(Br) and Tyr.

35. The method of claim 32, wherein the allograft is a living skin equivalent.

36. A method of promoting incorporation of a skin xenograft into underlying tissue of a mammal, comprising the steps of:

applying to said skin xenograft or said underlying tissue an effective graft incorporation promoting amount of a composition comprising a pharmacologically acceptable carrier and a compound selected from the group consisting of angiotensin II, an analog of angiotensin II, a fragment of angiotensin II and an analog of a fragment of angiotensin II;

contacting said skin xenograft and said underlying tissue; and securing said skin xenograft to said underlying tissue, whereby incorporation of said skin xenograft into said underlying tissue is promoted.

37. The method of claim 36, wherein said compound is a peptide consisting of at least three contiguous amino acids of groups R[1]–R[8] in the general formula $$R^1-R^2-R^3-R^4-R^5-R^6-R^7-R^8$$

wherein R[1] is selected from the group consisting of Asp, Glu, Asn, Acpc, Ala, Me$^2$Gly, Pro, Bet, Glu(NH$_2$), Gly, Asp(NH$_2$) and Suc;

R[2] is selected from the group consisting of Arg, Lys, Ala, Orn, Ser(Ac), Sar, D-Arg and D-Lys;

R[3] is selected from the group consisting of Val, Ala, Leu, norLeu, Ile, Gly, Pro, Aib, Acpc and Tyr;

R[4] is selected from the group consisting of Tyr, Tyr (PO$_3$)$_2$, Thr, Ser, homoSer and azaTyr;

R[5] is selected from the group consisting of Ile, Ala, Leu, norLeu, Val and Gly;

R[6] is His, Arg or 6-NH$_2$-Phe;

R[7] is Pro or Ala; and

R[8] is selected from the group consisting of Phe, Phe (Br), Ile and Tyr, excluding sequences including R[4] as a terminal Tyr group.

38. The method of claim 36, wherein said compound is a peptide having the general formula $$R^2-R^3-R^4-R^5-R^6-R^7-R^8$$

in which R[2] is selected from the group consisting of H, Arg, Lys, Ala, Orn, Ser(Ac), Sar, D-Arg and D-Lys;

R[3] is selected from the group consisting of Val, Ala, Leu, norLeu, Ile, Gly, Pro, Aib, Acpc and Tyr;

R[4] is selected from the group consisting of Tyr, Tyr(PO$_3$)$_2$, Thr, Ser, homoSer and azaTyr;

R[5] is selected from the group consisting of Ile, Ala, Leu, norLeu, Val and Gly;

R[6] is His, Arg or 6-NH$_2$-Phe;

R[7] is Pro or Ala; and

R[8] is selected from the group consisting of Ile, Phe, Phe(Br) and Tyr.

39. The method of claim 36, wherein the xenograft is a living skin equivalent.

* * * * *

```
                          SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Asp Arg Val Tyr Ile His Pro Phe
1               5

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 6...6
        (D) OTHER INFORMATION: Position 6 is p-NH2-Phe
```

(xi) SEQUENCE DESCRIPTION: SEQ ID NO:2:

Asp Arg Val Tyr Ile Xaa Pro Phe
1               5

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Arg Val Tyr Ile His Pro Phe
1               5

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Val Tyr Ile His Pro Phe
1               5

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Asp Arg Val Tyr Ile His Pro
1               5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Arg Val Tyr Ile His Pro
1               5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Val Tyr Ile His Pro
1               5

(2) INFORMATION FOR SEQ ID NO:8:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Ile His Pro Phe
1

(2) INFORMATION FOR SEQ ID NO:9:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Asp Arg Val Tyr Ile His
1               5

(2) INFORMATION FOR SEQ ID NO:10:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Asp Arg Val Tyr Ile
1               5

(2) INFORMATION FOR SEQ ID NO:11:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Asp Arg Val Tyr
1

(2) INFORMATION FOR SEQ ID NO:12:

(i) SEQUENCE CHARACTERISTICS:
            (A) LENGTH: 3 amino acids
            (B) TYPE: amino acid
            (C) STRANDEDNESS: single
            (D) TOPOLOGY: linear

```
    (ii) MOLECULE TYPE: peptide (xi) SEQUENCE DESCRIPTION: SEQ ID NO:12:

Asp Arg Val
 1

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 2...2
         (D) OTHER INFORMATION: Position 2 is norLeu (xi) SEQUENCE DESCRIPTION: SEQ ID NO:13:

Arg Xaa Tyr Ile His Pro Phe
 1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 4...4
         (D) OTHER INFORMATION: Position 4 is norLeu (xi) SEQUENCE DESCRIPTION: SEQ ID NO:14:

Arg Val Tyr Xaa His Pro Phe
 1               5

(2) INFORMATION FOR SEQ ID NO:15:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

His Pro Phe
 1

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Tyr Ile His Pro Phe
```

1               5

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Xaa Xaa Tyr Xaa His Pro Phe
1               5

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Arg Val Tyr Gly His Pro Phe
1               5

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Arg Val Tyr Ala His Pro Phe
1               5

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Asp Arg Val Tyr Val His Pro Phe
1               5

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Asn Arg Val Tyr Val His Pro Phe
  1               5
```

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Ala Pro Gly Asp Arg Ile Tyr Val His Pro Phe
  1               5                  10
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Glu Arg Val Tyr Ile His Pro Phe
  1               5
```

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Asp Lys Val Tyr Ile His Pro Phe
  1               5
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Asp Arg Ala Tyr Ile His Pro Phe
  1               5
```

(2) INFORMATION FOR SEQ ID NO:26:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Asp Arg Val Thr Ile His Pro Phe
1               5
```

(2) INFORMATION FOR SEQ ID NO:27:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Asp Arg Val Tyr Leu His Pro Phe
1               5
```

(2) INFORMATION FOR SEQ ID NO:28:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Asp Arg Val Tyr Ile Arg Pro Phe
1               5
```

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Asp Arg Val Tyr Ile His Ala Phe
1               5
```

(2) INFORMATION FOR SEQ ID NO:30:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Asp Arg Val Tyr Ile His Pro Tyr
1               5
```

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide

```
        (xi) SEQUENCE DESCRIPTION: SEQ ID NO:31:

Pro Arg Val Tyr Ile His Pro Phe
 1               5

(2) INFORMATION FOR SEQ ID NO:32:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:32:

Asp Arg Pro Tyr Ile His Pro Phe
 1               5

(2) INFORMATION FOR SEQ ID NO:33:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (B) LOCATION: 4...4
         (D) OTHER INFORMATION: Position 4 is Tyr(PO3)2

(xi) SEQUENCE DESCRIPTION: SEQ ID NO:33:

Asp Arg Val Xaa Ile His Pro Phe
 1               5

(2) INFORMATION FOR SEQ ID NO:34:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (B) LOCATION: 3...3
         (D) OTHER INFORMATION: Position 3 is norLeu (xi) SEQUENCE DESCRIPTION: SEQ ID NO:34:

Asp Arg Xaa Tyr Ile His Pro Phe
 1               5

(2) INFORMATION FOR SEQ ID NO:35:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (B) LOCATION: 5...5
         (D) OTHER INFORMATION: Position 5 is norLeu
```

(xi) SEQUENCE DESCRIPTION: SEQ ID NO:35:

Asp Arg Val Tyr Xaa His Pro Phe
1               5

(2) INFORMATION FOR SEQ ID NO:36:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 4...4
            (D) OTHER INFORMATION: Position 4 is homoSer (xi) SEQUENCE DESCRIPTION: SEQ ID NO:36:

Asp Arg Val Xaa Tyr Ile His Pro Phe
1               5

(2) INFORMATION FOR SEQ ID NO:37:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:37:

Ser Arg Val Tyr Ile His Pro Phe
1               5

(2) INFORMATION FOR SEQ ID NO:38:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:38:

Arg Val Tyr Ile His Pro Ile
1               5

(2) INFORMATION FOR SEQ ID NO:39:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:39:

Arg Val Tyr Val His Pro Phe
1               5

(2) INFORMATION FOR SEQ ID NO:40:

(i) SEQUENCE CHARACTERISTICS:
            (A) LENGTH: 7 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:40:

Lys Val Tyr Ile His Pro Phe
1               5

(2) INFORMATION FOR SEQ ID NO:41:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:41:

Arg Ala Tyr Ile His Pro Phe
1               5

(2) INFORMATION FOR SEQ ID NO:42:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:42:

Arg Val Thr Ile His Pro Phe
1               5

(2) INFORMATION FOR SEQ ID NO:43:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:43:

Arg Val Tyr Leu His Pro Phe
1               5

(2) INFORMATION FOR SEQ ID NO:44:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:44:

Arg Val Tyr Ile Arg Pro Phe
1               5

(2) INFORMATION FOR SEQ ID NO:45:

(i) SEQUENCE CHARACTERISTICS:

```
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:45:

Arg Val Tyr Ile His Ala Phe
1               5

(2) INFORMATION FOR SEQ ID NO:46:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:46:

Arg Val Tyr Ile His Pro Tyr
1               5
```